United States Patent
Weinberg et al.

(10) Patent No.: US 6,670,298 B1
(45) Date of Patent: *Dec. 30, 2003

(54) COMBINATORIAL SYNTHESIS AND ANALYSIS OF ORGANOMETALLIC COMPOUNDS AND CATALYSTS

(75) Inventors: W. Henry Weinberg, Woodside, CA (US); Eric McFarland, San Jose, CA (US); Isy Goldwasser, Menlo Park, CA (US); Thomas Boussie, Menlo Park, CA (US); Howard Turner, Campbell, CA (US); Johannes A. M. Van Beek, Mountain View, CA (US); Vince Murphy, Cupertino, CA (US); Timothy Powers, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/337,612

(22) Filed: Jun. 21, 1999

Related U.S. Application Data

(62) Division of application No. 08/898,715, filed on Jul. 22, 1997, now Pat. No. 6,030,917.
(60) Provisional application No. 60/048,987, filed on Jun. 9, 1997, provisional application No. 60/035,366, filed on Jan. 10, 1997, provisional application No. 60/029,255, filed on Oct. 25, 1996, provisional application No. 60/028,106, filed on Oct. 9, 1996, and provisional application No. 60/016,102, filed on Jul. 23, 1996.

(51) Int. Cl.⁷ .......................... B01J 31/00; B01J 37/00; C08F 4/02; G01N 31/10; G01N 33/545
(52) U.S. Cl. ..................... 502/104; 435/4; 435/7.1; 435/7.2; 435/DIG. 10; 435/DIG. 19; 436/37; 436/149; 436/518; 436/531; 502/1; 502/2; 502/102; 502/103; 502/150; 502/527.14
(58) Field of Search .................. 436/37, 149, 531, 436/518; 435/7.1, 7.2, DIG. 10, DIG. 19, 4; 502/102–104, 1, 2, 150, 527.14

(56) References Cited

U.S. PATENT DOCUMENTS

| | | |
|---|---|---|
| 3,431,077 A | 3/1969 | Danforth |
| 3,919,589 A | 11/1975 | Hanak |
| 4,157,313 A | 6/1979 | Conan et al. |
| 4,287,094 A | 9/1981 | Panster et al. |
| 4,752,597 A | 6/1988 | Turner ........................ 502/104 |
| 4,814,377 A | 3/1989 | Joyce |
| 4,885,376 A | 12/1989 | Verkade |
| 5,064,802 A | 11/1991 | Stevens et al. ............. 502/155 |
| 5,096,867 A | 3/1992 | Canich |
| 5,198,401 A | 3/1993 | Turner et al. ............... 502/155 |
| 5,236,998 A | 8/1993 | Lundeen et al. |
| 5,260,461 A | 11/1993 | Hartung et al. |
| 5,262,571 A | 11/1993 | Comins et al. |

(List continued on next page.)

FOREIGN PATENT DOCUMENTS

| | | |
|---|---|---|
| DE | 104966 | 4/1974 |
| DE | 3042410 A1 | 5/1982 |
| GB | 2 176 932 A | 1/1987 |
| WO | WO 96/11878 | 4/1996 |
| WO | WO 96/13529 | 5/1996 |
| WO | WO 96/23010 | 8/1996 |

OTHER PUBLICATIONS

Burgess et al. Mol. Diversity Comb. Chem.: Libr. Drug Discovery, Conf., pp. 128–136. Editor(s): Chaiken, Irwin M.; Janda, Kim D. Publisher: American Chemical Society, Washington, D.C., 1996.*

Burgess et al. Angew. Chem. Intl. Ed. Engl. vol. 35, No. 2, pp. 220–222, Feb. 1996.*

Gordon et al. J. Med. Chem., vol. 37, No. 10, pp. 1385–1401, May 1994.*

R. Drago et al. "An Investigation of Unique Metal Complexes Produced Using Polystyrene–2,2'–bipyridine as a Support, and Several Hydrogenation Catalysts Derived from this Copolymer" Report 1981, ONR–TR–5, (AD No. AD97174) 29 pages.

C.U. Pittman Jr., et al. "Catalytic Reactions Promoted by Homogeneous Catalysts Attached to Polystyrene Matrices" Collogues Internationaux du C.N.R.S., No. 281, (1978) pp. 49–100.

E. Lindner et al. "Darstellung und Eigenschafter loslicher und Polysiloxan–gebundener (Ether–Phosphan)ruthenium(II)–Komplexe" Z. Anorg. Allg. Chem., vol. 598/599 (1991) pp. 235–252.

V. A. Semikolenov et al. "Effect of Dentate Number of Anchored Phosphine Ligands on the Composition and Catalytic Properties of Their Palladium Complexes" React. Kinet. Catal. Lett., vol. 10, No. 1 (1979) pp. 105–110.

M. Peuckert et al. "Hetherogenization of Homogeneous Nickel–Based Ethylene Oligomerization Catalysts" Journal of Molecular Catalysis, vol. 22 (1984) pp. 289–295.

T. Uematsu et al. "Hydrogenation and Isomerization of Olefins on Heterogenized Rhodium Complexes" Journal of Molecular Catalysis, vol. 12 (1981) pp. 11–26.

C–Y Hu et al. "Hydrosilylation Catalyzed by Polysiloxane–Bound Platinum Complexes" Journal of Macromol. Sci.–Chem., vol. A26, No. 2 & 3 (1989) pp. 349–360.

(List continued on next page.)

*Primary Examiner*—Maurie Garcia Baker
(74) *Attorney, Agent, or Firm*—Senniger, Powers, Leavitt & Roedel

(57) ABSTRACT

The present invention relates, inter alia, to methodologies for the synthesis, screening and characterization of organometallic compounds and catalysts (e.g., homogeneous catalysts). The methods of the present invention provide for the combinatorial synthesis, screening and characterization of libraries of supported and unsupported organometallic compounds and catalysts (e.g., homogeneous catalysts). The methods of the present invention can be applied to the preparation and screening of large numbers of organometallic compounds which can be used not only as catalysts (e.g., homogeneous catalysts), but also as additives and therapeutic agents.

41 Claims, 27 Drawing Sheets

U.S. PATENT DOCUMENTS

| | | | |
|---|---|---|---|
| 5,278,119 A | 1/1994 | Turner et al. | 502/155 |
| 5,318,935 A | 6/1994 | Canich et al. | 502/117 |
| 5,356,756 A | 10/1994 | Cavicchi et al. | |
| 5,447,895 A | 9/1995 | Marks et al. | 502/117 |
| 5,470,927 A | 11/1995 | Turner et al. | 526/126 |
| 5,470,993 A | 11/1995 | Devore et al. | 556/11 |
| 5,474,796 A | 12/1995 | Brennan | 427/2.13 |
| 5,495,036 A | 2/1996 | Wilson et al. | 556/12 |
| 5,502,017 A | 3/1996 | Marks et al. | 502/103 |
| 5,502,124 A * | 3/1996 | Crowther et al. | 526/127 |
| 5,504,049 A | 4/1996 | Crowther et al. | 502/117 |
| 5,508,458 A | 4/1996 | Zhao | |
| 5,550,094 A | 8/1996 | Ali et al. | 502/115 |
| 5,599,761 A | 2/1997 | Turner | 502/152 |
| 5,646,084 A | 7/1997 | Patton et al. | 502/152 |
| 5,679,548 A | 10/1997 | Barbas et al. | |
| 5,744,305 A | 4/1998 | Fodor et al. | |
| 5,801,113 A | 9/1998 | Jejelowo et al. | |
| 5,840,485 A | 11/1998 | Lebl et al. | |
| 5,880,241 A * | 3/1999 | Brookhart et al. | |
| 5,985,214 A | 11/1999 | Stylli et al. | |
| 5,985,356 A | 11/1999 | Schultz et al. | |
| 6,004,617 A * | 12/1999 | Schultz et al. | |
| 6,015,880 A | 1/2000 | Baldeschwieler et al. | |
| 6,030,917 A | 2/2000 | Weinberg et al. | |
| 6,063,633 A | 5/2000 | Willson, III | |
| 6,140,432 A | 10/2000 | Agapiou et al. | |
| 6,248,540 B1 * | 6/2001 | Weinberg et al. | 435/7.1 |

OTHER PUBLICATIONS

J. Hjortkjaer et al. "Influence of the Ligand Structure on SLP–Catalysed Hydroformylation of Propene" Applied Organometallic Chemistry, vol. 4 (1990) pp. 369–374.

A. Sanger et al. "The Structures and Hydroformylation Catalytic Activities of Polyphosphine Complexes of Rhodium(I), and Related Complexes Immobilised on Polymer Supports" Journal of Molecular Catalysis, vol. 3 (1977/78) pp. 101–109.

J. Stille et al. "Organic Synthesis via Polymer–Supported Transition Metal Catalysts" Reactive Polymers, vol. 10 (1989) pp. 165–174.

C. De–An et al. "2–Pentene Hydroformylation Catalyzed by Polymer–Anchored Versus Homogeneous Cobalt Complexes: The Effect of Chelating Phosphine" Journal of Molecular Catalysis, vol. 21 (1983) pp. 405–414.

M. Berglund et al. "Polar Organic Polymer as Catalyst Support in the Olefin Metathesis Reaction" Journal of Molecular Catalysis, vol. 36 (1986) pp. 375–386.

L. Hong et al. "Preparation of Polymer–Supported Catalysts Containing Phosphorus Palladium Complexes and Quarternary Onium Groups, and their Application to the Vinylation Reaction" Reactive Polymers, vol. 16 (1991/1992) pp. 181–197.

C. Lepetit et al. "Propylene Dimerization Over Silica–Supported Complexes: Electronic and Steric Effect of the Trialkylphosphine Ligand" Journal of Molecular Catalysis, vol. 51 (1989) pp. 95–113.

Z. Michalska "Rhodium Carbonyl Complexes With Polymer–Bound Bidentate Amine–Phosphine Ligands" Journal of Molecular Catalysis, vol. 19 (1983) pp. 345–358.

A. Kinting et al. "Silica–Supported Chiral Rhodium Complexes for Asymmetric Hydrogenation" Journal of Molecular Catalysis, vol. 33 (1985) pp. 215–223.

T. Jongsma et al. "Stable Silica–Grafted Polymer–Bound Bulky–Phosphite Modified Rhodium Hydroformylation Catalysts" Journal of Molecular Catalysis, vol. 83 (1993) pp. 37–50.

J. John et al. "Synthesis, Characterisation and Catalytic Activity of Styrene–Divinylbenzene Copolymer (XAD–2) Bound Palladium(II) Complex" Polymer International, vol. 34 (1994) pp. 369–373.

B. De et al. "Synthesis of Catalytically Active Polymer–Bound Transition Metal Complexes for Selective Epoxidation of Olefins" Macromolecules, vol. 27, No. 6 (1994) pp. 1291–1296.

J. Bognar, Quantitative Evaluation of Catalytic Reactions: the Simultaneous Comparison Method Mikrochim. Ichnoanal. Acta vol. 5–6 (1963) pp. 801–828 (in German); CA 58, 13179f. Abstract only.

S. T. Darian "Catalysts for $NO_x$ Reduction Using Ammonia" Environmental Progress, vol. 1, No. 2 (May 1982) pp. 84–88.

V. Goetz "Catalyst Evaluation for the Simultaneous Reduction of Sulfur Dioxide and Nitric Oxide by Carbon Monoxide" Ind. Eng. Chem., Prod. Res. Develop., vol. 13, No. 2 (1974) pp. 110–114.

T. R. Halbert "Synthesis and Activity of Hydrotreating Catalysts Prepared via Promotion by Low–Valent Transition–Metal Complexes" J. of Catalysis, vol. 130 (1991) pp. 116–129.

Y. Joh "Stereospecific Polymerization of Methyl Methacrylate by Organomagnesium Catalysts with a Magnesium–Nitrogen Bond" Macromolecules, vol. 3, No. 3 (May/Jun. 1970), pp. 337–345.

I. E. Uflyand "Comparative Analysis of Homogeneous and Immobilized Catalysts for Ethylene Dimerization Based on Nickel(II) Chelates" J. of Molecular Catalysis, vol. 55 (1989) pp. 302–310.

B. Wallin "Liproprotein Oxidation and Measurement of Thiobarbituric Acid Reacting Substances Formation in a Single Microtiter Plate: Its Use for Evaluation of Antioxidants" Analytical Biochemistry, vol. 208 (1993) pp. 10–15.

J. M. Basset et al. "From Clusters and Surfaces to Clusters on Surfaces: an Opening Toward Surface Organometallic Chemistry" Materials Chemistry and Physics, vol. 29, 5–32 (1991).

R. G. Bergman "Synthesis and Reactions of Monomeric Late Transition Metal Alkoxo, Aryloxo and Hydroxo Complexes" Polyhedron, vol. 14, No. 22, 3227–3237 (1995).

M. R. Bermejo et al. "The Diversity Observed in Manganese(III) Complexes of Tetradentate Schiff Base Ligands: An Assessment of Structural Trends" Polyhedron, vol. 15, No. 23, 4185–4194 (1996).

E. K. Bijpost et al. "Early Transition Metal Catalyzed–Hydroboration of Alkenes" Journal of Molecular Catalysis A: Chemical, vol. 95, 121–128 (1995).

K. Burgess et al. "Libraries of Catalysts" CAPLUS, 1996:220884, Book of Abstracts 211th ACS National Meeting (1996).

V. A. Burgess et al. "Chiral Organometallic NADH Mimics: Highly Stereoselective Reductions of Ethyl Benzoylformate with a 1,4–dihydronicotinoyl Fragment Attached to the Homochiral Auxiliary [$\eta^5$–$C_5H_5$)Fe(CO)(PPh$_3$)] and Possessing a Homochiral β–hydroxy–carboxamide at C–5" Tetrahedron Assym., vol. 3, No. 7, 871–901 (1992).

M. Capka et al. "Hydrogenation Activity of Homogeneous and Heterogenized Cyclopentadienyl Titanum Complexes" *Collect. Czech. Chem. Commun.*, vol. 54, No. 7, 1760–1769 (1989).

C. Carlini et al. "Complexes of Ruthenium (II) and Rhodium (I) with N– and P–Donor Macromolecular Ligands: Preparation and Catalytic Isomerisation of Olefins" *Journal of Molecular Catalysis*, vol. 2, 379–397 (1977).

O. L. Casagrande Jr. "Small Angle X–Ray Scattering and IR Spectroscopy Study of Metal Carbonyl Complexes Immobilized on a Silica Gel Surface Chemically Modified with Piperazine" *Polyherdron*, vol. 15, No. 23, 4179–4183 (1996).

W. Chen et al. "Studies on Immobilized Polymer–Bound Imidazole–Copper(II) Complexes as Catalysts. 3. Immobilization of Copper(II) Complexes of Poly(styrene–co–N–vinylimidazole) by Grafting on Silica and Their Catalysis of Oxidative Coupling of 2,6–Disubstituted Phenols" *Macromolecules*, vol. 24, No. 14, 3982–3987 (1991).

V. R. Choudhary et al. "Isomerization of n–Butene to Isobutene* I. Selection of Catalyst by Group Screening" *Journal of Catalysis*, vol. 23, 54–60 (1971).

A. Corma et al. "Optically active complexes of transition metals ($Rh^I$, $Ru^{II}$, $CO^{II}$ and $Ni^{II}$) with 2–aminocarbonylpyrrolidine ligands. Selective catalysts for hydrogenation of prochiral olefins" *Journal of Organometallic Chemistry*, 431, 233–246 (1992).

J. G. Creer et al. "The Design and Construction of a Multichannel Microreactor for Catalyst Evaluation" *Applied Catalysis*, vol. 22, 85–95 (1986).

K. Czaja "Deactivation of Complex Organometallic Catalysts" *Polimery*, vol. 38, 380–386 (1983). Abstract only.

K. Czaja "Deactivation of Complex Organometallic Catalysts" Chem. Abstracts, vol. 121, No. 2, Abstract No. 10027v (1994).

D.J. Darensbourg et al. "Phase–Transfer–Catalyzed Nucleophilic Reactions of Hydroxide Ions at Metal–Bound Carbon Monoxide Centers" *J. Am. Chem. Soc.*, vol. 102, No. 14, 4688–4694 (1980).

G. Desimoni et al. "Copper (II) in Organic Synthesis. XI. Evaluation of the Ligand Architecture on the Efficiency of a Copper (II) Catalyst for Enantioselective Michael Reactions" *Tetrahedron*, vol. 51, No. 14, 4131–4144 (1995).

G. Erker "Stereoselective Synthesis with Zirconium Complexes" *Pure Appl. Chem.*, vol. 64, No. 3, 393–401 (1992).

T. Fawccett "Greater than the sum of its parts: A new instrument" *CHEMTECH*, vol. 17, No. 9, 564–569 (1987).

J–C. Fiaud et al. "Preparation of Optically Pure 1,2,5–Triphenylphospholane. Use as Ligand for Enantioselective Transition–Metal Catalysis" *Tetrahedron Letters*, vol. 32, No. 38, 5089–5092 (1991).

D. E. Fogg et al. "A Comparison of Catalytic Activity for Imine Hydrogenation Using Ru Ditertiary Phosphine Complexes, Including Chiral Systems" *Inorganica Chimica Acta*, vol. 222, 85–90 (1994).

M. M. C. Forte "Immobilized Catalyst System in Hydrogenated Hydroxylated Polybutadiene for Ethylene Polymerization" *Journal of Polymer Science: Polymer Lettetters Ed.*, vol. 22, 25–30 (1984).

H. Furhmann "Ziegler–Natta Polymerization of Ethylene with Titanium–Magnesium Catalysts Anchored on Polymeric Supports" Chem. Abstracts, vol. 120, No. 2, Abstract No. 9005j (1994).

H. Furhmann et al. "Ziegler–Natta Polymerization of Ethylene with Ti–Mg Catalysts Anchored on Polymeric Supports" *Acta Polym.*, vol. 44, 156–162 (1993).

M. Gallop et al. "Applications of Combinatorial Technologies to Drug Discovery. 1. Background and Peptide Combinatorial Libraries" *J. of Med. Chem.*, vol. 37, No. 9 1233–1251 (1994).

B. C. Gates "Summary of Accomplishments in DOE–Sponsored Project Entitled Metal–Support Bonds in Supported Metal Catalysts" Report, DOE/ER/13790–13793 (1990).

E. Gehrer et al. "A Fully Programmable System for the Study of Catalytic Gas Reactions" *Journal of Physics E: Sci. Instrum.*, vol. 18, No. 10, 836–838 (1985).

J. P. Genet et al. "Enantioselective Hydrogenation Reactions with a Full Set of Preformed and Prepared in situ Chiral Diphosphine–Ruthenium (II) Catalysts" *Tetrahedron Asymmetry*, vol. 5, No. 4, 675–690 (1994).

G. Georgiades "IR Emission Analysis of Temperature Profiles in $Pt/SiO_2$ Catalysts during Exothermic Reactions" *Angew Chem. Int. Ed. Engl.*, vol. 26, No. 10, 1042–1043 (1987).

A. Gusso et al. "Platinum–Catalyzed Oxidations with Hydrogen Peroxide: Enantiospecific Baeyer–Villiger Oxidation of Cyclic Ketones" *Organometallics*, vol. 13, No. 9, 3442–3451 (1994).

J. J. Hanak "The Multiple–Sample Concept In Materials Research: Synthesis, Compositional Analysis and Testing of Entire Multicomponent Systems" *Journal of Materials Science*, vol. 5, 964–971 (1970).

J. J. Hanak "A Step Toward Automation of Materials Research" *RCA Technical Report*, 12 pages (1969).

C. C. Hsu "Light–Off Temperature Determination of Oxidation Catalyst Using FTIR Technique" *Preprints Symposium, American Chem. Soc., Div. Petroleum Chem.*, vol. 33, No. 4, 643–647 (1988).

J. V. Jensen et al. "A Deactivation Reactor for Catalyst Screening and Evaluation" *Proc. Int. Congr. Catal. 6th, Chemical Soc.*, vol. 2 796–805 (editor G. C. Bond) (1977).

J. C. Kenvin et al. "Preparation and Characterization of Supported Monomuclear Metal Complexes as Model Catalysts" *Langmuir*, vol. 7, 1198–1205 (1991).

L. Kiezel et al. "A Comparative Semi–Micromethod of Investigating the Catalyst Activity" *Chemica Stosowana*, vol. 12, No. 3A, 407–415 (1968).

K. Krohn et al. "Asymmetric Induction in Kinetically Controlled Zirconium–Catalysed Meerwein–Ponndorf–Verley Reductions" *Recl. Tav. Chim. Pays–Bas*, 115, 140–144 (1996).

C. Leznoff "The Use of Insoluble Polymer Supports in General Organic Synthesis" Acc. Chem. Res., vol. 11, 327–333 (1978).

D. Li et al. "Synthesis, Characterization, and Properties of Covalently Bound, Self–Assembled Porphyrin Multilayer Thin Films" *Chem. Mater.*, vol. 6, No. 6, 803–810 (1994).

T. Madach et al. "Bildung und Zerfall einfacher Metallcarbonyl–Zweikern–komplese als Gleichgewichtsreaktion" *Chem. Ber.*, vol. 113, 2675–2685 (1980). Abstract only.

D. Mansuy et al. "Highly Oxidation Resistant Inorganic–Porphyrin Analogue Polyoxometalate Oxidation Catalysts. 2. Catalysis of Olefin Epoxidation and Aliphatic and Aromatic Hydroxylations Starting from $\alpha_2$–$P_2W_{17}O_{61}(M^{n+}$•$Br)^{(n-11)}$ ($M^{n+}=Mn^{3+}$, $Fe^{3+}$, $Co^{2+}$, $Ni^{2+}$, $Cu^{2+}$), Including Quantitative Comparisons to Metalloporphyrin Catalysts" *J. Am. Chem. Soc.*, vol. 113, No. 19, 7222–7226 (1991).

A. Marinetti et al. "Phosphetanes as Chiral Ligands for Catalytic Asymmetric Reactions: Hydrosilylation of Olefins" *Organometallics*, vol. 13, No. 10, 3956–3962 (1994).

G. Martin et al. "Integrated Enzyme Reactor/Detector for the Determination of Multiple Substrates by Image Analysis" Analytica Chemica Acta, vol. 281, 557–568 (1993).

H. Moorlag et al. "Palladium–Catalyzed Allylation of α–Hydroxy Acids" *Recl. Trav. Chim. Pays–Bas*, vol. 111, No. 3, 129–137 (1992).

J. Moss et al. "Electrocatalysis in Photochemically Activated Electropolymerized Thin Films" Inorg. Chem., vol. 39, No. 6, 1052–1058 (2000).

D. E. Newlin "Kinetics and Mechanism of Tetradentate Nickel(II) Chelate and Metal Nitrilotriacetate Promoted Hyrdolysis of Methyl Glycinate: an Isokinetic Relationship" *Journal of American Chemical Soc.*, vol. 99, No. 4, 1078–1082 (1977).

V. Nikolaiev et al. "Peptide–Encoding for Structure Determination of Nonsequenceable Polymers Within Libraries Synthesized and Tested on Solid–Phase Supports" *Peptide Research*, 6:3, 161–170 (1993).

R. Noyori et al. "Transition Metal Catalyzed [2 + 2] Cross–Adition of Olefins. Nickel(0)–Catalyzed Cycloaddition of Norbornadiene and Methylenecyclopropane" *Journal of American Chemical Soc.*, vol. 95, No. 5, 1674–1676 (1973).

M. G. L. Petrucci et al. "Heterogenizing Homogeneous Catalysis"– *Advanced Materials*, vol. 8, No. 3, 251–253 (1996).

G. Proulx et al. "Reactions of $Cp_2Ta(CH_2)(CH_3)$ with Substituted and Unsubstituted Metal Carbonyls (Groups 7, 8 and 9). Evidence for Intermediates Involved in the Carbon–Carbon Bond–Forming Steps of the Reduction and Deoxygenation of CO" *J. Am. Chem. Soc.*, vol. 118, No. 8, 1981–1996 (1996).

D. Roberto et al. "Extraction Methods and Surface Reactions as a Convenient Methodology for the Characterization of Surface Organometallic Species" *Journal of Molecular Catalysis A: Chemical*, vol. 111, 97–108 (1996).

K. K. Robinson et al. "Catalytic Vapor Phase Hydroformylation of Propylene over Supported Rhodium Complexes" *Journal of Catalysis*, vol. 15, 245–249 (1969).

C. Serrano "A Multifunctional in situ Catalyst Characterization Apparatus" *Applied Catalsis.*, vol. 19, 119–139 (1985).

M. C. Showalter "Biomimetic Catalyst Development for Natural Gas Conversion" *Prep. Pap.—Am. Chem. Soc., Div. Fuel. Chem.*, 39, 1002–1005A (1994).

H. Singer et al., "Vergleichende Dimerisierung der Enantiomere von Oct–1–in–3–ol mit chiralen Rhodium–Phosphan–Komplexen" *Journal of Organometallic Chem.*, vol. 508, No. 1–2, 267–269 (1969). Abstract only.

D. Singh et al. "Antifertility and Biocidal Activities of Organometallics of Silicon, Germanium, Titanium and Zirconium Derived form 2–Acetylthiophene Thiosemicarbazone" *Applied Organometalic Chem.*, vol. 7, 289–292 (1993).

W. Skupinski et al. "Investigation of Catalytic Systems Containing Nickel Supported on Allumina–Silica Bonded with Organic Ligands and Complexed by Lewis Acids" Chem. Abstracts, vol. 89, No. 8, Abstract No. 65951t (1978).

W. Skupinski et al. "Investigation of Catalytic Systems Containing Nickel Supported on Alumina–Silica Bonded with Organic Ligands and Complexed by Lewis Acids" *Journal of Molecular Catalysis*, vol. 4, 95–102 (1978).

K. Soga et al. "Polymerization of Propene with Highly Isospecific $SiO_2$–supported Zirconocene Catalysts Activated with Common Alkylaluminiums" *Macromol. Chem. Phys.*, vol. 195, 3347–3360 (1994).

M. Tomoi et al. "Synthesis of Spacer–modified Polymer Supports with the Aid of Etherification and Phase–transfer Catalytic Activity of Phosphonium Salts Derived form the Polymer Supports" *Makromol. Chem.*, vol. 187, 357–365 (1986).

Y. Tor et al. "Chiral Siderophore Analogs: Enterobactin" *J. Am. Chem. Soc.*, vol. 114, No. 17, 6661–6671 (1992).

N. Toshima "Immobilized Metal Complexes for Organic Synthesis" *Yuki Gosei Kagaku Kyokaishi*, vol. 36, 909–916 (1978). Abstract only.

I. E. Uflyand et al. Polymers Containing Metal Chelate Units. I. Immobilized mono– and Binuclear Chelates of Nickel(II) and Cobalt(II) *Chem. Abstr.* vol. 119, No. 2, abstract No. 9289j, (1993).

D. S. Zingg et al. "A Surface Spectroscopic Study of Molybdenum–Alumina Catalysts Using X–ray Photoelectron, Ion–Scattering, and Raman Spectroscopies" *J. Phys. Chem.*, vol. 84, No. 22, 2898–2906 (1980).

Gilbertson, Scott R., et al., "Versatile Building Block for the Synthesis of Phosphine–Containing Peptides: The Sulfide of Diphenylphosphinoserine," *J. Am. Chem. Soc.*, vol. 116, pp. 4481–4482, (1994).

Malin, Reinhard, et al., "Identification of Technetium–99m Binding Peptides Using Combinatorial Cellulose–Bound Peptide Libraries," *J. Am. Chem. Soc.*, vol. 117, pp. 11821–11822, (1995).

Xiang, X.–D., et al., "A Combinatorial Approach to Materials Discovery," *Science*, vol. 268, pp. 1738–1740, (1995).

*Molecular Diversity and Combinatorial Chemistry*, Chaiken, Irwin M and Janda Kim D. (Eds.), American Chemical Society, Washington, DC, USA, Chapter 12, pp. 128–136, (1996).

Gilbertson, Scott R., et al., "Synthesis of Phosphine–Rhodium Complexes Attached to a Standard peptide Synthesis Resin," *Organometallics*, vol. 15, pp. 4678–4680, (1996).

Burgess, Kevin, et al., "New Catalysts and Conditions for a C–H Insertion Reaction Identified by High Throughput Catalyst Screening," *Angew. Chem. Int. Ed. Engl.*, vol. 35, No. 2, pp. 220–222, (1996).

Gilbertson, Scott R., et al., "The Combinatorial Synthesis of Chiral Phosphine Ligands," *Tetrahedron Letters*, vol. 37, No. 36, pp. 6475–6478, (1996).

Menger, Fredric M., et al., "A Combinatorially Developed Reducing Agent," *Chem. Commun.*, pp. 633–634, (1996).

Gennari, Cesare, et al., "Combinatorial Libraries: Studies in Molecular Recognition and the Quest for New Catalysts," *Liebigs Ann./Recueil*, pp. 637–647, (1997).

Guerin et al., "Conformationally Rigid Diamide Complexes: Synthesis and Structure of Tantalum (III) Alkyne Derivatives," *Organometallics*, 1995, 14, 3154–3156.

Johnson et al., "New Pd(II)– and Ni(II)–Based Catalysts for Polymerization of Ethylene and α–Olefins," *J. Am. Chem. Soc.*, 1995, 117, 6414–6415.

Scollard et al., "Living Polymerization α–Olefins by Chelating Diamide Complexes of Titanium," *J. Am. Chem. Soc.*, 1996, 118, 10008–10009.

Thompson, Lorin A., et al., "Straightforward and general method for coupling alcohols to solid supports," *Tetrahedron Letters*, vol. 35, No. 50, pp. 9333–9336, 1994.

Menger, F.M., et al., "Phosphatase catalysis developed via combinatorial organic chemistry," *J. Org. Chem.*, vol. 60, pp. 6666–6667, 1995.

Liu, Guangcheng, et al., "A general solid–phase synthesis strategy for the preparation of 2-pyrrolidinemethanol ligands," *J. Org. Chem.*, vol. 60, 7712–7713.

Roach, Peter L., et al., "Crystal structure of isopenicillin N synthase is the first from a new structural family of enzymes," *Nature*, vol. 375, pp. 700–704, 1995.

Cole, Bridget M., et al., "Discovery of chiral catalysts through ligand diversity: Ti–catalyzed enantioselective addition of TMSCN to meso epoxides," *Angew. Chem. Ed. Engl.*, vol. 35, pp. 1668–1671, 1996.

Shibata, Noro, et al., "Resin–bound peptide libraries showing specific metal ion binding," *Bioorg. Med. Chem. Lett.*, vol. 7, pp. 413–416, 1997.

Shimizu, Ken D., et al., "Search for chiral catalysts through ligand diversity: Substrate–specific catalysts and ligand screening on solid phase," *Angew. Chem. Int. Ed. Engl.*, vol. 36, pp. 1704–1707, 1997.

Burger et al., *J. Org. Chem.*, 60: 7382–7383 (1995) Synthetic Ionophores, Encoded Combinatorial Libraries of Cyclen–based Receptors for $Cu^2$ and $Co^2$.

Francis, et al., *J. Am. Chem. Soc.*, 118: 8983–8984 (1996) Combinatorial Approach to the Discovery of Novel Coordination Complexes.

Moates, et al., *Ind. Eng. Chem. Res.*, 35: 4801–4803 (1996) Infrared Thermographic Screening of Combinatorial Libraries of Heterogeneous Catalysts.

\* cited by examiner

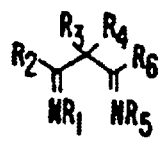
FIG. 4A
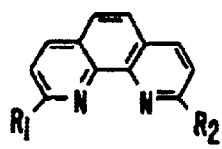
FIG. 4B
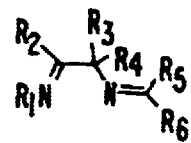
FIG. 4C
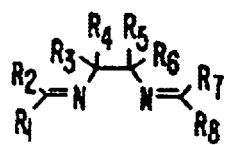
FIG. 4D
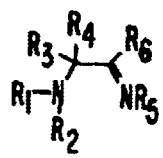
FIG. 4E
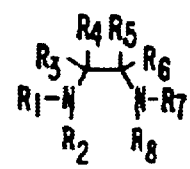
FIG. 4F
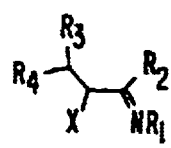
FIG. 4G
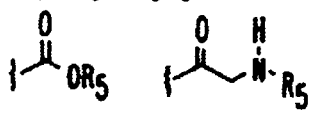
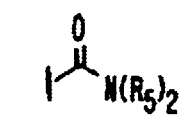

WHERE R₁ CONTAINS ACIDIC FUNCTIONALITY WHICH COMPETES
WITH METAL FOR BINDING POLAR FUNCTIONAL GROUP

COMBINATORIAL SYNTHESIS AND ANALYSIS OF ORGANOMETALLIC COMPOUNDS AND CATALYSTS

This application is a divisional application of U.S. patent application Ser. No. 08/898,715, filed Jul. 22, 1997 now U.S. Pat. No. 6,030,917, which is incorporated herein by reference and which claims the benefit of U.S. Provisional Application No. 60/048,987, filed Jun. 9, 1997; U.S. Provisional Application No. 60/035,366, filed Jan. 10, 1997; U.S. Provisional Application No. 60/029,255, filed Oct. 25, 1996; U.S. Provisional Application No. 60/028,106, filed Oct. 9, 1996; and U.S. Provisional Application No. 60/016,102, filed Jul. 23, 1996, the teachings of which are incorporated herein by reference.

FIELD OF THE INVENTION

The present invention relates, inter alia, to methodologies for the synthesis, screening and characterization of organometallic compounds and catalysts. The methods of the present invention provide for the combinatorial synthesis, screening and characterization of libraries of supported and unsupported organometallic compounds and catalysts. The methods of the present invention can be applied to the preparation and screening of large numbers of organometallic compounds which can be used not only as catalysts (e.g., homogeneous catalysts), but also as additives and therapeutic agents.

BACKGROUND OF THE INVENTION

Ancillary ligand-stabilized metal complexes (i.e., organometallic complexes) are useful as catalysts, additives, stoichiometric reagents, monomers, solid state precursors, therapeutic reagents and drugs. The ancillary ligand system comprises organic substituents, bind to the metal center(s), remain associated with the metal center(s), and therefore provide an opportunity to modify the shape, electronic and chemical properties of the active metal center(s) of the organometallic complex.

Certain organometallic complexes are catalysts for reactions such as oxidation, reduction, hydrogenation, hydrosilylation, hydrocyanation, hydroformylation, polymerization, carbonylation, isomerization, metathesis, carbon-hydrogen activation, cross coupling, Friedel-Crafts acylation and alkylation, hydration, dimerization, trimerization and Diels-Alder reactions. Organometallic complexes can be prepared by combining an ancillary ligand precursor with a suitable metal precursor in a suitable solvent at a suitable temperature. The yield ACTIVITY AND SELECTIVITY of the targeted organometallic complex is dependent on a variety of factors including the form of the ancillary ligand precursor, the choice of the metal precursor, the reaction conditions (e.g., solvent, temperature, time, etc.) and the stability of the desired product. In some cases, the resulting organometallic complex is inactive as a catalyst until it is "activated" by a third component or cocatalyst. In many cases, third component "modifiers" are added to active catalysts to improve performance. The effectiveness of the cocatalyst, the type and amount of modifier, and the suitability of the ancillary ligand precursor, metal precursor and reaction conditions to form an effective catalyst species in high yield are unpredictable from first principles. Given the number of variables involved and the lack of theoretical capability, it is not surprising that the discovery and optimization of catalysts is laborious and inefficient.

One important example of this is the field of single-sited olefin polymerization catalysis. The active site typically comprises an ancillary ligand-stabilized coordinatively unsaturated transition metal alkyl complex. Such catalysts are often prepared by the reaction of two components. The first component is an ancillary ligand-stabilized transition metal complex having a relatively low coordination number (typically between three and four). The second component, known as the activator or cocatalyst, is either an alkylating agent, a Lewis acid capable of abstracting a negatively charged leaving group ligand from the first component, an ion-exchange reagent comprising a compatible non-coordinating anion or a combination thereof. Although a variety of organometallic catalysts have been discovered over the past 15 years, this discovery is a laborious process which consists of synthesizing individual potentially catalytic materials and subsequently screening them for catalytic activity. The development of a more efficient, economical and systematic approach for the synthesis of novel organometallic catalysts and for the screening of such catalysts for useful properties would represent a significant advance over the current state of the art. A particularly promising method for simplifying the discovery process would rely on methods of producing combinatorial libraries of ligands and catalysts and screening the compounds within those libraries for catalytic activity using an efficient parallel or rapid serial detection method.

The techniques of combinatorial synthesis of libraries of organic compounds are well known. For example, Pirrung, et al. developed a technique for generating arrays of peptides and other molecules using, for example, light-directed, spatially-addressable synthesis techniques (U.S. Pat. No. 5,143,854 and PCT Publication No. WO 90/15070). In addition, Fodor, et al. have developed automated techniques for performing light-directed, spatially-addressable synthesis techniques, photosensitive protecting groups, masking techniques and methods for gathering fluorescence intensity data (Fodor, et al., PCT Publication No. WO 92/10092). In addition, Eliman, et al. recently developed a methodology for the combinatorial synthesis and screening of libraries of derivatives of three therapeutically important classes of organic compounds, benzodiazepines, prostaglandins and B-turn mimetics (see, U.S. Pat. No. 5,288,514).

Using these various methods of combinatorial synthesis, arrays containing thousands or millions of different organic elements can be formed (U.S. Pat. Application No. 805,727, filed Dec. 6, 1991). The solid phase synthesis techniques currently being used to prepare such libraries involve a stepwise process (i.e., sequential, coupling of building blocks to form the compounds of interest). In the Pirrung, et al. method, for example, polypeptide arrays are synthesized on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequences are synthesized. The Pirrung, et al. method is a sequential, step-wise process utilizing attachment, masking, deprotecting, attachment, etc. Such techniques have been used to generate libraries of biological polymers and small organic molecules to screen for their ability to specifically bind and block biological receptors (i.e., protein, DNA, etc.). These solid phase synthesis techniques, which involve the sequential addition of building blocks (i.e., monomers, amino acids) to form the compounds of interest, cannot readily be used to prepare many inorganic and organic compounds. As a result of their relationship to semiconductor fabrication techniques, these methods have come to be referred to as "Very Large Scale Immobilized Polymer Synthesis," or "VLSIPS" technology.

Schultz, et al. was the first to apply combinatorial chemistry techniques to the field of material science (PCT WO/9611878, the teachings of which are incorporated herein by reference). More particularly, Schultz, et al. discloses methods and apparatus for the preparation and use of a substrate having thereon an array of diverse materials in predefined regions. An appropriate array of materials is generally prepared by delivering components of materials to predefined regions on the substrate and simultaneously reacting the reactants to form different materials. Using the methodology of Schultz, et al., many classes of materials can be generated combinatorially including, for example, inorganic materials, intermetallic materials, metal alloys, ceramic materials, etc. Once prepared, such materials can be screened for useful properties. Liu and Ellman, *J. Org. Chem.* 1995, 60:7, working in the area of asymmetric catalysis, have developed a solid-phase synthesis strategy for the 2-pyrrolidinemethanol ligand class, and have demonstrated that the ligands can be directly evaluated for enantioselective additions of diethyl zinc reagent to aldehyde substrates using conventional analytical methods and not rapid parallel or serial screening methods.

From the above, it is apparent that there is a need for the development of methods for synthesizing and screening libraries of organometallic materials for catalytic properties. These methods would greatly accelerate the rate discovering and optimizing catalytic process. Quite surprisingly, the instant invention provides such methods.

SUMMARY OF THE INVENTION

The present invention relates to methods for the synthesis and characterization of arrays, i.e., libraries of catalysts and organometallic compounds.

More particularly, the methods of the present invention provide for the combinatorial synthesis, screening and characterization of large arrays or libraries of diverse supported and unsupported ligands, catalysts and organometallic compounds.

Thus, in one aspect, the present invention provides a method of making and screening an array of metal-ligand compounds, the method comprising:

(a) synthesizing a spatially segregated array of ligands;

(b) delivering a suitable metal precursor to each element of the array of ligands to create an array of metal-ligand compounds;

(c) optionally activating the array of metal-ligand compounds with a suitable cocatalyst;

(d) optionally modifying the array of metal-ligand compounds with a third component; and (e) screening the array of metal-ligand compounds for a useful property using a parallel or rapid serial screening technique selected from the group consisting of optical imaging, optical spectroscopy, mass spectrometry, chromatography, acoustic imaging, acoustic spectroscopy, infrared imaging and infrared spectroscopy.

In yet another aspect, the invention comprises an array of between 10 and $10^6$ different metal-ligand compounds at known locations on the substrate. In certain embodiments, the array will comprise more than 50 different metal-ligand compounds at known locations on the substrate. In other embodiments, the array will comprise more than 100 or more than 500 different metal-ligand compounds. In still further embodiments, the array will comprise more than 1,000, more than 10,000 or more than $10^6$ different metal-ligand compounds at known locations on the substrate.

Other features, objects and advantages of the invention and its preferred embodiments will become apparent from the detailed description which follows.

BRIEF DESCRIPTION OF THE DRAWINGS

FIGS. 4A–4G illustrate examples of ligand cores which can be made using combinatorial chemistry formats.

DETAILED DESCRIPTION OF THE INVENTION AND PREFERRED EMBODIMENTS

Table of Contents

Figure 1A:
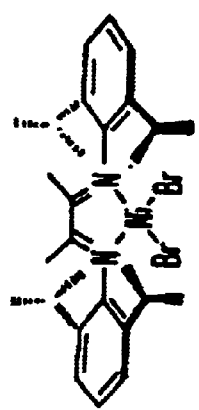
FIGS. 1A and 1B illustrate examples of transition-metal based metallocene catalysts and catalysts based on the late transition metals, e.g., zirconium and nickel, respectively.
Figure 1B:
Figure 2A:
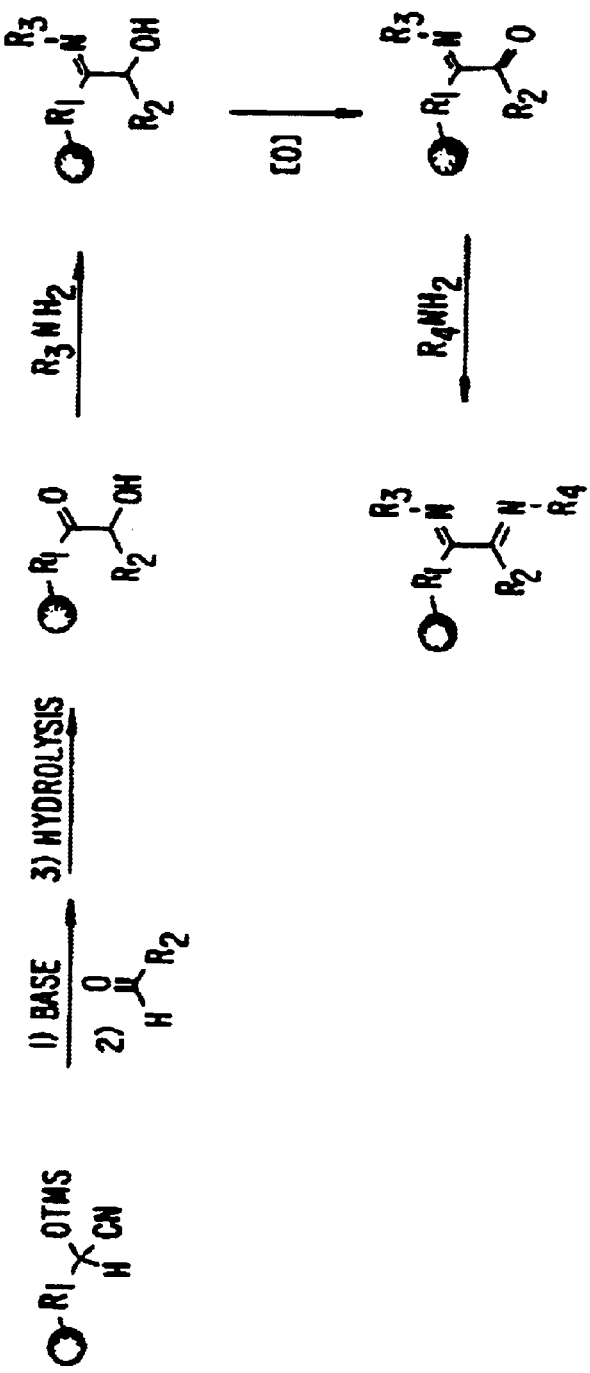
FIGS. 2A and 2B illustrate sequences of solid-phase reactions which can be used to achieve combinatorial variations of diimine and/or diamine ligands.
Figure 2B:
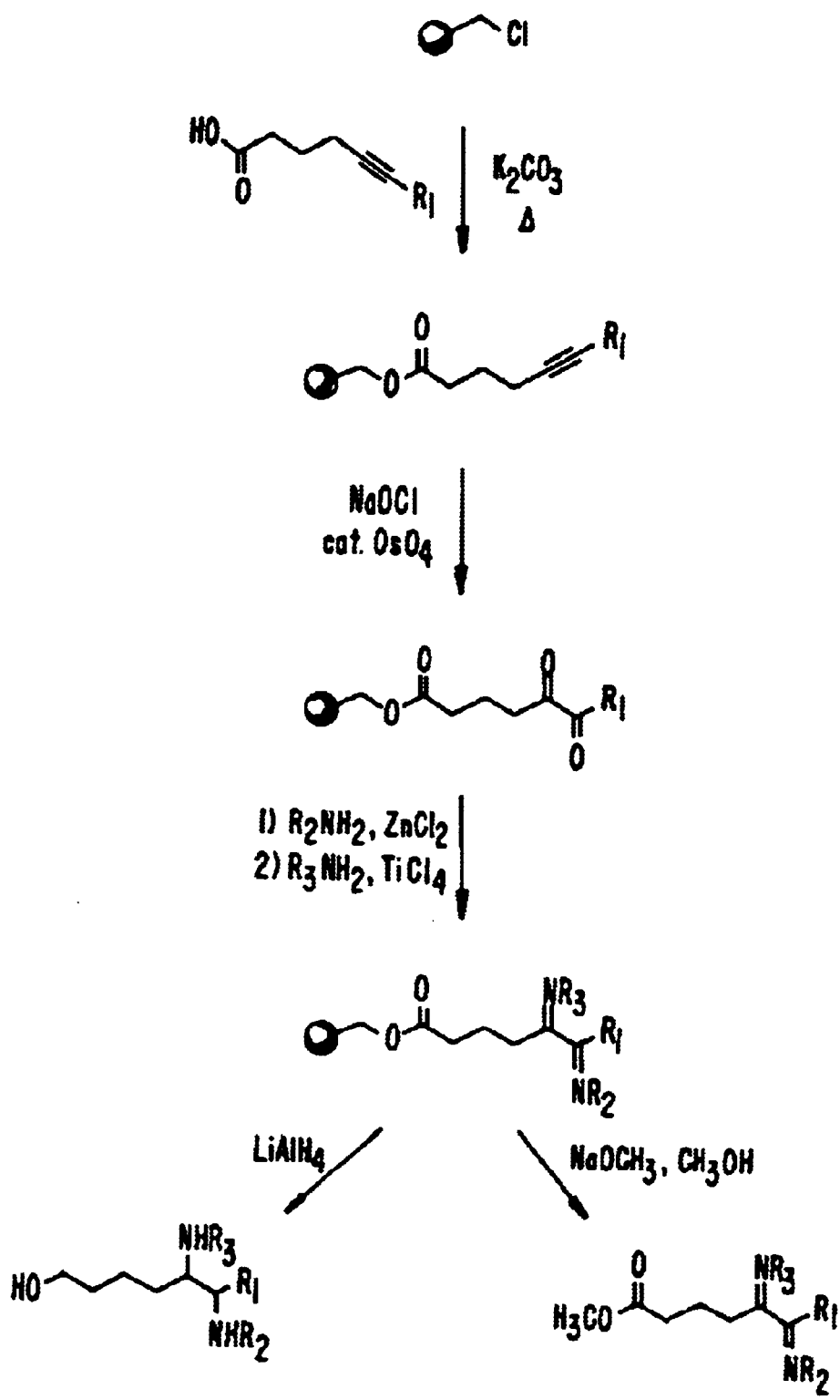

I. Glossary: Abbreviations and Definitions
II. Assembly of Combinatorial Libraries
   A. General Overview
   B. Synthesis Supports and Substrates
   C. Ligands
   D. Linkers
   E. Metals
   F. Immobilized Reagents
   G. Non-coordinating Anions (NCA)
   H. Diimine Catalyst Library Design and Synthesis
III. Screening of Combinatorial Libraries
   A. Introduction
   B. Identification and Characterization of Gas Phase Products or Volatile Components of the Condensed Phase Products
      1. Gas Phase Characterization by Mass Spectroscopy
         (i) Differentially Pumped Mass Spectrometer that Samples Product Stream or Volume Surrounding the Library Compound
         (ii) Supersonic Molecular Beam Sampling System
         (iii) Single Stage Differentially Pumped Mass Spectrometer
         (iv) Individual Flow-Through Library Sampling
         (v) Differentially Pumped Mass Spectrometer with a Simplified Flow System
         (vi) Embedded Catalyst Impregnated in Micro-porous Silica Capped by Macro-porous Silica
      2. Gas Phase Characterization by Optical Spectroscopy:
         (i) Ultraviolet and Visible Emission- Excitation Spectroscopy
         (ii) Scanning Multi-Wave Mixing Fluorescence Imaging
      3. Gas Phase Characterization by Gas Chromatography:
         (i) Gas Chromatography
   C. Characterization of Condensed Phase Products
      1. Condensed Phase Product Characterization by Optical Methods
         (i) Infrared Absorption
         (ii) Photon Scattering Analysis
         (iii) Polarized Light Imaging
      2. Condensed Phase Product Characterization by Mechanical Properties
         (i) Ultrasonic Monitoring
   D. Measurement of Physical Properties of the Catalyst Library Characterization by Heat of Reaction
         (i) Two-dimensional Infrared Imaging for Parallel Monitoring of Catalyst Library Heat of Reaction
IV. EXAMPLES

I. Glossary: Abbreviations and Definitions

Abbreviations and generalized chemical formulae used herein have the following meanings: Cp, η5-cyclopentadienyl; Cp*, η5-pentamethylcyclopentadienyl; MAO, methylaluminoxane; [Q]$^+$[NCA]$^-$, reactive cation/non-coordinating anion compound; EDG, electron-donating group; EWG, electron-withdrawing group; DME, dimethoxyethane; PEG, poly(ethyleneglycol); DEAD, diethylazodicarboxylate; COD, cyclooctadiene; DBU, 1,8-diazabicyclo[5.4.0]undec-7-ene; FMOC, 9-fluorenylmethoxycarbonyl; HOBT, 1-hydroxybenzotriazole; BTU, O-benzotriazole-N,N,N',N'-tetramethyl-uronium-hexafluorophosphate; DIAD, diisopropylazodicarboxylate. Other abbreviations and chemical formulae used herein have the meaning normally assigned to them by those of skill in the art.

Catalyst: As used herein, the term "catalyst" refers to a compound which speeds a chemical reaction or causes it to occur. The catalysts of the present invention are formally organometallic compounds. Certain of the organometallic compounds of the invention will require "activation" prior to being catalytically active. Other organometallic compounds of the invention will be "activator-free catalysts" and will not require activation prior to being catalytically active.

Ligand: Organometallic compounds are conventionally formulated as comprising a central metal atom or ion surrounded by and bonded to other atoms, ions, or small molecules known as "ligands". Ligands are either organic (e.g., $\eta^1$-aryl, alkenyl, alkynyl, cyclopentadienyl, CO, alkylidene, carbene) or inorganic (e.g., Br$^-$, Cl$^-$, OH$^-$, NO$^{2-}$, etc.), and can be charged or neutral. The number of times an inorganic or organic moiety occurs as a ligand in a metallic complex is generally indicated by the prefixes di, tri, tetra, etc. Multiple occurrences of complex organic ligands are indicated by the prefixes bis, tris, tetrakis, etc.

As used herein, the term "ancillary ligand" is distinguished from a "leaving group ligand." An ancillary ligand will remain associated with the metal center(s) as an integral constituent of the catalyst or organometallic compound. Ancillary ligands are defined according to the number of coordination sites they occupy and their formal charge. A leaving group ligand is a ligand which is replaced in a ligand substitution reaction. A leaving group ligand can be replaced with an ancillary ligand or an activator component.

In most cases, the formalisms for assigning the charge on the ligand and the number of coordination sites it occupies are easily established and unambiguous. As with most chemical formalisms, there are examples where these assignments are subject to interpretation and debate. Such is the case with the η5 cyclopentadienyl (Cp) ligand which is considered to occupy 3 or 1 coordination site(s) on the metal, depending on the overall symmetry about the metal center. When the symmetry of the metal complex is best described as octahedral, the Cp-ligand will be assigned to occupy 3-coordination sites (on face of the octahedron). If, however, the metal complex symmetry is best described as tetrahedral, square planar or trigonal, the Cp-ligand is considered to occupy 1-coordination site. For the purposes of this invention, the Cp-ligand will formally be considered to occupy 1-coordination site on the metal complex.

Activator: In general, activators are used in the synthesis of various catalysts. Activators render a metallic center active as a catalyst and can be, for example, a chemical or an energy source which renders a metal center active and which, in certain embodiments, is directed from a source to a catalyst precursor which is located at a defined region on a substrate.

In certain embodiments wherein an activator is a chemical reagent which converts a metal complex into an olefin polymerization catalyst, the activator will generally fall into one of two broad classes of agents: (1) alkylating agents; and (2) ionizing agents.

"Alkylating agents," as used herein, define agents which function by exchanging unreactive ligands, such as, for example, halide or alkoxide, for reactive σ-bonded alkyl groups, such as, for example, methyl or ethyl groups. An example of this type of activation is illustrated by the conversion of $Cp_2*ScCl$ into $Cp_2*ScMe$ (where $Cp*=\eta_5-C_5Me_5$) using methyllithium. In general, activation by alkylation works in systems where the metal center of the catalyst precursor is highly coordinatively unsaturated and does not require further reduction of coordination number to function as a catalyst; however, this mode of activation is not limited to such metal centers.

"Ionizing agents" function as activators by reducing the coordination number of the transition metal precursor by at least one coordination site to form ionic products. There are two types of ionizing agents: (1) Lewis acids; and (2) ion-exchange activators.

"Lewis acids" function by abstracting a leaving group ligand from the metal center to form a compatible non-coordinating anion ("NCA" which is comprised of the leaving group ligand and the Lewis acid) and a coordinatively unsaturated active transition metal cation. "Ion-exchange activators" deliver to the catalyst precursor a preformed compatible non-coordinating anion and accept from the catalyst precursor a coordinating anion (such as a methyl or halide group). Ion-exchange activators have the general formula $Q^+NCA^-$, wherein $Q^+$ is a reactive cation and NCAT is a compatible non-coordinating anion. The Lewis acids and ion exchange activators of use with the present invention include both soluble and supported (e.g., silica resin bound) Lewis acids and ion exchangers.

In some cases, activation can also be accomplished by Lewis acid or ion-exchange agents. For example, consider two possible chemical pathways leading to the synthesis of the catalyst, $[Cp_2ZrCH_3]^+[B(C_6F_5)_3CH_3]^-$, where $[B(C_6F_5)_3CH_3]$ is the "compatible non-coordinating anion" or "counter-ion". Using the Lewis acid pathway, the catalyst precursor is $[Cp_2Zr(CH_3)]$ and the activator is $[B(C_6F_5)_3]$. Using the "ion-exchange" pathway, the catalyst precursor is $[Cp_2Zr(CH_3)_2]$ and the activator is $[Ph_3C]^+[B(C_6F_5)_3CH_3]^-$. These examples demonstrate that all or part of the activator can become the "non-coordinating anion" or "counterion."

Compatible non-coordinating anion: A compatible non-coordinating anion is an anion that either does not coordinate to the metal cation, or is only weakly coordinated to the metal cation such that it remains sufficiently labile to be displaced by a neutral Lewis base or the molecule being transformed in the catalytic cycle. The term "compatible non-coordinating anion" specifically refers to an anion which when functioning as a stabilizing anion in the catalyst system of this invention does not transfer an anionic fragment to the metal cation to form inactive neutral products.

Organometallic compounds: Classically, compounds having bonds between one or more metal atoms and one or more carbon atoms of an organic group are defined as "organometallic compounds". For the purposes of this application, "organometallic" is defined to include all ancillary ligand stabilized metallic complexes regardless of presence or absence of a metal-carbon bond. As used herein, "organometallic compounds" are distinguished from catalysts by their lack of useful levels of catalytic activity in an initial screening. This definition does not, however, preclude a compound which was initially identified as an organometallic compound without catalytic activity in reference to a certain class of reactions (e.g., alkene polymerization) but which is later identified as having catalytic activity with a different class of reactions (e.g., alkyne polymerization).

Metallocenes: Organometallic compounds in which a transition metal, such as, for example, zirconium, cobalt or nickel, is bonded to at least one substituted or unsubstituted η5-cyclopentadienyl group.

Substrate: A material having a rigid or semi-rigid surface. In some embodiments, at least one surface of the substrate will be substantially flat. In other embodiments, the substrate will be divided into physically separate synthesis regions. Division of the substrate into physically separate synthesis regions can be achieved with, mu for example, dimples, wells, raised regions, etched trenches, or the like. In still other embodiments, small beads or pellets may be provided on the surface by, for example, placing the beads within dimples, wells or within or upon other regions of the substrate's surface. Alternatively, the small beads or pellets may themselves be the substrate. An appropriate substrate can be made out of any material which is compatible with the processes intended to occur thereon. Such materials include, but are not limited to, organic and inorganic polymers, quartz, glass, silica, etc. The choice of an appropriate substrate for certain given conditions will be apparent to those of skill in the art.

Synthesis support: A material such as, for example, silica, alumina, a resin or controlled pore glass (CPG) which is functionalized to allow a ligand or a ligand component to be attached either reversibly or irreversibly thereto. Specific examples of synthesis supports include Merrifield resin and functionalized silica gel. A synthesis support can be held within or upon a "substrate." "Synthesis support," "support," "bead" and "resin" are used interchangeably herein.

Predefined region: A predefined region is a localized, addressable area on a substrate which can be used for formation of a selected material and is otherwise referred to herein in the alternative as "known" region, "reaction" region, a "selected" region, or simply a "region." The predefined region may have any convenient shape, e.g., circular, rectangular, elliptical, wedge-shaped, etc. Additionally, the predefined region can be a bead or pellet which is coated with a reactant component(s) of interest. In this embodiment, the bead or pellet can be identified with a tag, such as, for example, an etched binary bar code that can be used to indicate the history of the bead or pellet (i.e., to identify which components were deposited thereon). In general, a predefined region is from about 25 $cm^2$ to about 10 $\mu m^2$. In a preferred embodiment, a predefined region and, therefore, the area upon which each distinct material is synthesized is smaller than about 10 $cm^2$. In another preferred embodiment, a predefined region is less than 5 $cm^2$. In a further preferred embodiment, a predefined region is less than 1 $cm^2$. In yet a further preferred embodiment, a predefined region is less than 1 $mm^2$. In still other preferred embodiments, the regions have an area less than about 10,000 $\mu m^2$. In an additional preferred embodiment, the regions are of a size less than 10 $\mu m^2$.

Linker: As used herein, the term "linker" or "linker arm" refers to a moiety interposed between the substrate and the ligand, catalyst or the organometallic compound. Linkers are either cleavable or noncleavable.

Metal ion: As used herein, the term "metal ion" refers to ions which are derived from, for example, simple salts (e.g., $AlCl_3$, $NiCl_2$, etc.), complex or mixed salts comprising both organic and inorganic ligands (e.g., [(ƒ5-C₅Me₅)IrCl₂,]₂, etc.) and metal complexes (e.g., Gd(NTA)₂, CuEDTA, etc.). Metal ions of use in practicing the present invention include, for example, main group metal ions, transition metal ions, lanthanide ions, etc. Zero valent metal precursors, such as Ni(COD)₂, are included in this definition.

II. Assembly of Combinatorial Libraries

A. General Overview

The present invention provides methods, compositions and devices used for the combinatorial synthesis, screening and characterization of supported and unsupported organometallic compounds and ancillary ligand-stabilized catalysts (e.g., homogeneous and heterogenous catalysts) and libraries thereof. Preferably, the synthesis and screening of such libraries is carried out in a spatially selective, simultaneous, parallel or rapid serial fashion. In the embodiment wherein the library synthesis is carried out in parallel, a parallel reactor is preferably employed. The illustrations herein provide the first methods for generating and screening combinatorial libraries of organometallic compounds and catalysts.

The methods of the present invention provide for the assembly of libraries of organometallic compounds and catalysts. The catalysts of the present invention are either of a type which requires activation by an activating agent or, alternatively, they are activator-free catalysts. The invention also provides methods for the synthesis of both supported and unsupported organometallic compounds and catalysts. When the library compounds are supported, they are either attached to a substrate or, alternatively, to an intermediate synthesis support which is itself optionally on or within a substrate. Supported library compounds are bound to the substrate or synthesis support either directly through a functional group attached to a ligand core or, alternatively, through a linker arm which is itself a ligand core or pendent from a ligand core. When the library comprises catalysts, the library can be assembled such that the catalysts are homogeneous, heterogenous or a mixture thereof.

Thus, in one aspect the present invention provides a method of making an array of metal-ligand compounds, the method comprising:

(a) synthesizing a first metal-binding ligand and a second metal-binding ligand on first and second regions of a substrate;

(b) delivering a first metal ion to the first metal-binding ligand and a second metal ion to the second metal-binding ligand to form first and second metal-ligand compounds.

In this embodiment, ligands are assembled on the substrate by the step-wise delivery of ligand fragments and the reagents necessary to couple those fragments. Once the ligands are synthesized, they are reacted with metal ions to form metal-ligand compounds.

In another aspect, the invention provides a method for immobilizing intact ligands on a substrate by binding the ligands to reactive groups on the surface of the substrate. Thus, in this aspect, the invention is a method for making an array of metal-ligand compounds, the method comprising:

(a) delivering a first metal-binding ligand and a second metal-binding ligand on first and second regions of a substrate;

(b) delivering a first metal ion to the first metal-binding ligand and a second metal ion to the second metal-binding ligand to form a first metal-ligand compound and a second metal ligand compound.

In another embodiment, the metal-ligand compounds thus synthesized are reacted with an activating agent. Preferred activators include, but are not limited to, Lewis acids, such as B(C₆F₅)₃ and MAO, and ion-exchange reagents of the form [Q]⁺[NCA]⁻, such as [H(OEt)₂]⁺[BAr₄]⁻ and [H(OEt₂)]⁺[B (C₆P₅)₄]. In a still further preferred embodiment, the activators are independently selected for each member of the library. In another preferred embodiment, the activated metal-ligand compounds comprise olefin polymerization catalysts. In a further preferred embodiment, the catalysts are activator-free catalysts.

In another aspect, the invention provides a method of making and screening an array of metal-ligand compounds, the method comprising:

(a) synthesizing a spatially segregated array of ligands;

(b) delivering a suitable metal precursor to each element of said array of ligands to create an array of metal-ligand compounds;

(c) optionally activating said array of organometallic complexes with an activator (e.g., a suitable cocatalyst);

(d) optionally modifying said array of metal-ligand compounds with a third component; and (e) screening said array of metal-ligand compounds for a useful property using a parallel or serial rapid screening technique selected from the group consisting of optical imaging, optical spectroscopy, mass spectrometry, chromatography, acoustic imaging, acoustical spectroscopy, infrared imaging, and infrared spectroscopy.

Numerous types of ligands are of use in practicing the present invention (see, FIGS. 1–13). In a preferred embodiment, the ligands are neutral bidentate ligands. In another preferred embodiment, the ligands are monoanionic bidentate ligands. In yet another preferred embodiment, the ligands are chelating diimine ligands. In still another preferred embodiment, the ligands are salen ligands. Preferred ligands have a coordination number which is independently selected from the group consisting of 1, 2, 3 arid 4. These preferred ligands have a charge which is independently selected from the group consisting of 0, −1, −2, −3 and −4. Certain preferred ligands have a charge which is greater than their coordination number.

The ligands are either attached directly or through a linker group to a substrate or a synthesis support or, alternatively, they are in solution. In a preferred embodiment, the ligands are attached directly to a synthesis support. In another preferred embodiment, the ligands are attached to a synthesis support through a linker group. In a further preferred embodiment, the ligands are attached to a substrate either directly or through a linker.

Any of the functional groups on the ligands or the linkers, or components of the ligands or the linkers, can be protected to avoid interference with the coupling reactions. The protection can be achieved by standard methods or variations thereof. A plethora of protection schemes for most known functional groups are known to and used by those of skill in the art. See, for example, Greene, T., et al., PROTECTIVE GROUPS IN ORGANIC SYNTHESIS, Second Ed., John Wiley and Sons, New York, 1991, the teachings of which are herein incorporated by reference.

The chemical synthesis steps can be conducted using solid-phase, solution-phase or a combination of solid-phase and solution-phase synthetic techniques.

The ligand, metal, activator, counterion, substrate, synthesis support, linker to the substrate or synthesis support and additives can be varied as part of the library. The various elements of the library are typically varied by, for example, the parallel dispensing of reagents to spatially addressable sites or by known "split-and-pool" combinatorial methodology. Other techniques for assembling combinatorial libraries will be apparent to those of skill in the art. See, for example, Thompson, L. A., et al., "Synthesis and Applications of Small Molecule Libraries," *Chem. Rev.* 1996, 96:555–600, and references therein which are herein incorporated by reference.

Any number of a wide range of metal ions are appropriate for use in the present invention. In a preferred embodiment, the metal ions are transition metal ions. In another preferred embodiment, the metal ions are ions of Pd, Ni, Pt, Ir, Rh, Co, Cr, Mo and W. When the metal ion is a transition metal ion, in one preferred embodiment, the metal-binding ligands are neutral bidentate ligands and the transition metal ion is stabilized by a labile Lewis base in the metal precursor. In another preferred embodiment, the ligands are monoanionic bidentate ligands and the transition metal center is stabilized by a labile anionic leaving group ligand in the metal precursor. In a still further preferred embodiment, the ligands are [2,2] or [2,1] ligands and each of the ligands is contacted with a main group metal alkyl complex such that the ligands are in the mono- or di-protic form. A particularly preferred metal alkyl complex is a trialkylaluminum complex. In a particularly preferred embodiment, the resulting metal-ligand compounds are useful for an organic transformation requiring a Lewis acid site such as, for example, stereoselective coupling reactions, olefin oligomerization reactions and olefin polymerization reactions. In yet another preferred embodiment, the aluminum-ligand compounds are further modified with an ion-exchange activator to produce an array of ligand-stabilized cationic aluminum compounds. A preferred ion-exchange activator is $[PhNMe_2H][B(C_6F_5)_4]$.

The catalysts prepared using the methods of the invention can be useful for catalyzing a wide variety of reactions including, but not limited to, oxidation, reduction, hydrogenation, hydrosilation, hydrocyanation, polymerizations (e.g., olefins and acetylenes), water gas shift, oxo reaction, carboalkoxylation of olefins, carbonylation reactions (e.g., of acetylenes and alcohols, etc.), decarbonylation, etc.

As explained in greater detail hereinbelow, following the synthesis of the library, the library compounds are screened for a useful property. In a preferred embodiment, the useful property is a property relating to a polymerization reaction. In another preferred embodiment, the useful property is a mechanical property, an optical property, a physical property or a morphological property. In certain preferred embodiments, the useful property is a chemical property such as, for example, the lifetime of the metal-ligand compounds, the stability of these compounds under specific reaction conditions, the selectivity of the library compounds for a particular reaction, the conversion efficiency of the library compounds in a particular reaction or the activity of the library compounds in a particular reaction. The library can be screened for compounds with useful properties using a wide range of techniques. Thus, in one preferred embodiment, the screening is performed by a method chosen from the group consisting of scanned mass spectrometry, chromatography, ultraviolet imaging, visible imaging, infrared imaging, electromagnetic imaging, ultraviolet spectroscopy, visible spectroscopy, infrared spectroscopy, electromagnetic spectroscopy and acoustic methods.

In general, the analysis of catalysts and organometallic compounds requires the ability to rapidly characterize each member to identify compounds with specific, desired properties. An exemplary use of the present invention is in the discovery and optimization of new catalysts. In a preferred embodiment wherein catalysts are synthesized, the constituents of the combinatorial library will be analyzed using high throughput methods for measuring such properties as activity (i.e. turnover), selectivity in converting reactants into desired products, and stability during operation under a wide variety of substrate concentrations and reaction conditions. Spatially selective characterization methods include, for example, those capable of: (i) identification and characterization of gas phase products and volatile components of the condensed phase products; (ii) identification and characterization of condensed phase products; and (iii) measurement of physical properties of the catalyst elements on the library. Similar high throughput methodologies can be used for measuring properties other than catalysis (e.g., target binding, solubility, hydrophilicity, etc.) of libraries of both organometallic compounds and catalysts.

In yet another aspect, the invention comprises an array of between 10 and $10^6$ different metal-ligand compounds at known locations on the substrate. In certain embodiments, the array will comprise more than 50 different metal-ligand compounds at known locations on the substrate. In other embodiments, the array will comprise more than 100 or more than 500 different metal-ligand compounds. In still further embodiments, the array will comprise more than 1,000, more than 10,000 or more than $10^6$ different metal-ligand compounds at known locations on the substrate.

The assembly of combinatorial libraries of organometallic compounds and catalysts allows the rapid assessment of the effects of changes in numerous characteristics of the compounds themselves, the reactions used to prepare the compounds and the reactions in which the compounds take part. Examples of characteristics and properties (together referred to herein as "parameters") which can be modified include, but are not limited to, the identity of the ligand core itself, substituents on the ligand core, identity and/or charge of the metal ion, counterion, activator, reaction conditions, solvents, additives, supports, substrates and linkers. Other parameters of interest whose effects can be investigated by the use of the methods of the present invention will be apparent to those of skill in the art.

In a preferred embodiment of the present invention, only one parameter is varied per addressable location. In another preferred embodiment, the compounds synthesized are catalysts and variations in the various parameters are used to identify optimal species and conditions for catalyzing, or otherwise carrying out, a desired reaction or class of reactions.

Combinatorial libraries can be used in the synthesis of both organometallic compounds and catalysts to identify the optimal metal ion, metal ion charge, geometry and/or coordination number for achieving a property of interest. Similarly, the library can be used to measure the effects of changes in counterions, activators, reaction conditions, solvents and additives. Properties of the library constituents which are of interest include, for example, catalytic parameters, solubility, conductivity, hydrophilicity, mechanical properties and general pharmacological parameters (e.g., target binding, pharmacokinetics, distribution volume, clearance, etc.).

A specific example of a type of compound which can be synthesized and analyzed in a combinatorial format are the diimine Ni and Pd complexes discovered by Brookhart. This family of catalysts comprises 1,2 diimine ligand moieties bound to either 4-coordinate $Ni^{2+}$ or $Pd^{2+}$ centers. These precursors are then activated with a Lewis acid, such as MAO, and ion-exchange reagents of the form $[Q]^+[NCA]^-$, such as $[H(OEt)_2]^+[BAr_4]^-$ and $[H(OEt_2)]^+[B(C_6F_5)_4]^-$, etc., to form polymerization catalysts. The properties of the catalyst (e.g., polymer molecular weight capability, polymer branching statistics, etc.) are dependent upon the choice of the constituents of the catalyst. The use of combinatorial libraries allows for the optimization of the nature of these constituents.

Combinatorial libraries can also be used to identify the optimal means of attaching an organometallic compound or a catalyst to a substrate or support (silicate, aluminate, polystyrene, etc.). The catalysts or organometallic compounds are attached to the substrate or synthesis support directly through a functional group on a ligand or, alternatively, through a linker arm. Linker arm parameters which can be varied over a library include, for example, length, charge, solubility, conformational lability and chemical composition. Substituents of these linkers can be varied and particular combinations of catalysts, linkers, synthesis supports, metals, polymerization conditions, etc. can then be assayed directly for optimal catalytic activity and process operability using a two-dimensional or three-dimensional array format or with bead supports.

Optimization of compound constituents such as the metal ion, counterion, activator identity and concentration, etc. is accomplished by varying the identity or concentration of the constituent whose effect on the compound produced is being examined. Typically, the parameter will be varied over the array of addressable locations comprising the library. In addition to the above-described constituents, the nature of the substrate can also be varied using a combinatorial strategy.

The effect(s) of altering the characteristics of the constituents of a combinatorial library can be analyzed either directly or indirectly. Thus, in one embodiment, the structure or properties of the library compounds themselves are studied. In another embodiment, the effect of the library compounds on another molecule or system is studied. For example, when a library of polymerization catalysts is synthesized, the effect of variations in constituents over the library can be assessed by analyzing the polymer products produced using the constituents of the catalyst library. Such analysis can examine catalyst characteristics including, for example, molecular weight capability, copolymerization capability, lifetime, comonomer compatibility, chemical stability, and ability to form polymers of differing topology, molecular weight distribution and/or microstructure. Other means of analyzing combinatorial libraries will be apparent to those of skill in the art.

Libraries can be synthesized on diverse substrates made of different materials or having different topological characteristics and the effect of the nature of the support on the compounds synthesized can be examined as described above. In certain embodiments, the substrate can also comprise a synthesis support.

B. Synthesis Supports and Substrates

In a preferred embodiment, the library comprises an array of supported metal-ligand compounds. In general, if supported organometallic compounds or catalysts are synthesized, the metal-ligand compounds are attached directly to either a substrate or a synthesis support for the library of organometallic compounds or catalysts. In other embodiments, the metal-ligand compounds are attached to the substrate or synthesis support via a linker-arm.

The structure, shape and functional characteristics of the substrate are limited only by the nature and scale of the reactions performed using the substrate. In certain embodiments, the substrate comprises a porous material. In other embodiments, a the substrate is a nonporous material. The substrate can be substantially flat or can contain wells or raised regions. The substrate can have an integral means for liquid transfer such as, for example, holes, needles, valves, pipets or combinations thereof. The substrate can also comprise a means for conducting reactions under an inert or controlled atmosphere. Thus, in one embodiment, the substrate further comprises a cover which has a means for purging the substrate and its contents with a particular atmosphere. In other embodiments, the substrate contains means for heating or irradiating with light, sound or ionizing radiation the materials on or within the substrate. In yet a further embodiment, the substrate comprises a means for agitating the material within or upon the substrate.

In a preferred embodiment, the substrate has a substantially flat upper surface with a plurality of indentations or wells of sufficient depth to allow a quantity of synthesis support to be contained within the indentations or wells during reaction with one or more added reagents.

The substrate is constructed of any material which can be formed into a configuration which allows for the synthesis and screening of the library of the invention. The only limitation upon the materials useful for constructing substrates is that they must be compatible with the reaction conditions to which they will be exposed. Thus, substrates useful in practicing the methods of the invention include, but are not limited to, organic and inorganic polymers, metal oxides (e.g., silica, alumina), mixed metal oxides, metal halides (e.g., magnesium chloride), minerals, quartz, zeolites, TEFLON, crosslinked, noncrosslinked or dentrimeric polyethylene, polypropylene, copolymers, polypropylene, polystyrene, and ceramics. Other configurations for substrates and materials from which substrates can be constructed will be apparent to those of skill in the art. Soluble catalysts can be adsorbed onto inorganic or organic substrates to form useful heterogeneous catalysts.

In an exemplary two-dimensional combinatorial library of supported organometallic compounds or catalysts, wherein a synthesis support is utilized, the following substrate synthesis support configurations are possible: i) a porous support is placed in wells wherein the reactants flow through the support from the top of the well out through a hole in the bottom of the well (or flow may be in the reverse direction); ii) a porous support is placed in wells wherein the reactants flow only into and out of the top of the well; iii) a non-porous support is placed in wells wherein the reactants flow around the substrate from the top of the well out through a hole in the bottom of the well (or flow may be in the reverse direction); iv) a non-porous support is placed in wells wherein the reactants do not flow through from top to bottom of the well, but only to and from the top of the well; or v) a non-porous or porous support that is not contained in wells wherein the reactants are deposited directly onto the substrate surface in a spatially addressable manner.

In embodiments in which a ligand or synthesis support is intended to be attached to the substrate, the substrate is functionalized to allow this attachment. In embodiments wherein the ligand is synthesized by bringing together ligand fragments on the substrate, the substrate is functionalized to allow the attachment of a first ligand fragment. In embodiments wherein the ligand or synthesis support is not bound to the substrate, the substrate can be either functionalized or unfunctionalized.

Functionalizable substrates are known in the art. For example, glass plates have been functionalized to allow the conjugation of oligonucleotides thereto (see, e.g., Southern, *Chem. Abstr.* 1990, 113:152979r). Another method to functionalize glass is taught by Brennan, T. M., et al. (U.S. Pat. No. 5,474,796, herein incorporated by reference), which comprises using polar silanes containing either a hydroxyl or amino group. Organic polymers are also amenable to functionalization. For instance, polypropylene can be surface derivatized by, for example, chromic acid oxidation, and subsequently converted to hydroxy- or amino-methylated surfaces which provide anchors for ligands, ligand fragments or synthesis supports. Other polymers for use in practicing the instant invention include, for example, highly crosslinked polystyrene-divinylbenzene which can be surface derivatized by chloromethylation and subsequent functional group modifications. Nylon surfaces can also be derivatized as they provide an initial surface of hexylamino groups.

Similar to the substrate, the synthesis support can be an organic polymeric material or inorganic material including, but not limited to, alumina, silica, glass quartz, zeolites, TEFLON, etc. Depending on the material the synthesis support is composed of, it can be a porous, textured, or solid material, and may be flat or in the form of beads or any other geometric shape. Synthesis supports comprising, for example, functionalized polystyrene, polyacrylamide and controlled pore glass are known in the art. Jones, J., "AMINO ACID AND PEPTIDE SYNTHESIS," Oxford Science Publications, Oxford, 1992; Narang, S., Ed., "SYNTHESIS AND APPLICATIONS OF DNA AND RNA," Academic Press, Inc., New York, 1987, and references therein which are herein incorporated by reference. Additionally, methods appropriate for functionalizing substrates are also appropriate for functionalizing materials intended for use as synthesis supports. Once the substrate or synthesis support is functionalized, a ligand or ligand component is attached thereto.

C. Ligands

The method of the present invention is broadly applicable to all ligands which are capable of binding metal ions. The combinatorial variation of the ligand can be achieved through a solid-phase or solution-phase reaction or reactions. Alternatively, a sequence comprising a combination of solid-phase and solution-phase reactions can be used to synthesize an array of metal-binding ligands. Ligand characteristics which can be varied using the methods of the present invention include, but are not limited to, the number of coordination sites on the metal which the ligand can occupy, the charge and electronic influence of the ligand, the geometry imposed on the metal by the ligand, the geometry imposed on the ligand by the metal, etc. A plethora of metal-binding ligands are known in the art and other ligands and ligand parameters amenable to variation using the methods of the instant invention will be apparent to those of skill in the art. See, for example, Collman, J. P., et al. PRINCIPLES AN APPLICATIONS OF ORGANOTRANSITION METAL CHEMISTRY, University Science Books, California,. 1987, and references therein which are herein incorporated by reference.

In a preferred embodiment, the general approach is: 1) synthesis of ligand libraries comprising ligands (e.g., ancillary ligands) capable of stabiizing low coordination number (e.g., three to five) metal alkyl complexes in a variety of geometric configurations (e.g., trigonal, tetrahedral, square planar, square pyramidal, pentagonal and bipyramidal); 2) forming metal complexes of these libraries; 3) optionally reacting libraries of the metal complexes with various activators and/or modifiers; and 4) screening the resulting libraries of metal complexes for various properties and characteristics, for example, olefin polymerization activity, polymerization performance characteristics, etc. In an alternative embodiment, the activated metal complexes can be immobilized on a library of supports and/or linkers and then assayed for various properties (e.g., olefin polymerization activity, polymerization performance characteristics). In a particularly preferred embodiment, the metal ion is a transition metal ion.

In a preferred embodiment, the ancillary ligand binds to the metal center and stabilizes it in a low coordination number and does not directly participate in the catalytic chemistry. Although lower numbers of coordination sites are typically preferred, embodiments utilizing larger numbers of coordination sites are not precluded. When the number of coordination sites is three or greater, the metal-ligand compound can have more than one geometry.

In another preferred embodiment, the coordination sites of the ancillary ligand are 1, 2, 3 or 4, and the charge on the ligands are 0, −1, −2, −3 or −4. Other ancillary ligands include those wherein the charge is greater than the number of sites it occupies. Due to the nature of their structure, certain ligands will have more than one possible coordination number and/or more than one possible charge. For example, a ligand's charge and/or coordination number can be different when it is bound to different metals such as an early- or a late-transition metal ion. By way of further example, a ligand which is deprotonated under strongly basic conditions, e.g., n-butyllithium, and contacted with a metal ion can have a different coordination number and/or charge than the same ligand has when reacted with a metal ion under milder conditions.

Examples of ligand, metal-ligand complexes and catalyst families which can be used in the methods of the present invention include, but are not limited to, the following:

(1) One-site, monoanionic ancillary ligands such as $Cp^*MR_2^+NCA^-$ (wherein M represents the metal, R is an alkyl and NCA=non-coordinating anion), and mono-Cp systems in combination with methylalumoxane (MAO);

(2) Two-site, dianionic ancillary ligands, which include, for example, bis-Cp systems (referred to in U.S. Pat. Nos. 4,752,597 and 5,470,927, the teachings of which are incorporated herein by reference); mono-Cp systems where a heteroatom based ancillary ligand occupies the second site (referred to in U.S. Pat. No. 5,064,802, the teachings of which are incorporated herein by reference); non-Cp, bis-amide systems (referred to in U.S. Pat. Nos. 5,318,935 and 5,495,036, the teachings of which are incorporated herein by reference); and bridged bis-amido ligands and Group IV catalysts stabilized by ligands (referred to in *Organometallics* 1995, 14:3154–3156 and *J. Am. Chem. Soc.* 1996, 118:10008–10009, the teachings of which are incorporated herein by reference);

(3) Two site, monoanionic ancillary ligands including, for example, $Cp(L)CoR^+X^-$ and related systems (referred to in WO 96/13529, the teachings of which are incorporated herein by reference);

(4) Two site, neutral ancillary ligands, for example, the $Ni^{2+}$ and $Pd^{2+}$ systems. See, for example, Johnson, et al., *J. Am. Chem. Soc.* 1995, 117:6414–6415 and WO 96/23010, the teachings of which are incorporated herein by reference;

(5) Three site, neutral ancillary ligands;

(6) Three site, monoanionic ancillary ligands;

(7) Three site, dianionic ancillary ligands;

(8) Three site, trianionic ancillary ligands;

(9) Four site, neutral, monoanionic and dianionic ancillary ligands; and

(10) Ancillary ligands where the charge is greater than the number of sites it occupies (see, for example, U.S. Pat.

No. 5,504,049, the teachings of which are incorporated herein by reference).

One application of the present invention is the preparation and screening of large numbers of ligands which are components of organometallic compounds or catalysts. Ligands which are used in practicing the instant invention include as part of their the binding domain of their structural motif groups such as, for example, alkyl, carbene, carbyne, cyanide, olefin, ketone, acetylene, allyl, nitrosyl, diazo, dioxo, disulfur, diseleno, sulfur monoxide, sulfur dioxide, aryl, heterocycles, acyl, carbonyl nitrogen, oxygen, sulfur, phosphine, phosphido and hydride. Additional atoms and groups comprising a metal-binding domain are known in the art and are useful in practicing the instant invention. See, for example, Collman, J. P., et al. PRINCIPLES AND APPLICATIONS OF ORGANOTRANSITION METAL CHEMISTRY, University Science Books, California, 1987, and references therein which are incorporated herein by reference.

As explained above, the libraries of ancillary ligands are made using combinatorial chemistry formats. Within the library, a wide range of ligand characteristics can be varied. Characteristics which are variable across the library include, for example, the ligand's bulk, electronic character, hydrophobicity/hydrophilicity, geometry, chirality, the number of coordination sites on the metal that the ligand occupies, the charge on both the ligand core and its substituents, and the geometry the ligand imposes on the metal.

Bi-, tri- and tetra-dentate ligand systems which lend themselves to combinatorial synthesis can be constructed, for example, from the following ligand fragments which are listed according to their charge.

The synthesis of said ligand libraries can be carried out combinatorially (parallel or split pool methods) using variations of established synthetic organic methods. Neutral ligand fragments include, but are not limited to, amine ($R_3N$), phosphine ($R_3P$), arsine ($R_3As$), stilbines ($R_3Sb$), ethers ($R_2O$), thioethers ($R_2S$), selenoethers ($R_2Se$), teluroethers ($R_2Te$), ketones ($R_2C=O$), thioketones, imines ($R_2C=NR$), phosphinimine ($R_3P=NR$, $RP=NR$, $R_2C=PR$), pyridines, pyrazoles, imidazoles, furans, oxazoles, oxazolines, thiophenes, thiazoles, isoxazoles, isothrazoles, arenes, nitriles ($R-C\equiv N$), isocyanides ($R-N\equiv C$), acetylenes, olefins.

Monoanionic ligand fragments include, but are not limited to, amides ($NR_2$), phosphide ($PR_2$), silyl ($SiR_3$), arsido ($AsR_2$), $SbR_2$, alkoxy ($OR$), thiol ($SR$), selenol ($SeR$), tellurol ($TeR$), siloxy ($OSiR_3$), cyclopentadienyl ($C_5R_5$), boratobenzenes ($C_5BR_6$) pyrazoylborates, carboxylate ($RCO_2^-$), acyl ($RCO$), amidates, alkyl, aryl, triflates ($R_3CSO_3^-$), thiocarboxylate ($RCS_2^-$), halide, nitrate, and the like.

Dianionic ligand fragments include, but are not limited to, cycloctatetrenyl ($R_8C_8^{2-}$), alkylidenes ($R_2C$), borylides ($C_4BR_5$), imido (RN), phosphido (RP), carbolide, oxide, sulfide, sulphate, carbonate, and the like.

Trianionic ligand fragments include, but are not limited to, alkylidynes ($R-C\equiv$), $-P^{3-}$ (phosphides), $-Ar$ (arsides), phosphites.

Multidentate ligands can generally be constructed by bridging ligand fragments through one or more of the pendent R-groups. Specific examples of bidentate neutral ligands [2,0] which may be constructed from the list of ligand fragments set forth above, include, but are not limited to, diimines (derived from two imine fragments), pyridylimines (derived from a pyridine and imine fragment), diamines (derived from two amine fragments), imineamines (derived from an imine and an amine), iminethioether (derived from and imine and a thioether), imineethers (derived from an imine and an ether), iminephosphines (derived from an imine and a phosphine), bisoxazoline (derived from two oxazolines), diethers (derived from two ethers), bisphosphineimines (derived from two phosphineimines), diphosphines (derived from two phosphines) and phosphineamine (derived from a phosphine and amine). Other bidentate neutral ligand systems can be similarly constructed from the list of neutral ligand fragments set forth above.

Bidentate monoanionic ligands [2,1] can be constructed by bridging a neutral ligand fragment with a monoanionic ligand fragment from the lists set forth above. Examples include, but are not limited to, salen and other alkoxy imine ligands (derived from imine and alkoxy ligand fragments), amidoamines (derived from an amide and an amine) and amidoether (derived from an amido and ether). Other bidentate monoamine ligands can be similarly constructed.

Bidentate dianionic ligands [2,2] can be constructed either by combining two monoanionic ligand fragments or a dianionic ligand fragment and a neutral ligand fragment. Specific examples include, but are not limited to, dicyclopentadienyl ligands (derived from two cyclopentadienyl ligand fragments), cyclopentadienyl amido ligands (derived from a cyclopentadienyl and amide ligand fragments), imidothioether ligands (derived from an imido and thioether ligand fragments), imidophosphine ligands (derived from imide and phosphine ligand fragments) and alkoxyamide ligands (derived from alkoxide and amide ligand fragments). Other bidentate diamine ligands can be similarly constructed.

Bidentate ligands having charges greater than −2 can be constructed by combining monoanionic ligand fragments with di- or tri-anionic ligand fragments, or by combining two dianionic ligand fragments. Examples include bisimido ligands (derived from two imide ligands), and carbyne ether ligands (derived from carbyne and ether ligand fragments).

Tridentate neutral ligands [3,0] can be constructed by combining three neutral ligand fragments from the list set forth above. Examples include, but are not limited to, 2,5 diimino pyridyl ligands (derived from two imine and one pyridyl ligand fragments), triimidazoyl phosphines (derived from three imidazole ligand fragments bonded to a central phosphorus atom), tris pyrazoyl alkanes (derived from three pyrazole ligands bonded to a central carbon atom). Other tridentate neutral ligands (e.g., [3,1], [3,2], [3,3]) can be similarly constructed.

In preferred embodiments, the coordination numbers (CN) of the ancillary ligand are independently 1, 2, 3 or 4, and the charge on the ligands are independently 0, −1, −2, −3, or −4. The ancillary ligand or ligand fragment needn't be negatively charged, for example, positively charged ligands, such as, tropylium ($C_7H_7^+$), are also of use in practicing the present invention.

The presently preferred "families" of the coordination numbers and charges are: (i) CN=2, charge=−2; (ii) CN=2, charge=−1; (iii) CN=1, charge=−1; (iv) CN=2, charge neutral; (v) CN=3, charge=−1; (vi) CN=1, charge=−2; (vii) CN=3, charge=−2; (viii) CN=2, charge=−3; (ix) CN=3, charge=−3; (x) CN=3, charge=0; (xi) CN=4, charge=0; (xii) CN=4, charge=−1; and (xiii) CN 4, charge=−2. In other preferred embodiments, the ancillary ligand has a charge which is greater than the number of coordination sites it occupies on a metal ion.

Other preferred embodiments of ligand families that lend themselves to combinatorial synthesis strategies and are depicted herein are: (1) Ancillary ligand on a support wherein, CN=2, charge=neutral, denoted, [2,0]; (2) Ancillary ligand on a support wherein, CN=2, charge=−1, denoted, [2,1]; (3) Ancillary ligand with metal complex on a support wherein, CN=2, charge=−2, denoted, [2,2]; (4) Ancillary ligand off support wherein, CN=2, charge=−1, denoted, [2,1]; (5) Ancillary ligand off support wherein, CN=2, charge=−2, denoted, [2,2]; (6) Ancillary ligand off support with a functional linker, wherein, CN=2, charge=−2, denoted, [2,2]; (7) Ancillary ligand off support with a "functionless" linker, wherein, CN=2, charge=−2, denoted, [2,2]; and (8) Ancillary ligand off support wherein, CN=3, charge=−3, denoted, [3,3].

Figure 3A:
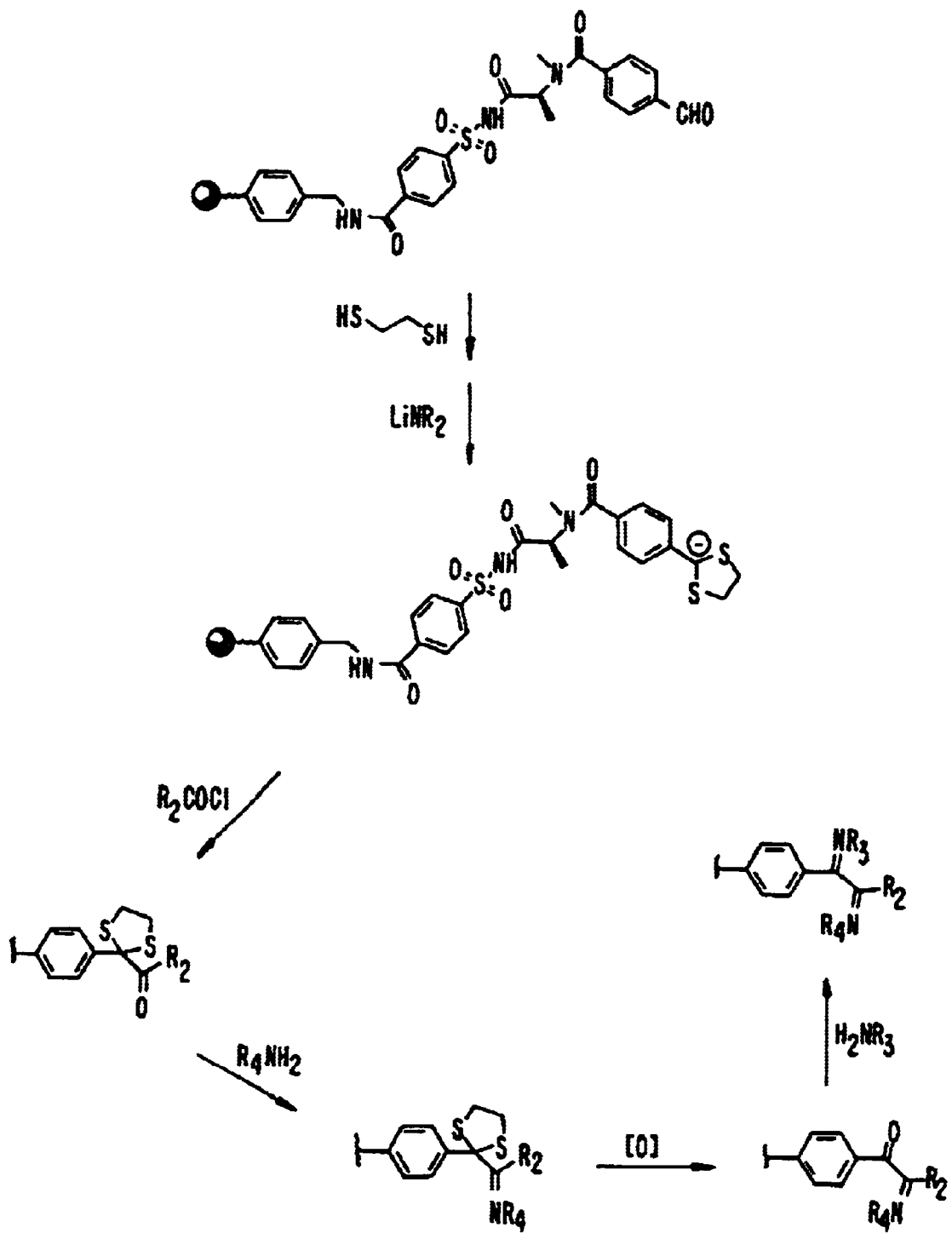
FIGS. 3A and 3B illustrate various combinatorial routes for the synthesis of various ligand types.
Figure 3B:
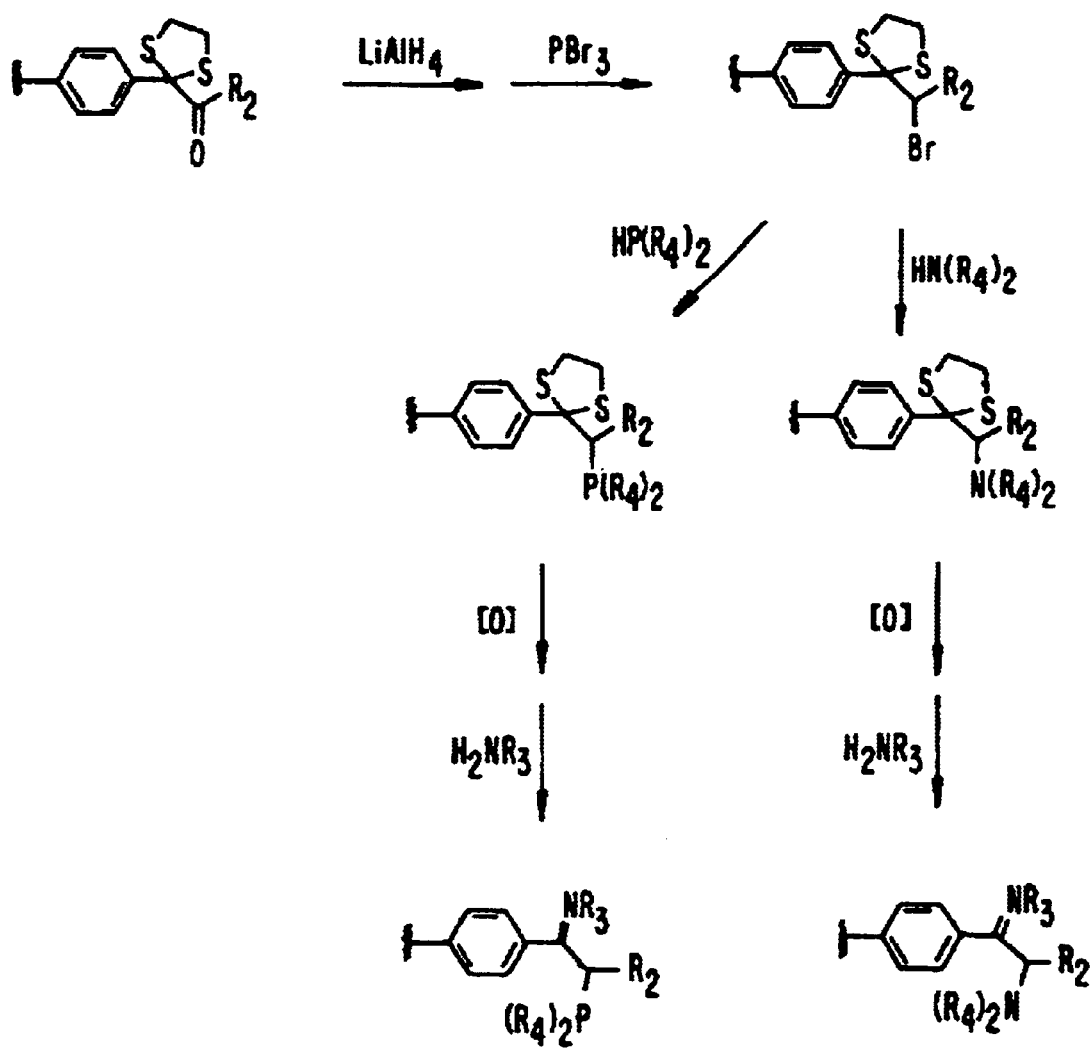
Figure 5:
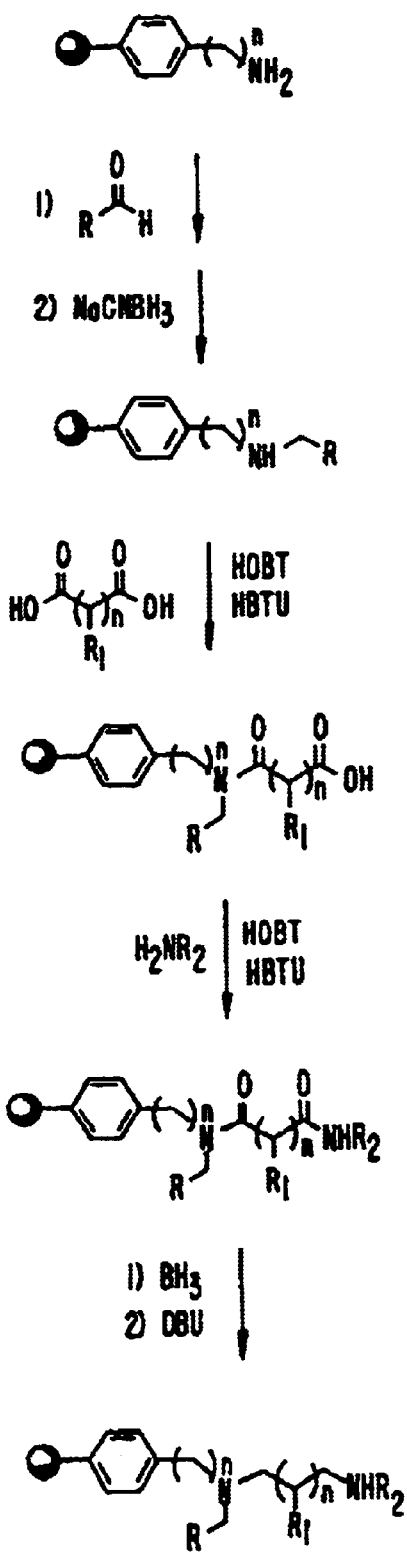
FIG. 5 illustrates a synthesis of an exemplary ancillary ligand on a support, wherein CN=1 or 2, charge=0 or −1.
Figure 6:
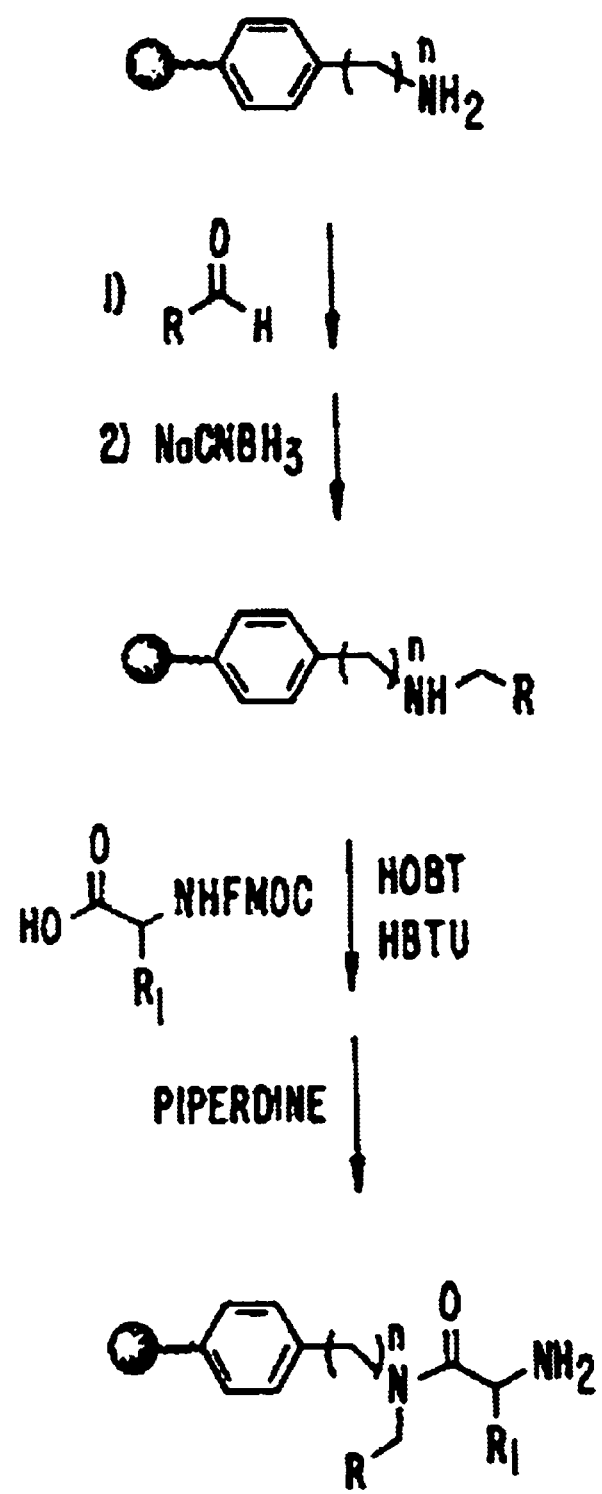
FIG. 6 illustrates a synthesis of an exemplary ancillary ligand on a support, wherein CN=1,2 or 3, charge=0, −1 or −2.
Figure 7:
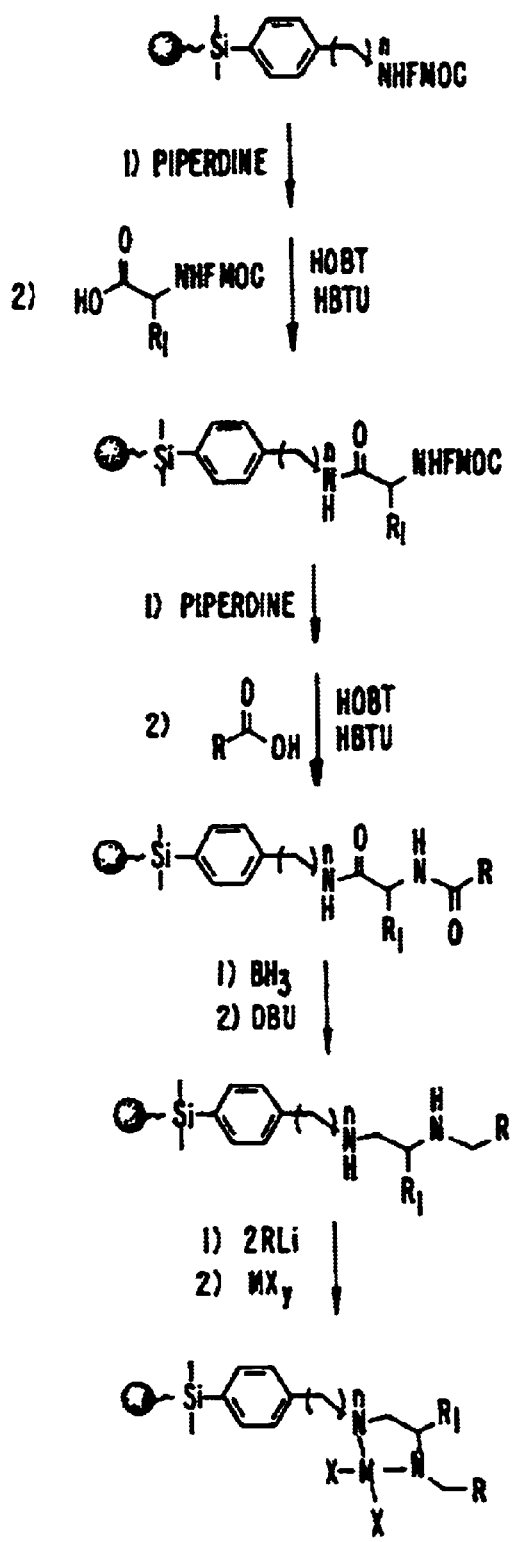
FIG. 7 illustrates a synthesis of an exemplary ancillary ligand with metal complex on a support, wherein CN=2, charge=−2, denoted [2,2].
Figure 8:
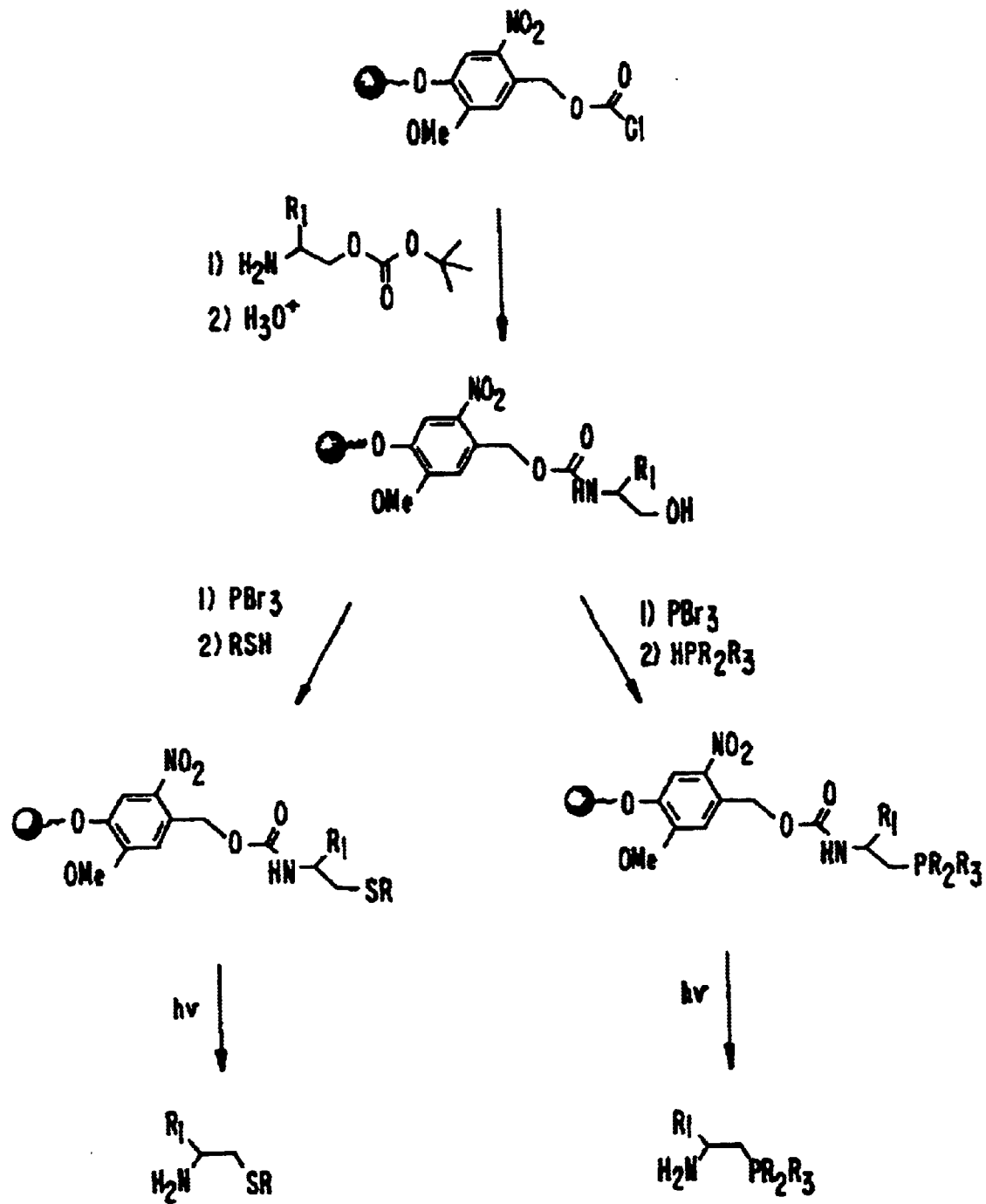
FIG. 8 illustrates the synthesis of two exemplary ancillary ligands off support, wherein CN=2, charge=0, −1 or −2.
Figure 9:
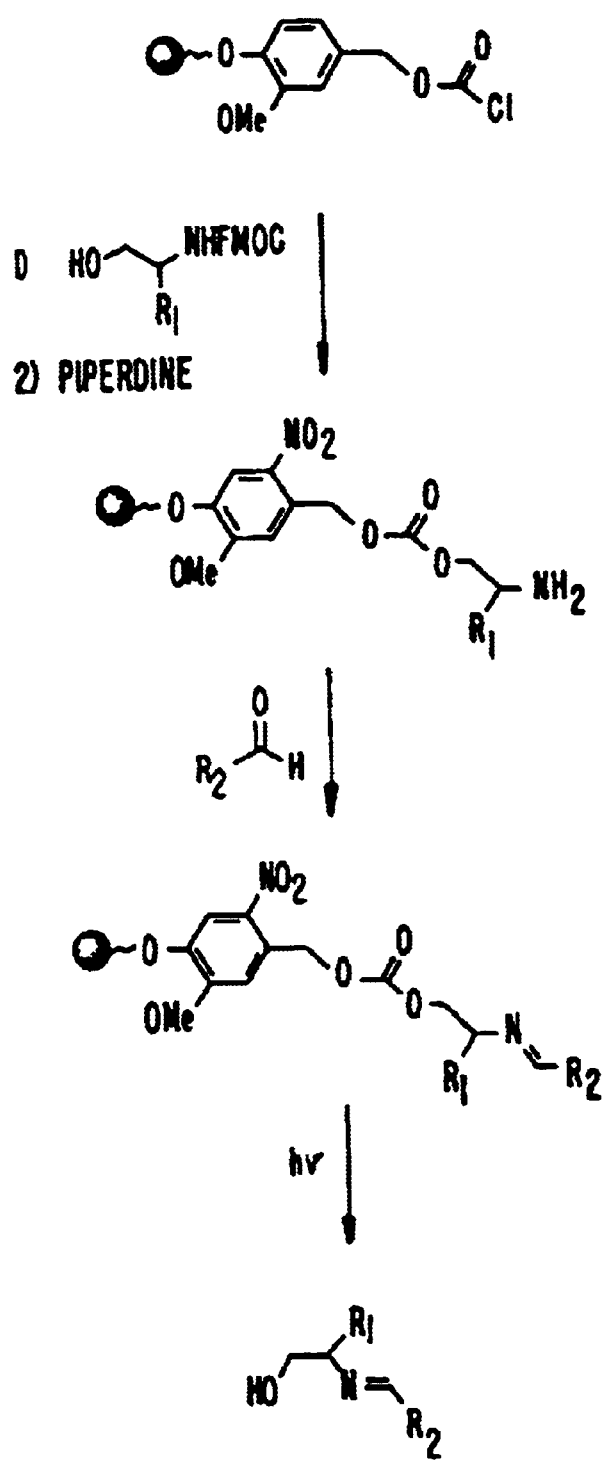
FIG. 9 illustrates a synthesis of an exemplary ancillary ligand off support, wherein CN=2, charge=−1, denoted [2,1].
Figure 10:
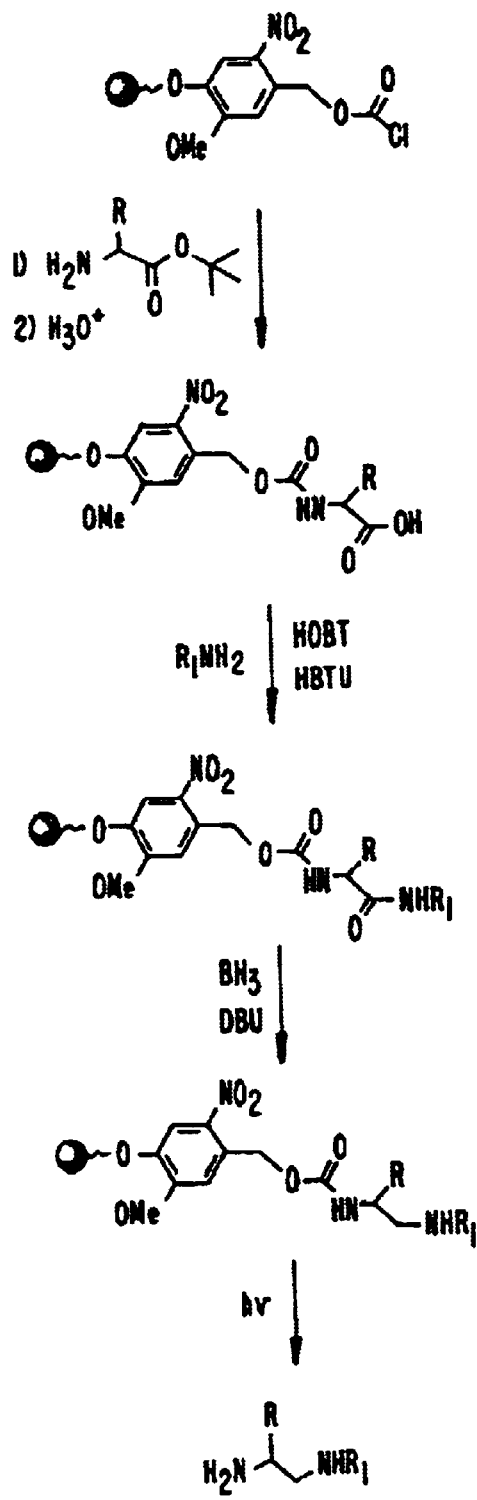
FIG. 10 illustrates a synthesis of an exemplary ancillary ligand off support with a functional linker, wherein CN=2, charge=0, −1, −2 or −3.
Figure 11:
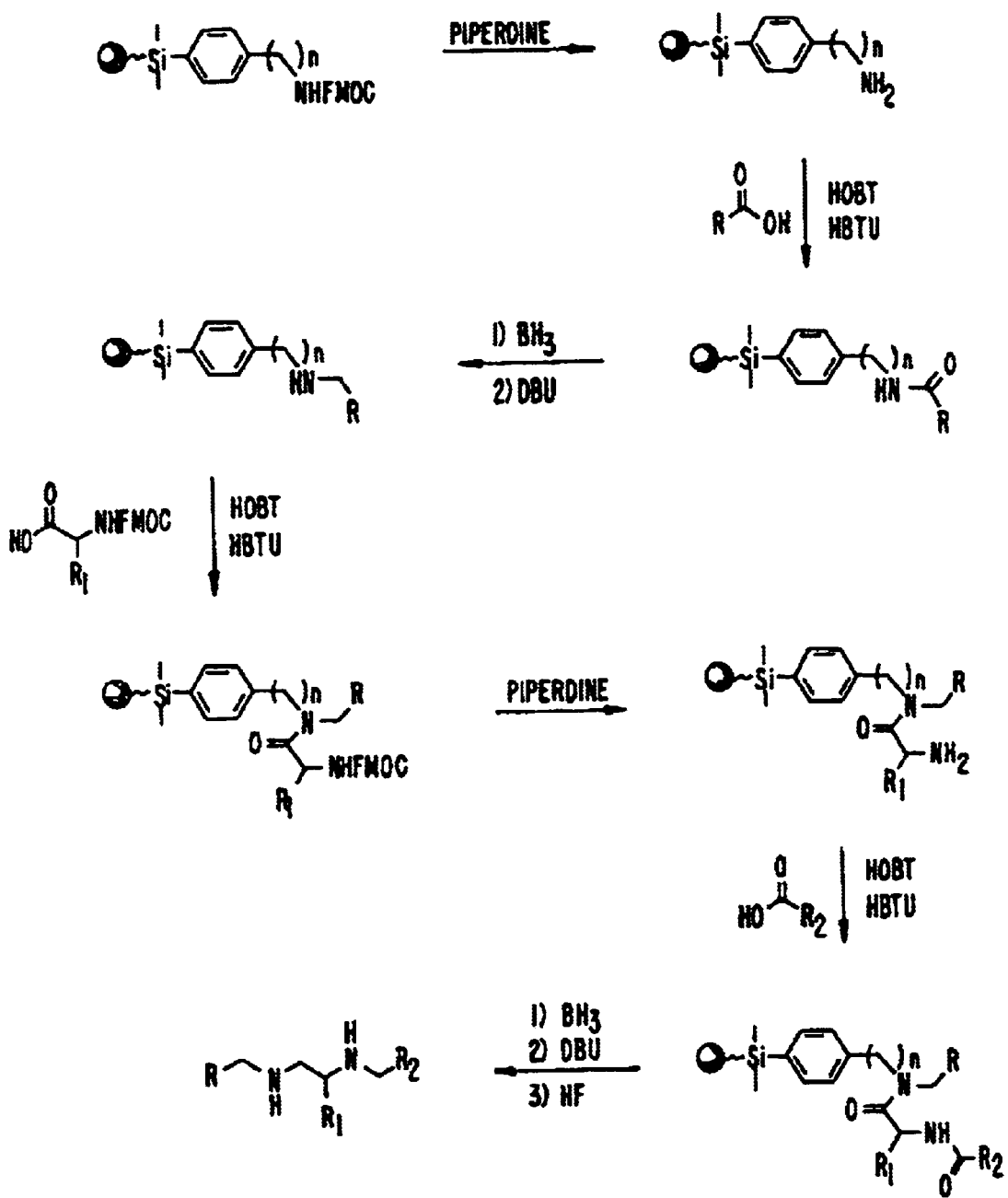
FIG. 11 illustrates a synthesis of an exemplary ancillary ligand off support with a "functionless" linker, wherein CN=2, charge=0, −1 or −2.
Figure 12:
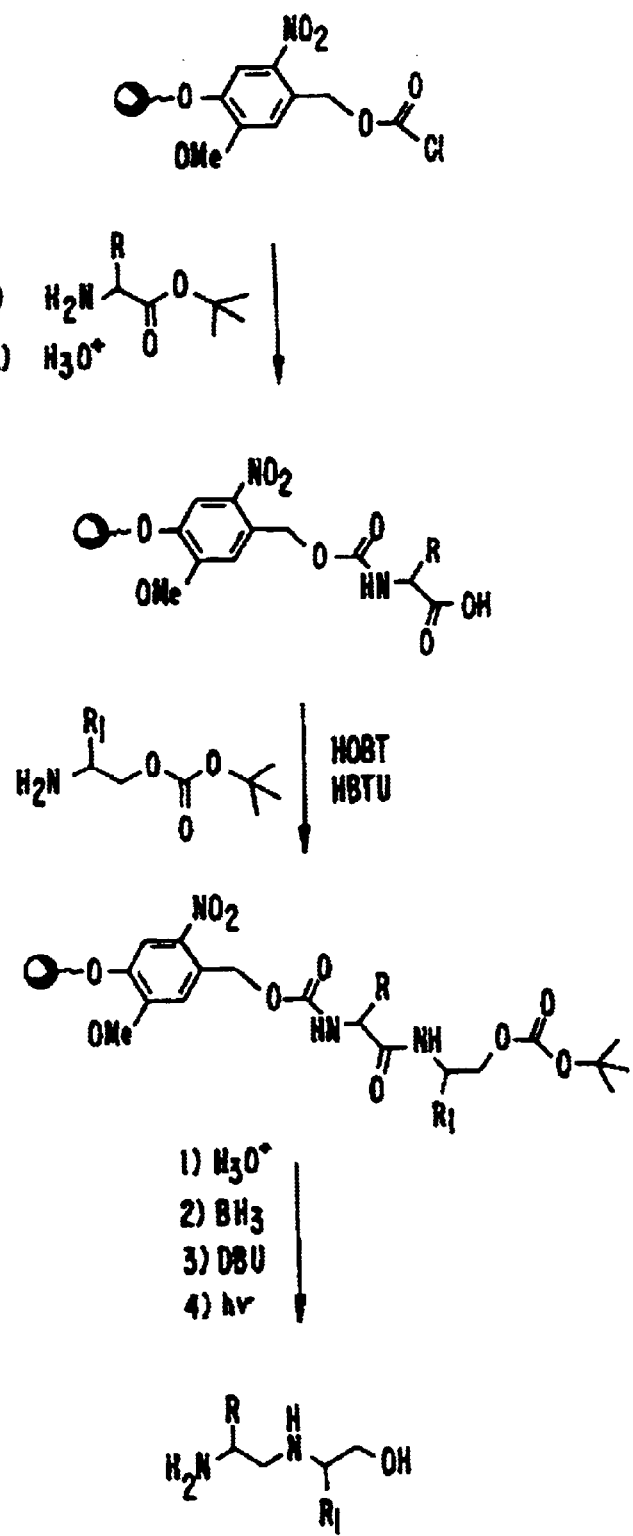
FIG. 12 illustrates a synthesis of an exemplary ancillary ligand off support wherein CN=2 or 3, charge=0, −1, −2, −3 or −4.

FIG. 3 sets forth another possible route for catalyst precursor synthesis L using the combinatorial synthesis approach of the present invention. In general, one can imagine other libraries of ligand cores that can be made using similar combinatorial chemistry formats. Examples include the ligand cores displayed in FIGS. 4A–G.

Figure 13A:
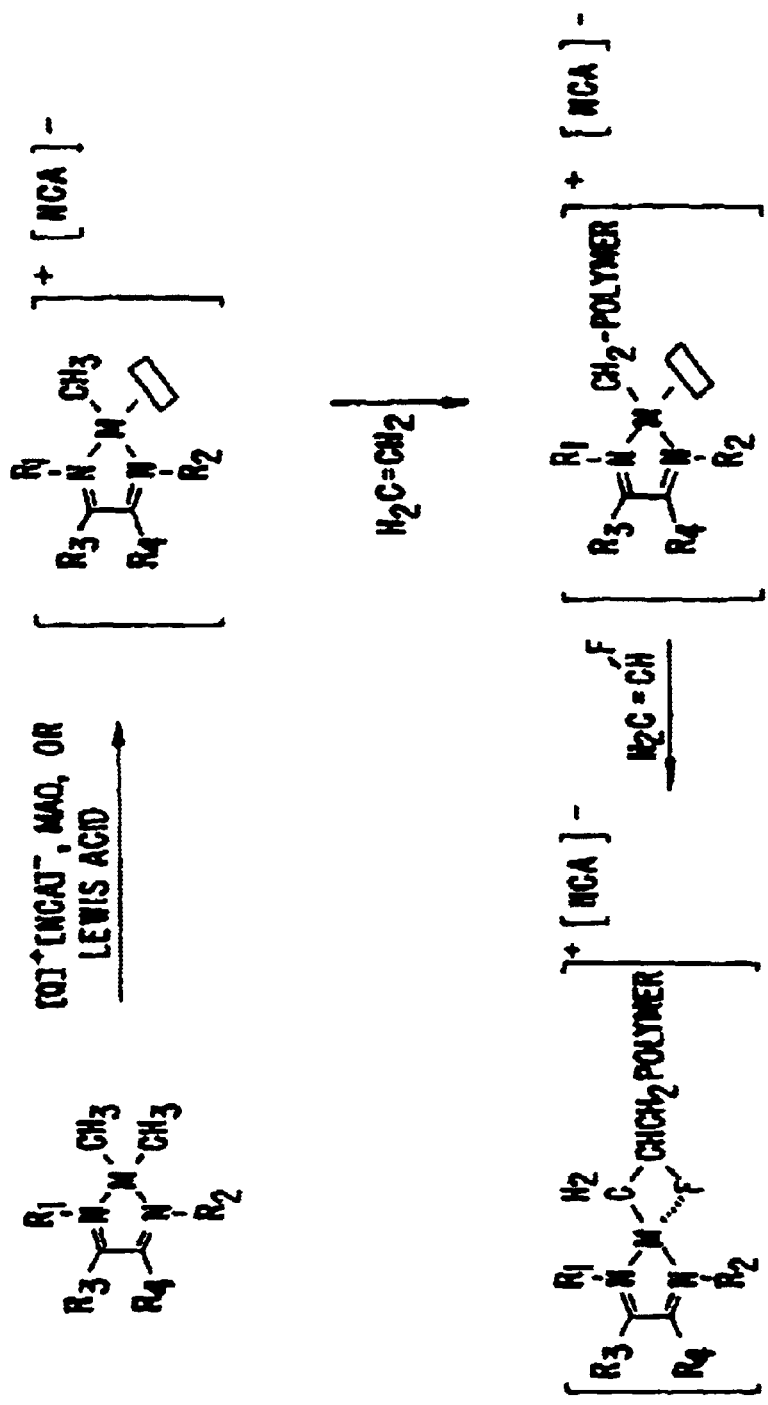
FIGS. 13A and 13B illustrate exemplary synthetic schemes useful in the placement of acidic functionality on the R-group substituents within the array or library.
Figure 13B:
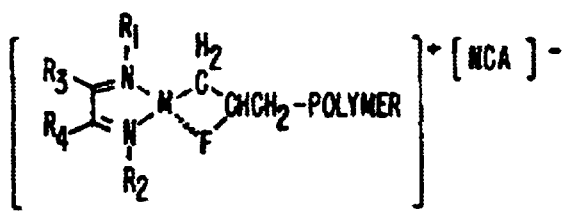
Figure 13B:
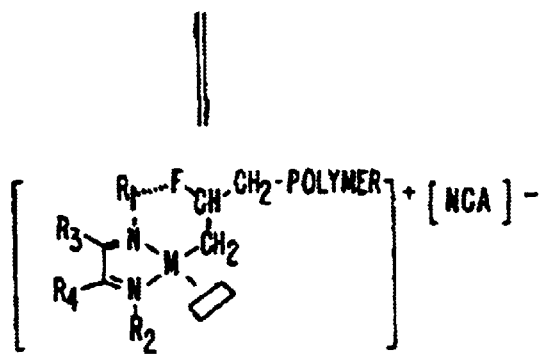
Figure 13B:
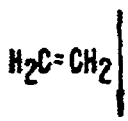
Figure 13B:
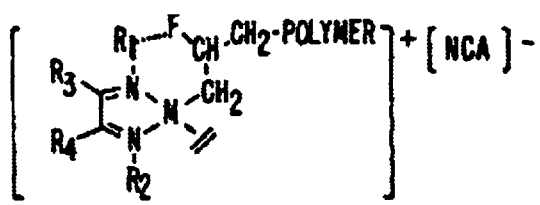
Figure 13B:
Figure 13B:
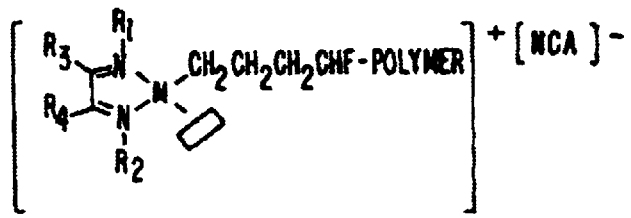

An important example of this invention is the placement of the acidic functionality on the R-group substituents within a library. The acidic functionality can have profound effects on the catalytic performance of the polymerization catalyst system, including improving the ability of the catalyst to rapidly incorporate polar functional comonomers. Late transition metal catalysts, such as the Brookhart catalysts, tolerate certain polar functional comonomers; however, the rate of polymerization is greatly reduced due to intramolecular coordination of the polar functionality to the metal center (see, FIG. 13A). Proper placement of an acidic moiety on the ancillary ligand would compete with the metal center for coordination of the polar functional group and accelerate the rate of polymerization by creating a vacant coordination site at the metal center as depicted in FIG. 13B. Suitable acidic functionalities include, but are not limited to, trivalent boron groups, trivalent aluminum groups, carboxylic acids and sulfuric acids. The inclusion of acidic functionality on the R-groups of the ancillary ligand system is a general concept applicable to all ligand/metal complexes of this invention.

The ligands of the invention, particularly the diimine ligands, can be either symmetric or asymmetric. The symmetric ligands contain two moieties each derived from identical imines. In contrast, the asymmetric ligands will contain two moieties each derived from non-identical amines. A number of synthetic routes can be used to arrive at the asymmetric ligands. For example, one carbonyl group of the diketone can be protected while the other is reacted with an amine. Following deprotection, the second carbonyl group is reacted with a second amine. Another useful reaction pathway consists of adding an approximately stoichiometric amount of a first amine followed by the addition of a similar amount of a second amine. Other routes to both symmetric and asymmetric ligands will be apparent to those of skill in the art.

The R groups pendent from the ancillary core are chosen for the characteristics which they impart to the organometallic compounds. R groups affect the reactivity and stability of catalysts and organometallic compounds but do not bind directly and irreversibly to the metal center. The size and electronic nature of the R groups can be varied to alter the bulk around the metal center and the electronic properties of the ligand-metal compound. R groups which are chiral can impart chirality to the ligand-metal complex. Further R groups are used to adjust the hydrophobicity/hydrophilicity of the ligand-metal compound.

The R groups on the ligands are independently selected from the group consisting of hydrogen, alkyl, substituted alkyl, aryl, substituted aryl, arylalkyl, substituted arylalkyl, acyl, halogen, amino, cyano, nitro, hydroxy, alkoxy, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans.

The term "independently selected" is used herein to indicate that the R groups, e.g., $R_1$, $R_2$ and $R_3$, can be identical or different (e.g., $R_1$, $R_2$ and $R_3$ may all be substituted alkyls or $R_1$ and $R_2$ may be a substituted alkyl and $R_3$ may be an aryl, etc.). Adjacent R-groups may be coupled to form cyclic structures.

A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include substituted or unsubstituted phenyl, naphthyl, biphenyl, diphenylmethyl and benzophenone among others.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group ay also be a carbonyl such as in cyclohexyl phenyl ketone.

The term "acyl" is used to describe a ketone substituent, —C(O)R, where R is alkyl or substituted alkyl, aryl or substituted aryl as defined herein.

The term "amino" is used herein to refer to the group —NRR', where R and R' may independently be hydrogen, lower alkyl, substituted lower alkyl, aryl, substituted aryl or acyl. When an amino group is bonded to a metal through the nitrogen atom, it is referred to as an "amido" ligand.

The term "alkoxy" is used herein to refer to the —OR group, where R is an alkyl, substituted lower alkyl, aryl, substituted aryl, wherein the substituted alkyl, aryl, and substituted aryl groups are as described herein. Suitable alkoxy radicals include, for example, methoxy, ethoxy, phenoxy, substituted phenoxy, benzyloxy, phenethyloxy, t-butoxy, etc.

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures.

The term "unsaturated cyclic hydrocarbon" is used to describe a monovalent nonaromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone.

As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "alkyl" wherein the heteroaryl group is attached through an alkyl group as defined herein.

"Substituted heteroaryl" refers to heteroaryl as just described wherein the heteroaryl nucleus is substituted with one or more functional groups such as lower alkyl, acyl, halogen, alkylhalos (e.g., $CF_3$), hydroxy, amino, alkoxy, alkylamino, acylarnino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted alkyls" as described above in which an alkyl group, as defined herein, links the heteroaryl group to the nucleus.

The term "heterocyclic" is used herein to describe a monovalent saturated or unsaturated nonaromatic group having a single ring or multiple condensed rings from 1–12 carbon atoms and from 1–4 heteroatoms selected from nitrogen, phosphorous sulfur or oxygen within the ring. Such heterocycles are, for example, tetrahydrofuran, morpholine, piperidirke, pyrrolidine, etc.

The term "substituted heterocyclic" as used herein describes a subset of "heterocyclics" wherein the heterocycle nucleus is substituted with one or more functional groups such as alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "alkyls" wherein an alkyl group, as defined herein, links the heterocyclic group to the nucleus.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

In a preferred embodiment, an array of ligand moieties is synthesized on a substrate. This array is a combinatorial array of spatially separated surrate- or synthesis support-bound ligand moieties. Any of the previously discussed ligand types are amenable to this synthesis strategy; however, in a preferred embodiment, the array of ligand moieties comprises neutral bidentate ligands or chelating diimine ligands. Following its synthesis, the array of ligand moieties can be bound to a metal ion (e.g., transition metal ion, main group metal ion, and lanthanide ions).

In another preferred embodiment of this invention, a metal-ligand array or library is prepared such that each member of the ligand array is contacted with a metal ion precursor in the presence of a suitable solvent, wherein the metal-ligand array comprises neutral bidentate ligand moieties and the metal precursor is stabilized by at least one labile neutral Lewis base. Transition metal ion precursors are particularly preferred. In another preferred embodiment, the ligand moieties are diimine ligands and the transition metal precursor is selected from a Group 10 transition metal. In yet another preferred embodiment, the ligands are monoanionic bidentate ligand moieties and the transition metal precursor is stabilized by at least one labile anionic leaving group ligand.

In a preferred embodiment of this invention, ligand libraries described herein can be reacted with main group metal precursors to produce catalyst libraries. Such catalyst libraries are used for a variety of organic transformations requiring Lewis acidic sites, including stereo-selective coupling reactions (where a chiral Lewis acid is required), olefin oligomerization and olefin polymerization. As example of such reactions involves the reaction of trialkylaluminum with [2,2] or [2,1] ligand libraries, wherein each member of the ligand library is in the di- or mono-protic form respectively. This reaction will produce organometallic libraries comprising bidentate ligands bound to mono- or di-alkylaluminum centers. Such libraries can further be modified by reaction with an ion-exchange activator, such as $[PhNMe_2H]^+[B(C_6F_5)_4]^-$, to produce ligand-stabilized cationic aluminum reagents that are capable of acting as catalysts for organic coupling reactions, olefin oligomerization, and olefin polymerization. Examples of such [2,2] and [2,1] reactions are displayed below in Scheme 1:

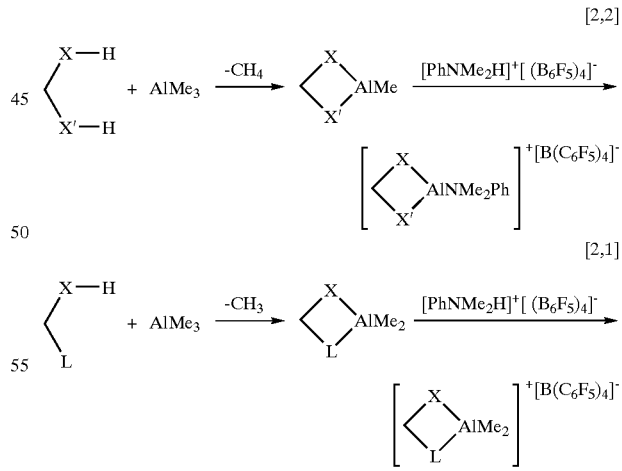

Scheme 1

These compounds are useful as catalysts in, for example, the polymerization of organic monomers. Organic monomers include, but are not limited to, ethylene, propylene, butene, isobutylene, hexene, methylacrylate, methyl vinyl ether, dienes, etc. Reactions can be carried out in gas phase or in solution, either on or off the substrate or synthesis support. The ability to assay catalytic properties of a metal-ligand compound on the substrate or synthesis support allows one to make libraries of catalysts bound to a variety of substrates or synthesis supports such as polystyrenes, silica, alumina, etc.

In still another preferred embodiment of this invention, a polymer blend is produced such that at least two members of the metal-ligand libraries are contacted with at least one cocatalyst and at least one monomer. In yet another preferred embodiment, olefins, diolefins and acetylenically unsaturated monomers are polymerized such that at least two members of the metal-ligand library are contacted with at least one cocatalyst and with at least one monomer.

Another exemplary library comprises diimine ligands of the general formula set forth below (I). These libraries can be synthesized by solution- or solid-phase methodologies or a combination thereof.

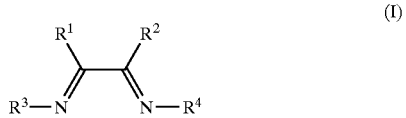
(I)

Substituent groups $R^1$, $R^2$, $R^3$ and $R^4$ can be chosen from a wide variety of organic fragments as discussed above. The role of the R group substituent is to modify the steric, stereochemical, solubility and electronic properties of the ligand system. The R group can be polar or nonpolar, and comprise neutral, acidic or basic functionalities. Suitable R groups include those described above and also organometalloid radicals, such as, for example, silyl or germyl radicals. The molecular weight of the R group substituent will, in general, range from 1 to 10,000 daltons. Polymeric or oligomeric R groups having molecular weights greater than 10,000 can also be prepared.

The diimine ligand libraries described above can be contacted with a variety of metallic precursors to form organometallic libraries. In one method, the ligand library is contacted with a coordinatively unsaturated metallic precursor or a metallic precursor complexed by a weakly bound leaving group ligand as depicted below in Scheme 2.

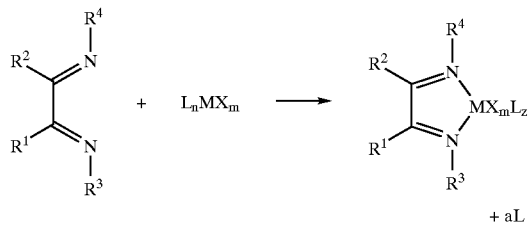
+ aL wherein:
L is a neutral Lewis base, n is an integer greater than or equal to zero;
z is an integer greater than or equal zero;
"a" represents the number of displaced L groups, and a+z=n;
M is a metal;
X is an anionic ligand, such as halide, hydrocarbyl or hydride; and
m represents the number of X ligands, and is an integer greater than or equal to zero.

Metal catalysts comprising non-coordinating anions can be synthesized by contacting a low valent metal precursor with the protonated form of a ligand library. For example, diimine stabilized transition metal catalysts can be prepared by a two step procedure comprising: 1) reacting the diimine library with the Bronsted acid of a non-coordinating anion to form an iminium salt library, and 2) contacting the iminium salt library with a suitable low valent metallic precursor. An example of such a process is depicted below in Scheme 3.

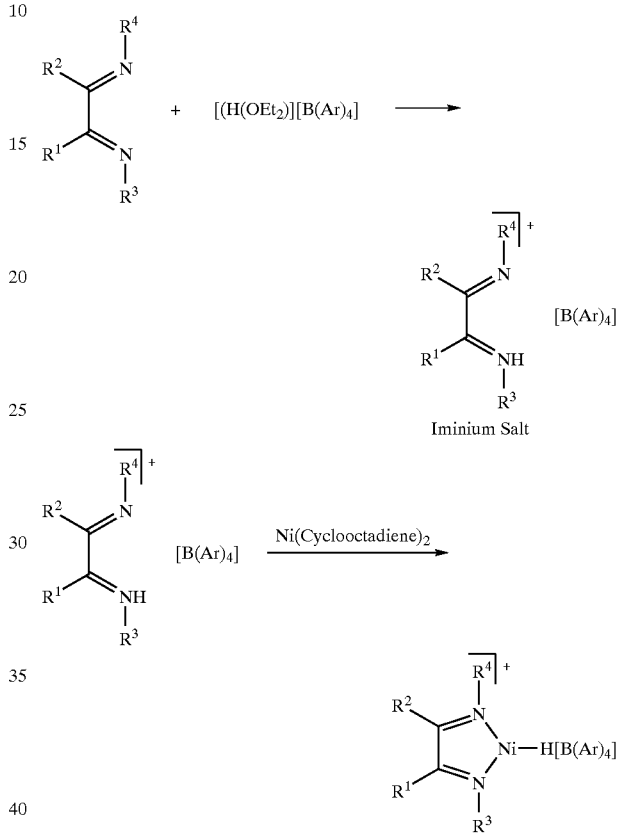

In certain embodiments, the ligands of the invention are made as pure stereo-, regio- or conformational isomers or, alternatively, the ligands can be a mixture of isomers. Metals suitable for use in the present invention include, but are not limited to, Cr, Mo, W, Pd, Ni, Pt, Ir, Rh, Co, etc. Activators suitable for use in the methods of the present invention include, but are not limited to, MAO, $[H(OEt_2)]^+[BAr_4]^-$, etc. Solvents suitable for use in the methods of the present invention include, but are not limited to, hexane, $CH_2Cl_2$, toluene, $CHCl_3$, etc.

The techniques described above are used to synthesize more than 3, more than 10, more than 20, more than 50, more than 100, more than 200, more than 500, more than 1,000, more than 10,000, more than 100,000 different compounds. Chemical synthesis steps can be conducted with a combination of solid-phase and solution-phase steps on substrates or synthesis supports such as pins, beads, or in wells. The methodology for varying ligands can be performed through either the parallel dispensing of reagents to spatially addressable sites, or by known "split-and-pool" combinatorial methodology.

The methods of the present invention also encompass embodiments wherein the linkage between the ligand and the substrate or synthesis support is varied in length and/or chemical composition.

D. Linkers

Combinatorial libraries can also be used to identify the optimal attachment of an organometallic catalyst to a substrate or solid support (e.g., silica, alumina, polystyrene, etc.). In another embodiment of the present invention, linker groups are interposed between the substrate and the ligand and/or the synthesis support and the ligand and/or the substrate and the synthesis support. A wide variety of cleavable and id noncleavable linker groups are known to and used by those of skill in the various chemical arts and can be used in the present invention to assemble ligand and organometallic libraries. The length and structure of the linkers are potential variables which can affect catalyst performance and can be an element of library design. Examples of linkers suitable fort use in the methods of the present invention are described in greater detail in PCT US94/05597, the teachings of which are incorporated herein by reference.

E. Metals

Once formed, the ligand libraries of the present invention can be contacted with metal ions to produce organometallic compounds. These compounds are typically catalysts. The metal ions are in the form of simple salts, mixed salts or organometallic compounds.

When the methods of the invention are used to discover an active catalyst, all classes of metal ions can be used. Broad classes of metal ions for use in practicing the instant invention include, but are not limited to, transition metal ions, lanthanide ions, main group metals, and actinide ions.

F. Immobilized Reagents

In practicing the instant invention to produce combinatorial solution libraries it is useful to use one or more immobilized reagents which accomplish different tasks. Thus, encompassed within the present invention is the use of, for example, immobilized bases, acids, proton sponges, oxidants, reductants, acylation and alkylation catalysts and the like. Many such immobilized agents are known to and used by those of skill in the art.

G. Non-coordinating Anions (NCA)

The presence, in a catalyst, of anions which are non- or weakly-coordinated to the metal center is known in the art to yield enhanced catalyst reactivity compared to those catalysts in which the anion is coordinated to the metal center (See, for example, U.S. Pat. Nos. 5,198,401; 5,278, 119; 5,502,017 and 5,447,895, the complete disclosures of which are incorporated by reference herein).

Anions which are bulky, highly stable and non-coordinating to the cationic metal center and which exhibit strong Lewis acidity and high reactivity are of particular utility in practicing the present invention. In preferred embodiments, the non-coordinating anions are boron-containing structures. In more preferred embodiments, the non-coordinating anions are boron tetraaryl structures in which the four aryl structures are substituted with one or more electron withdrawing substituents (e.g., fluorine) and at least one bulky R group to increase the solubility and the thermal stability of the organometallic or catalyst system. Representative R groups are as discussed above in the context of ligands. In preferred embodiments, the R groups are $C_1$ to $C_{20}$ alkyl or $C_1$ to $C_{20}$ alkyl-substituted group 14-metalloids (e.g., silicon, germanium or tin). Other non-coordinating ions of use in practicing the present invention will be apparent to those of skill in the art.

H. Diimine Catalyst Library Design and Synthesis

Having broadly set forth the principles and methods for the combinatorial synthesis of arrays of ligands and organometallic compounds, the design and synthetic methodologies for creating solution and solid phase libraries of diimine ligands and organometallic complexes will now be described.

Figure 27:
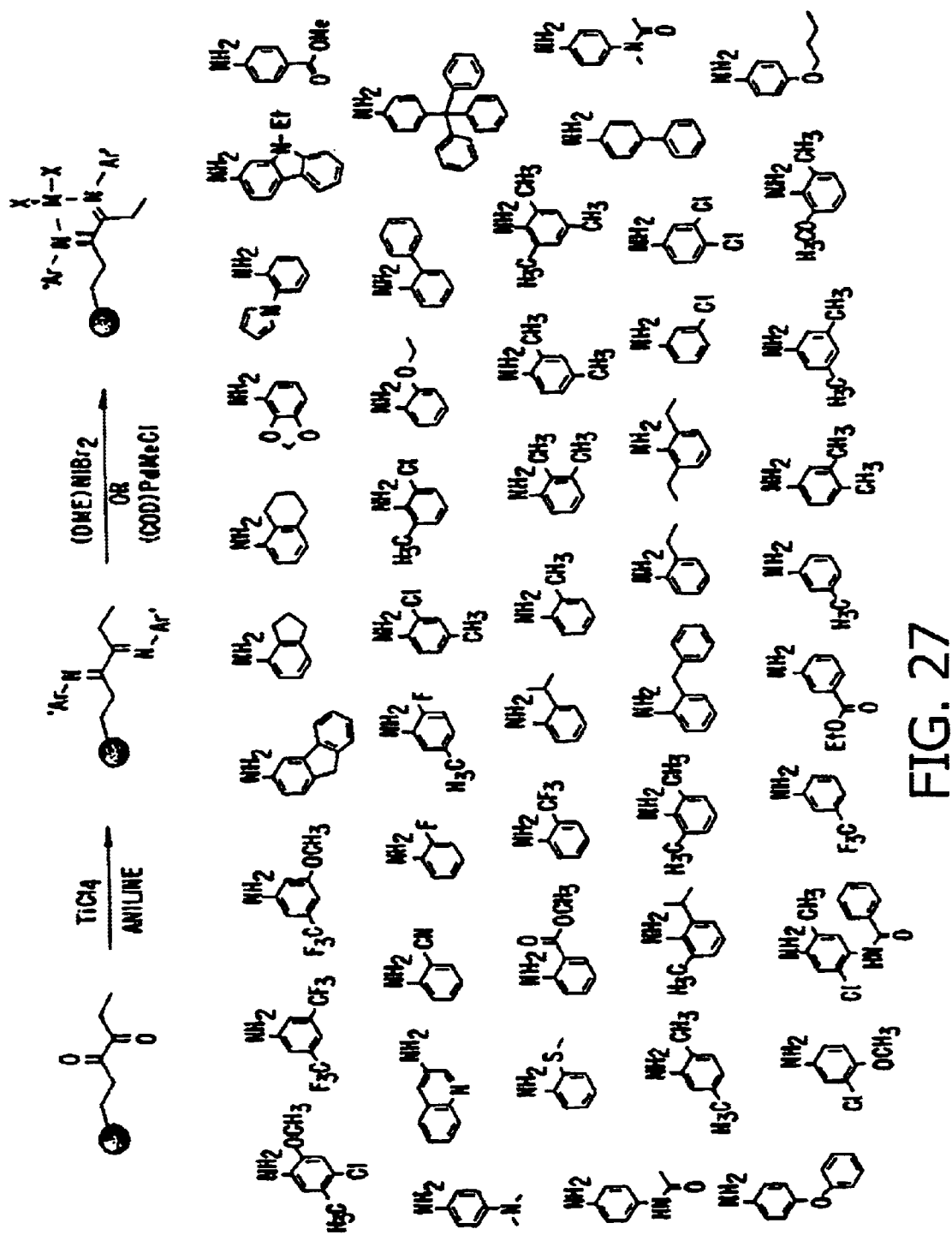
FIG. 27 illustrates the synthesis of a library of 48 diimine ligands which is subsequently converted to a library of 96 diimine-metal compounds.

FIG. 27 illustrates the design of a 96-well ligand and ligand-metal solid-phase library using Merrifield resin and the chemistry described in the Examples section. The library is composed of 48 diimine ligands derived from a Merrifield Resin-bound diketone precursor and 48 substituted anilines. The Merrifield Resin-bound diketone precursor is added to each of the 96-wells in the microtiter plate. An excess of each aniline is added to two of the wells within the microtiter plate, and the reactions are carried out and worked up using the protocols described in the Examples section. Ni and Pd metal ion precursors are combined with each resulting resin-bound diimine to produce the desired catalyst precursor. The catalyst precursors can be activated using appropriate activators and screened for activity and performance using the techniques described in the present invention.

Figure 28:
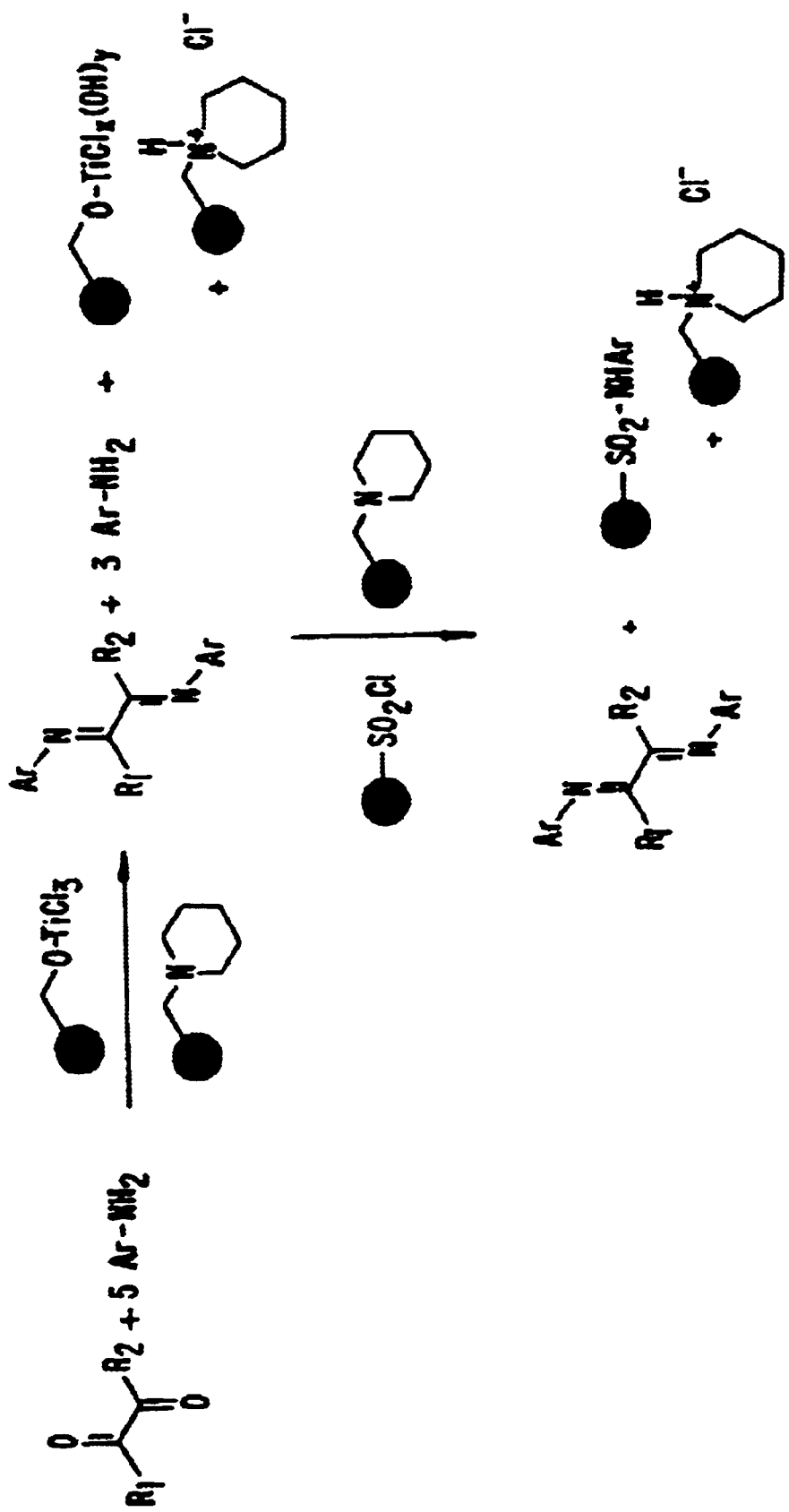
FIG. 28 illustrates a generalized solution-phase synthesis of diimines utilizing immobilized catalysts, proton sponges and reactant adsorbing reagents.
Figure 29:
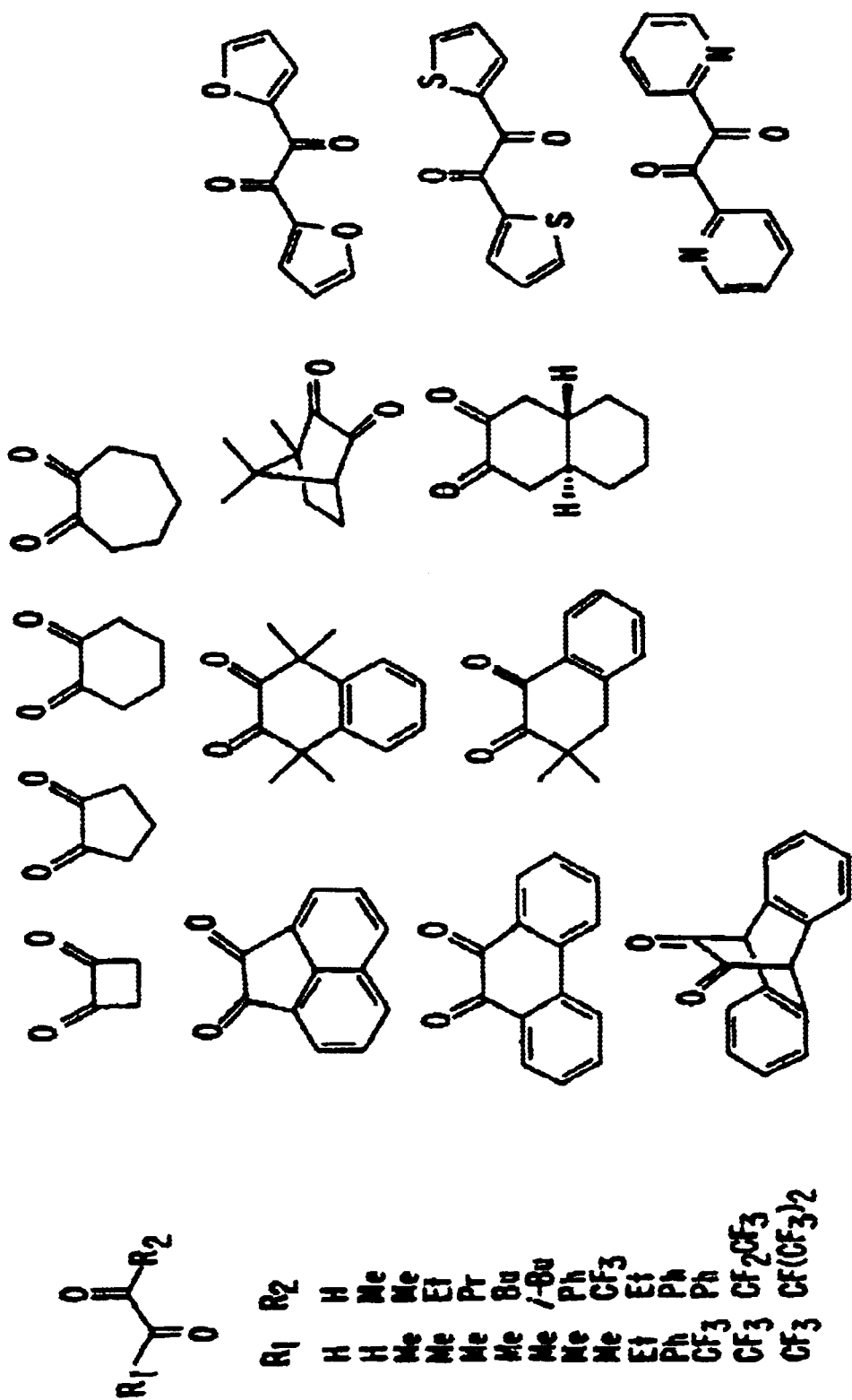
FIG. 29 illustrates an array of commercially-available diketones of use in practicing the present invention.
Figure 30:
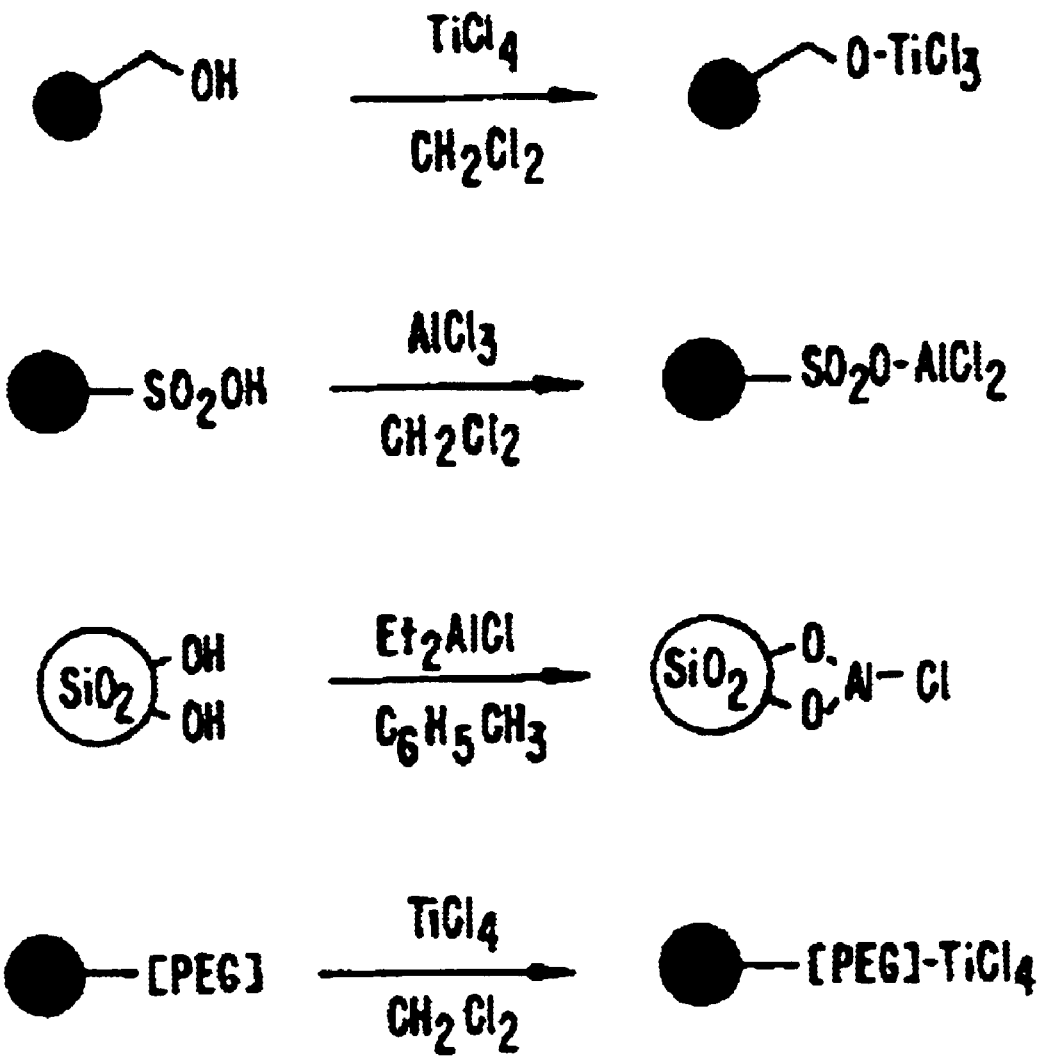
FIG. 30 illustrates examples of immobilized Lewis acid catalysts and dehydrating reagents.

Solution-phase diimine ligand and catalyst libraries can also be prepared using the methods of this invention. Solution-phase combinatorial chemistry is greatly facilitated by the use of solid-phase reagents which either catalyze reactions, deliver reagents or adsorb byproducts and/or unreacted starting materials. The general approach as it relates to the parallel synthesis of diimine ligands and the corresponding metallic complexes is displayed in FIG. 28 and described in Section 1.1 of the Examples section. Variation of the ligand backbone substitution (i.e., $R_1$ and $R_2$) can be accomplished by utilizing a large variety of commercially-available 1,2-diketones, examples of which are illustrated in FIG. 29. The solution-phase imine condensation can be catalyzed by, for example, a variety of solid-phase immobilized Lewis-acid catalysts/dehydrants (FIG. 30). Examples include:

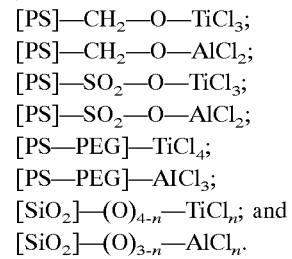

[PS]—$CH_2$—O—$TiCl_3$;

[PS]—$CH_2$—O—$AlCl_2$;

[PS]—$SO_2$—O—$TiCl_3$;

[PS]—$SO_2$—O—$AlCl_2$;

[PS—PEG]—$TiCl_4$;

[PS—PEG]—$AlCl_3$;

[$SiO_2$]—$(O)_{4-n}$—$TiCl_n$; and

[$SiO_2$]—$(O)_{3-n}$—$AlCl_n$.

In one embodiment, these catalysts are employed in conjunction with a solid-phase proton scavenging reagent such as [PS]—$CH_2$-piperidine.

Selective scavenging of excess aniline in the presence of diimines can be accomplished with a variety of solid-phase reagents. Examples include:

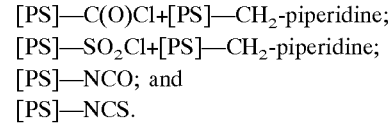

[PS]—C(O)Cl+[PS]—$CH_2$-piperidine;

[PS]—$SO_2$Cl+[PS]—$CH_2$-piperidine;

[PS]—NCO; and

[PS]—NCS.

III. Screening of Combinatorial Libraries

A. Introduction

The success of combinatorial chemistry depends upon the ability to first synthesize collections (libraries) of molecular compounds (members) where each compound has a unique elemental composition, and then to rapidly characterize each compound to identify compounds having specific, desired properties.

The present invention provides systems and methods for the analysis of libraries of catalysts and organometallic compounds. In the interest of simplicity, the analytical methods of the present invention are generally exemplified by reference to their use with libraries of catalytic compounds. Such use is not intended to limit the scope of the analytical methods which are also applicable to the analysis of libraries of organometallic compounds. A more complete description of systems and methods for interrogating large arrays of different compounds can be found in a commonly assigned provisional application entitled "SYSTEMS AND METHODS FOR RAPID SCREENING OF LIBRARIES OF DIFFERENT MATERIALS"Serial No. 60/050,049, filed Jun. 11, 1997, the complete disclosure of which is incorporated herein by reference for all purposes.

The use of combinatorial chemistry for discovering and optimizing new materials requires the existence of spatially selective, high throughput methods for measuring such properties as activity, i.e., turnover, selectivity in converting reactants into desired products, and stability during operation under a wide variety of substrate concentrations and reaction conditions. The "philosophy" of combinatorial screening is quite different from that of conventional quantitative analytical chemistry. Rather than striving for precise determination of accurate numerical values of material properties, in combinatorial screening the primary objective is the rapid, comparison of the properties of the individual members on each library relative to each other. This may require trading off quantitative accuracy for speed. Spatially selective characterization methods include those capable of: (I) Identification and characterization of gas phase products and volatile components of the condensed phase products; (ii) Identification and characterization of condensed phase products; and (iii) Measurement of physical properties of the elements on the library.

The methods described herein include several fundamentally different approaches including scanned mass spectrometry and chromatography, ultraviolet, visible, infrared and other electromagnetic imaging and spectroscopy, and acoustic imaging methods. Methods for measuring catalytic activity and specificity involve, for example, direct measurement of product concentrations or indirect measurement of the heat of reaction. Several implementations are described which include both truly parallel methods of detection as well as methods that can operate rapidly in series. In some embodiments, the parallel methods have the common approach of integrating position sensitive photon detectors into the measurement system, while the serial methods rely on controlled scanning of the library or detector/source relative to one another. In exemplary embodiments, the present invention has the ability to screen combinatorial libraries containing more than 10 different materials on a single substrate, more than 50 different materials, alternatively more than 100 different materials, alternatively more than $10^3$ different materials and often more than $10^6$ different materials on a single substrate.

According to one aspect of the present invention, a variety of embodiments are described for the identification and characterization of gas phase products or volatile components of the condensed phase products. In some of these embodiments, scanning mass spectrometry is employed to locally measure the relative concentrations of reactants and products in close proximity to a catalyst compound on the library. The library elements are preferably activated by a heat source serially or in parallel. Such a system can be enhanced using laser desorption techniques which vaporize liquid, bound reactants and/or products in a spatially localized format and facilitate the intake of chemicals in the scanning mass spectrometry measurement system.

In a first embodiment of this aspect of the invention, a differentially pumped mass spectrometer is employed to sample the product stream or the volume surrounding the library compound. In a second embodiment, diffusive or supersonic molecular beam sampling are employed in a differentially pumped mass spectrometer system, wherein oxidation-reduction of a library can be performed in situ. A third embodiment uses a single stage differentially pumped mass spectrometer system with a capillary feed that can be applied to a static QMS and rotatable or translatable library. In a fourth embodiment, an individual flow-through library sampling system is described. This system employs individual flow-though paths through each library element so that introduction of reactants can be performed sequentially, and enables products to be more concentrated in the product outlet stream. In a fifth embodiment, a differentially pumped mass spectrometer with a simplified flow system is described. This flow system provides a rapid screening method that involves a simple flow system wherein a small volume is created adjacent to the library and filled with reactant gas through an inlet port, and outlet gas is sampled by a differential mass spectrometer or a gas chromatograph-mass spectrometer combination.

In preferred embodiments, the mass spectrometers of the present invention are capable of detecting components at about one-part-per-million (1 ppm), and preferably about ten-parts-per-trillion (10 ppt). In addition, the mass spectrometers are capable of rapidly scanning a large array of materials on a substrate, usually scanning at least 0.1 library elements per second, preferably at least 1 library element per second, more preferably at least 10 library elements per second, even more preferably at least 100 library elements per second, and often greater than 1000 library elements per second. The high throughput (0.1 to greater than 1000 library elements per second), position sensitive (resolution 0.01–10 mm) methods described herein provides the spectrometer with the ability to quickly and reliably characterize large arrays of materials to optimize the materials within the array.

The techniques of the present invention include spatially localized MS, in which the sampling probe of the spectrometer is positioned in a novel way over individual library sites, then scanned to other sites. In addition, the techniques include more course screens achieved by distancing the mass spectrometer from the library, and then heating the entire library to measure if any library members display activity or desired products. If desired products are detected, half of the library can be heated and screened for desired activity or products. This "splitting" can be repeated until active sites, if any, are identified.

In another aspect of the invention, optical spectroscopy is employed to identify and characterize gas phase products or volatile components of the condensed phase products. In these embodiments, library elements are typically activated by a heat source serially or in parallel. In a first embodiment, an ultraviolet and visible emission-excitation spectroscopy is implemented in a scanning configuration either by scanning a laser excitation source over the catalytic surface and monitoring the emission with an energy specific, single photon detector, or by simultaneous excitation with a single wavelength, while emission imaging with a position sensitive detector. In a second embodiment, a scanning multi-wave mixing fluorescence imaging system uses a degenerate four-wave mixing optical technique that depends on the interaction of three photons to produce the fourth photon, i.e., the signal, and requires only one wavelength, wherein the signal is a coherent beam easy to detect.

In another aspect of the invention, gas chromatography and high-throughput detection is employed to identify and characterize gas phase products or volatile components of the condensed phase products. Chromatography, whereby gas or liquid-phase products may be separated and detected by their differential rates of movement through specialized adsorption/diffusion columns, is used for the measurement of combinatorial libraries either using conventional autosampling from multiple sites or in our novel scanning configuration. Multiple columns (one each over each site, or one each over a line of sites than scanned) may be used or a single column scanned over the entire library. The "column" may be nothing more than a tube through which polymer products move at a rate related to their viscosity and, hence, indirectly related to their molecular weight.

In yet another aspect of the invention, optical methods are described for the identification and characterization of condensed phase products. Similar to previous embodiments, the library elements can be activated by a heat source serially or in parallel. A first embodiment of this aspect of the invention involves evaluating specific molecular vibrations, wherein a monochromated IR source is passed through the library (serially or sequentially), and the intensity of the transmitted beam measured as a function of time during the progression of a reaction. A second embodiment employs infrared emission. For condensed phase products, which are in thermal contact with, for example, a catalyst, infrared emission imaging of the library (in parallel or serially) provides relative differences in temperature change between library elements. In a third embodiment, photon scattering analysis is employed, whereby relative and time varying differences in the molecular weight distribution and average molecular weight of a library for liquid products and reactants, are monitored by changes in the relative intensity of scattered light measured as a function of angle relative to the incident beam. In a fourth embodiment, polarized light imaging techniques are used. In these techniques, the formation of optically active crystalline domains in solids gives rise to optical rotation and/or preferential transmission of polarized light. These techniques may be carried out with a polarized light source and a polarized light detector, or, by transilluminating an entire library with polarized light and then imaging the transmitted light onto a CCD through a polarizer. Characterization of the relative changes in orientational order are monitored in real time to observe, for example, a rate of polymerization.

In another aspect of the invention, mechanical properties of the library elements are used to identify and characterize condensed phase products. Preferably, ultrasonic monitoring of reactions producing liquid or solid products are characterized by changes in the mechanical properties of the products by ultrasonic probing. Using the fact that the velocity of acoustic waves is equal to the square root of the ratio of a material's bulk modulus to its density, monitoring the ratio in every element of a combinatorial library allows the direct comparison of relative rates of reaction and gives information as to the molecular weight distribution, etc.

In yet another aspect of the invention, identification and characterization of the physical properties is achieved wherein using a two-dimensional infrared imaging system for parallel monitoring of library heat of reaction, such that the entire library is monitored simultaneously using the heat of reaction to alter the temperature of compound (e.g. a solid catalyst) and surrounding support with a two-dimensional infrared imaging camera, wherein the individual library element's temperature (and its difference relative to the surrounding elements) reflects the activity of the specific library site and the heat of reaction.

In addition to the gas phase analysis methods described above for the volatile (or vaporizable) product components of condensed phase products, methods have been developed for characterizing the condensed phase products themselves on the library surface. Such products which might be encountered, for example, in the gas phase polymerization of ethylene to condensed phase polyethylene or hydrolysis of liquid dimethyldichlorosilane to elastomeric polydimethylsiloxane. These methods of high throughput screening are sensitive to the optical and mechanical properties of the substrates. The optical methods described provide a means of parallel screening for both specificity and activity using infrared absorption and emission as well as the optical polarization and scattering of the condensed phase products. Screening for mechanical properties cannot be used for the detection of specific products, however, for reactions (such as polymerization) where the rate of change of bulk properties reflect the rate of catalysis (degree of polymerization), measurements of bulk properties provides a method of rapid screening for desirable reaction kinetics.

Generally, the two-dimensional combinatorial catalysis library elements will be synthesized either on a porous substrate such as, for example, alumina or silica, or on an impermeable substrate in one of the two configurations depicted schematically in cross section in FIG. 14. The substrates (shown in white in FIG. 14) are non-reactive materials of any two-dimensional shape that is convenient for scanning, such as circular disks, rectangles, squares, etc. The substrate's function is to position and isolate the elements of the catalyst library in the reactant stream. The substrate can contain indentations or "wells" to contain the library elements which consist of the catalyst compound possibly present on a support material, i.e., on a synthesis support.

Figure 14A:
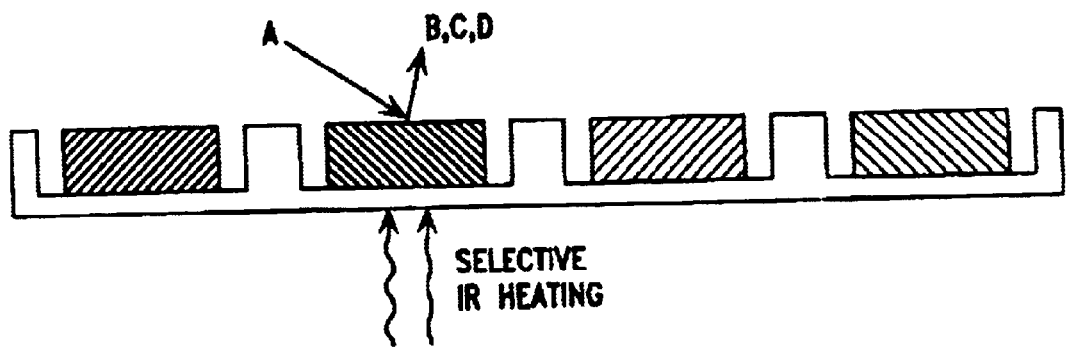
FIGS. 14A and 14B illustrate various exemplary substrate configurations which can be used in carrying out the methods of the present invention.

As shown in FIG. 14A, in the first configuration, the sample chamber is filled with reactant gas A at a pressure P and individual catalyst elements (the catalyst compound alone or the compound deposited on a support) are selectively activated by focused IR heating or by resistive heating elements incorporated into the substrate. All library elements are in contact with the reactant gas at a pressure P; however, only when heated will the catalyst possess significant activity to produce appreciable products. The library can, for example, be cooled to avoid any side reactions.

Figure 14B:
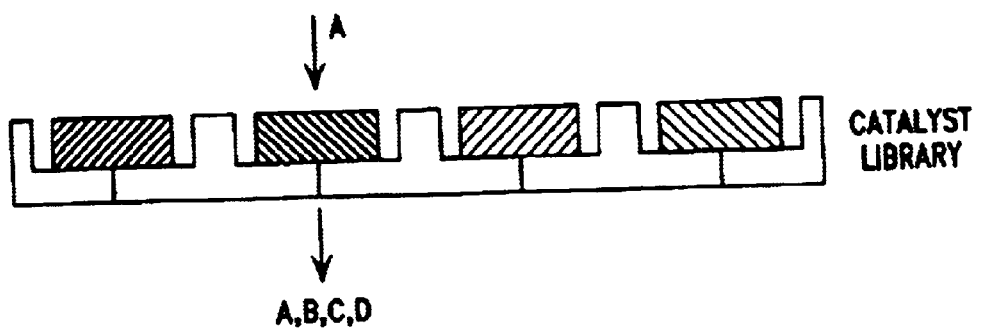

In the second configuration set forth in FIG. 14B, a permeable substrate is utilized and reactant gas at a pressure P on top of the library is driven through the supported catalyst library element and then both unreacted reactants and products pass through the porous substrate into a region of lower pressure where the products are detected. The flow can be directed though one element path at a time by sealed conduits or, alternatively, it can be directed through all elements simultaneously. Individual elements can be selectively heated for serial measurement of the products or the entire library heated for parallel characterization (e.g., optical emission imaging). This method has the advantage that the pressure drop across the substrate allows the gas detection system to sample a lower pressure stream.

B. Identification and Characterization of Gas Phase Products or Volatile Components of the Condensed Phase Products Reactions producing gas phase products are monitored, for example, by devices capable of spatially selective mass spectroscopy, spatially selective optical spectroscopy (resonant-enhanced multiphoton ionization and UV-visible absorption-emission) and gas chromatography.

1. Gas Phase Characterization by Mass Spectroscopy

Mass spectroscopy (MS) is a well established method of analytical chemistry for the identification of chemical species. The systems described herein are applicable both to spatially localized MS, wherein the device is positioned in a novel way over individual catalytic library sites, and to more course screens, wherein the MS is distanced from the library and the entire library is heated to measure if any library members display catalytic activity or desired products. In the latter embodiment, if desired products are detected, half of the library can be heated and screened for desired products. This "splitting" can be repeated until active sites, if any, are identified.

In one particular embodiment of the mass detection strategy, a mass spectrometer capable of detecting a one-part-per-million (1 ppm) component in one atmosphere background pressure has been developed. This system involves a pinhole opening on the order of about 0.01 mm to about 0.5 mm and, more preferably, 0.05 mm to about 0.2 mm to sample the down stream gas mixture after it has passed through the mini-catalyst bed, followed by three-stage differential pumping, electron-impact ionization (or photo-ionization) and quadruple mass detector. The catalyst library is contained on a disk that is scanned in the X-Y plane so that every site can be accessed. Depending on the rate of the reactions, real-time kinetics can be followed by this approach.

Figure 15:
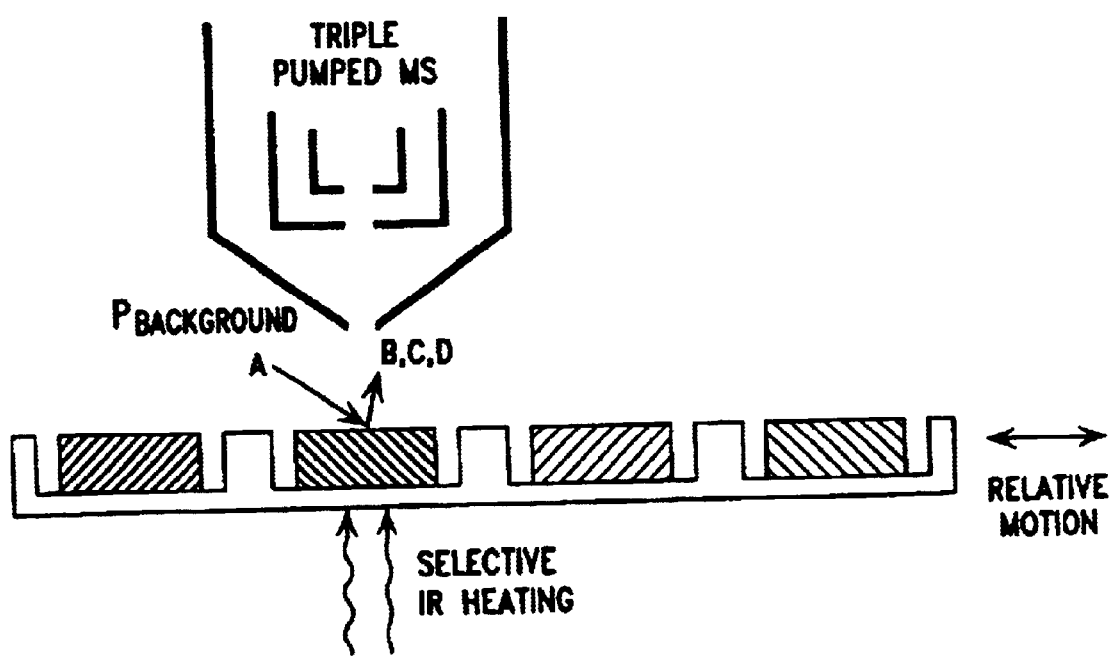
FIG. 15 illustrates an example of a system employing a differentially pumped mass spectrometer that samples product stream or volume surrounding the library compound.

(i) Differentially Pumped Mass Spectrometer that Samples Product Stream or Volume Surrounding the Library Compound:

Measurement of the gas phase reaction products is achieved in several ways, each with advantages depending on the library. The most direct measurement uses a highly sensitive species dependent probe, such as a differentially pumped mass spectrometer, to sample the product stream or the volume surrounding the library compound. The first approach involves careful positioning of the mass spectrometer sampling tube over each element (or in the product stream) and analyzing the products of each library element serially as depicted in FIG. 15. Each library element is individually addressed/activated by a scanned IR heating source to insure product production only in individual elements and to limit side reactions and catalyst aging (alternatively, individual resistive heaters can be incorporated into the substrate). This implementation assumes that the activity of the catalyst is negligible until it is heated.

Figure 16:
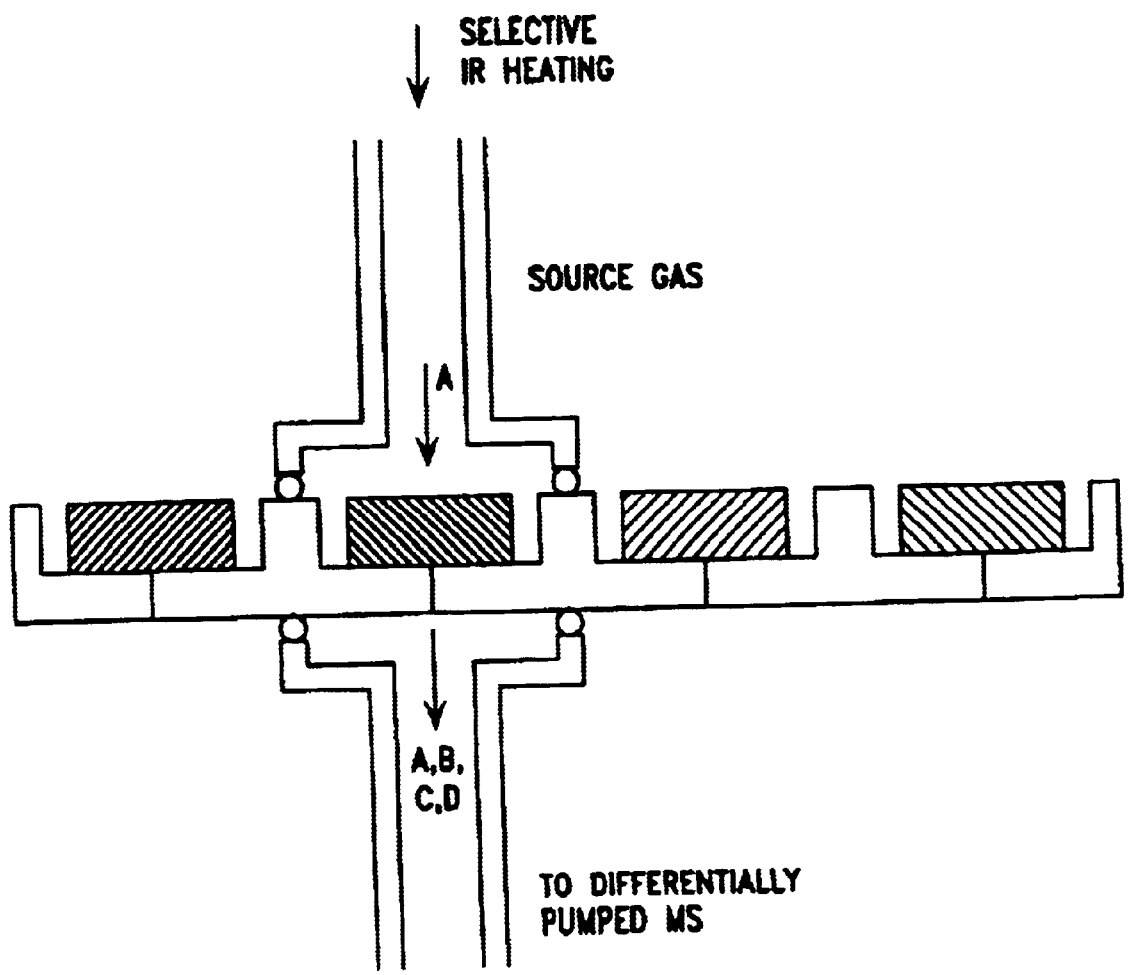
FIG. 16 illustrates an example of an individual flow-through library system.

In a presently preferred embodiment, the library is physically scanned in front of a fixed heating source- detector nozzle or through fixed inlet and outlet tubes that are sealed against the library around each individual element serially (see, e.g., FIG. 16). Alternatively, the library can be fixed and the detector assembly and heater scanned.

Figure 17:
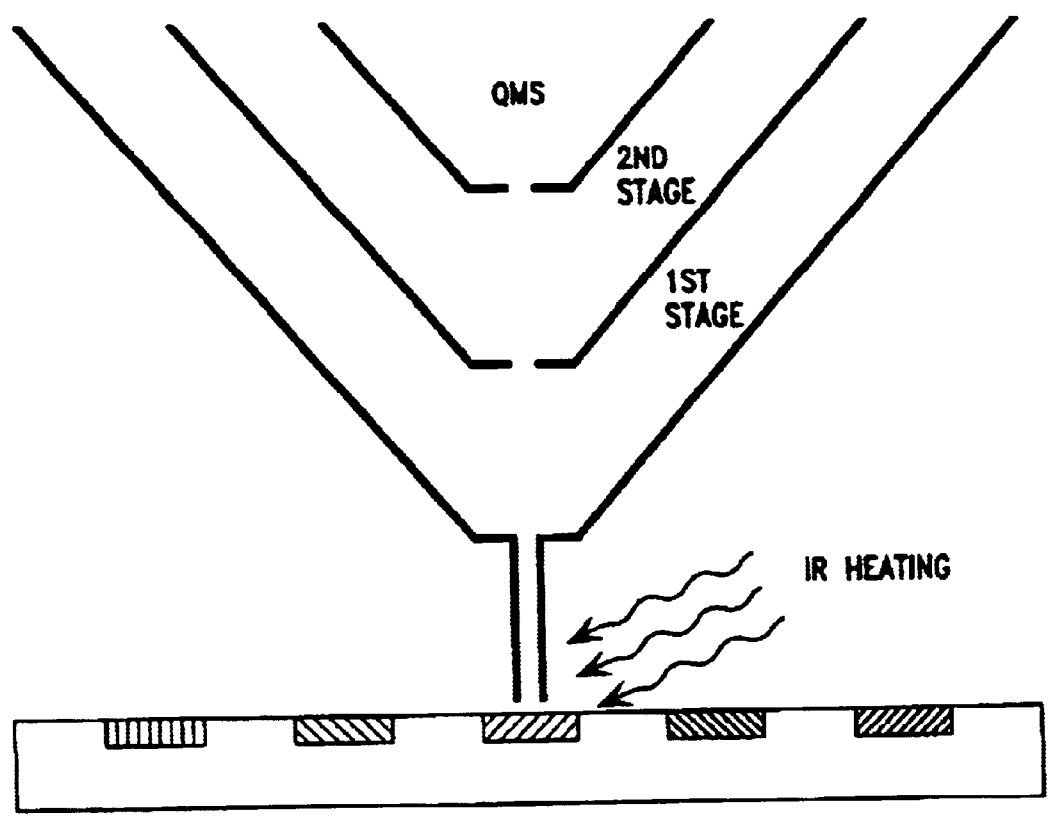
FIG. 17 illustrates an example of a Supersonic Molecular Beam Sampling System.

(ii) Supersonic Molecular Beam Sampling System:

The Supersonic Molecular Beam Sampling System (SMBSS) depicted in FIG. 17 uses a differentially pumped mass spectrometer system, and can be applied to a variety of systems. The substrate can be $SiO_2$ (e.g., oxidized Si wafer) clamped in a susceptor. Oxidation-reduction of a library is performed in situ, and heating of the library can be performed simultaneously or sequentially, using IR or patterned conductors on the back of the substrate for resistive heating. The substrate can, for example, contain insertable plugs of supported catalyst.

The library can have the dimensions: 1 mm×1 mm pixels with c/c spacing of 2 mm (this is the scale of the drawing depicted). On a 3¼ inch by 3¼ inch substrate, this gives a 40×40 array, i.e., 1600 catalysts per library substrate. Alternatively, a library of 2 mm×2 mm catalysts with a c/c spacing of 4 mm gives a library of 20×20 or 400 different catalysts. Alternatively, a library of 0.1 mm×0.1 mm elements with a c/c spacing of 0.2 mm gives a library of 400×400 or 160,000 different catalysts.

In a particular example of this three stage differentially pumped system, the substrate consists of an approximately 4½ inches×4½ inches of a chemically inert thermal insulator material into which the silicon dioxide or alumina pellets containing catalyst library elements are pressed. Each sample element is an approximately 4 mm disc. This gives rise to 625 catalysts per library. The sampled gas will be between about 1 and 5 atm off the library and enter the first stage through a 100 micron aperture. This gives rise to an entrance flux of approximately $2.6\times10^{19}$ molecules per second. The first stage pressure will be $1.1\times10^{-3}$ torr using a 1000 l/s turbo molecular pump (TMP). The first stage skimmer has a larger aperture of 200 microns giving rise to a flux through the skimmer $1.2\times10^{14}$ molecules per second. The 200 micron skimmer separates the first stage region (at $1.1\times10^{-3}$ torr) from the second stage which is maintained at a pressure of $1.9\times10^{-8}$ torr by a 200 l/s TMP. The final stage skimmer has a 400 micron aperture expected to extract $9.2\times10^{9}$ molecules/s in a molecular beam into the final stage maintained at approximately $\times10^{-11}$ torr (with a diffuse scattered pressure of approximately $8\times10^{-13}$ torr ) using a 200 l/s TMP.

The effective beam pressure (flux) at the detector is estimated to be approximately $10^{-3}$ torr ($4.1\times10^{16}$ molecules/cm²-s) which will provide ample signal for reliable detection. A schematic is shown in FIG. 17 and illustrates the infra-red heating of the detector element sample below a quadruple mass spectrometer nozzle.

Figure 18:
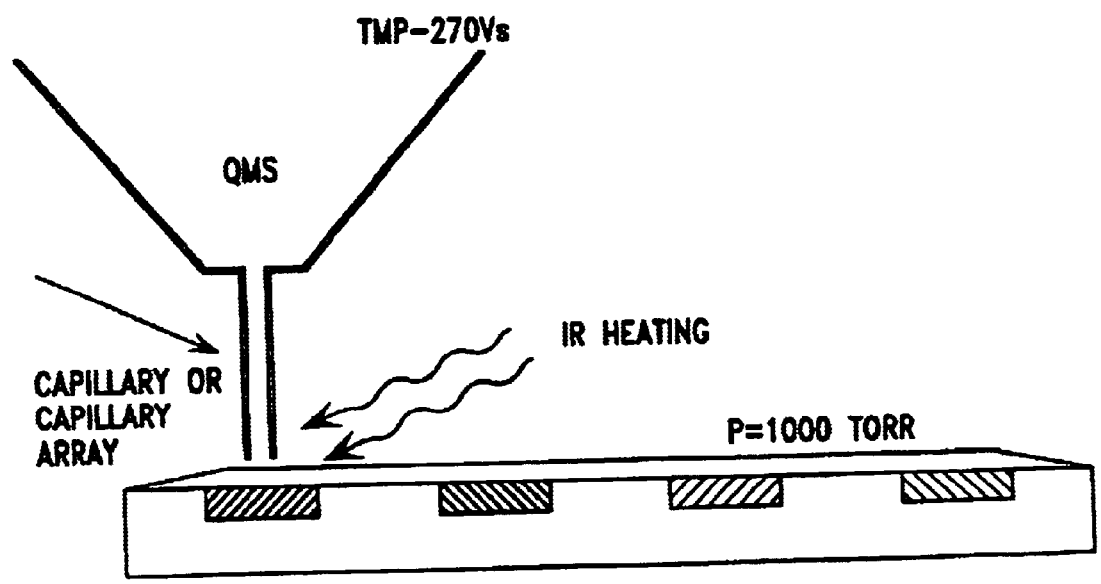
FIG. 18 illustrates an example of a system employing a single stage differentially pumped mass spectrometer.

(iii) Single Stage Differentially Pumped Mass Spectrometer:

The Single Stage Differentially Pumped Mass Spectrometer system with a capillary feed, depicted in FIG. 18, uses a single-stage differentially pumped mass spectrometer system. This system can be applied to a static QMS and rotatable or translatable library. The heat source is, for example, IR from below or above the substrate. The entire library can he heated to oxidize or reduce the catalysts. Also, the entire library can be heated during the reaction to assess whether any catalyst is active.

Although numerous variations of this implementation exist, the basic configuration is depicted in FIG. 18, wherein sampling occurs from a circular disc library. Sampling a reactor pressure of $10^3$ torr either a small capillary or aperture area of approximately $1.96\times10^{-7}$ cm² connects the quadruple mass spectrometer chamber to the high pressure region. The pressure within the mass spectrometer chamber is approximately $7.2\times10^{-6}$ torr (upper limit) which can be achieved using a 270 liter per second turbo molecular pump. Various lengths of capillary or orifice tapers can be used.

In the schematic set forth in FIG. 18, if the inlet flow rate is 0.1 liters per second and the pumping speed approximately 1 liter per second, then the steady state reactor pressure is 100 torr and the resonance time is 5 seconds assuming the reactor volume is 5 liters. In the schematic, a circular sample stage is depicted using a 3 inch wafer and 6.35 mm diameter sample discs. In this implementation 16 different catalysts can be used.

(iv) Individual Flow-Through Library Sampling:

The Individual Flow-Through Libraries system is similar to the Embedded Catalyst Impregnated in Micro-porous Silica Capped by Macro-porous Silica system described below in (vi), except that this embodiment employs individual flow-though paths through each library element so that introduction of reactants can be performed sequentially. This system provides a distinct advantage in that it enables products to be more concentrated in the product outlet stream.

In an individual flow through library implementation, typically fewer catalysts library elements will be utilized (for example, 8×12=96 catalysts). This gives the advantage of extremely high concentrations of products in the outlet stream. The flow into the vacuum side will be dictated by pressure drop through the porous support for 1 cc/s at 1000 torr this gives rise to $3.5 \times 10^{19}$ molecules per second. The vacuum pressure will be 0.2 torr using a 10 micron diameter orifice into the quadruple mass spectrometer at 100 l/s turbo molecular pumping speed gives rise to a pressure in the mass spectrometer of $1.7 \times 10^{-8}$ torr. See, FIG. 16.

Figure 19:
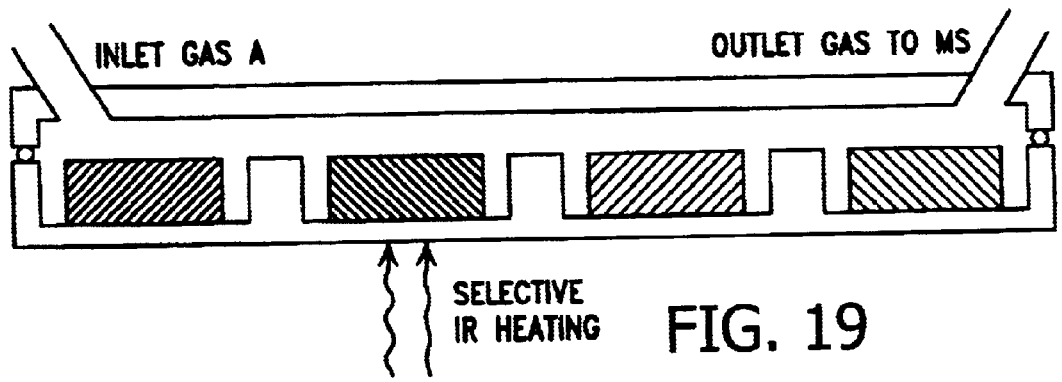
FIG. 19 illustrates an example of a differentially pumped mass spectrometer with a simplified flow system.

(v) Differentially Pumped Mass Spectrometer with a Simplified Flow System:

A rapid screening method that involves a relatively simple flow system and requires only a scanned IR source is depicted schematically in FIG. 19. A "small" volume is created adjacent to the library and filled with reactant gas A through an inlet port. Selective IR heating of a thin substrate activates a catalyst element of interest which produces products into the volume. The outlet gas is then sampled by a differential mass spectrometer (or if a large number of high molecular weight products exist, a gas chromatograph can be implemented prior to the mass spectrometer to separate the products). Maintaining a small volume above the library will improve the sensitivity of the mass spectrometric detection. A high surface area support should be used in each catalyst element. To reduce parasitic reactions at other sites, the library can be maintained at low temperature and only the active element heated.

A similar arrangement can be configured for a flow-through geometry whereby the inlet is placed on the opposite side of the library as the outlet and the substrate is porous to allow gas passage through each member. Heating of the substrate can also be performed by (i) selectively heating regions of, for example, 10 elements, (ii) screening product formation by detecting the average of the signal from the 10 elements, then (iii) focusing in on individual elements in the selected regions that produce significant signals. This strategy is referred to as a deconvolution strategy.

(vi) Embedded Catalyst Impregnated in Micro-porous Silica Capped by Macro-porous Silica:

In another embodiment, the present invention employs a Embedded Catalyst Impregnated in Micro-porous Silica Capped by Macro-porous Silica system which uses a differentially pumped mass spectrometer system. Differential heating of individual catalyst volumes will increase diffusivity of reactants and products through the membrane locally at the catalyst being examined. This provides a distinct advantage to this system that will enable products to be more concentrated in the reactor volume (above the membrane) being sampled by the mass spectrometer.

In this system, the substrate is depicted in an up-side-down configuration, wherein gas can flow through all of the library elements simultaneously, driven by a pressure gradient wherein the pressure at the bottom is greater than the pressure at the top. Detection is performed from the top (back of the substrate) in the lower pressure environment. The heat source is, for example, IR or resistance, and is applied sequentially to each element.

In this implementation, the high pressure zone is in contact with the catalyst so the catalyst sees the high pressure (working pressure) of the chamber system. This will replicate the in practice conditions. If the pressure behind the plug is greater than 1000 torr, $P_o$ is adjusted to be approximately $10^{-3}$ torr. (This can be done with a roughing pump and membrane porosity). If the orifice is 1 micron to sample into the mass spectrometer, this give rise to a flux of $3.2 \times 10^{17}$ molecules/cm$^2$-s. The leak rate is $2.5 \times 10^{15}$ molecules/s and assuming a 100 l/s turbo molecular pump, $P_1$ is $7.8 \times 10^{-7}$ torr.

Figure 20:
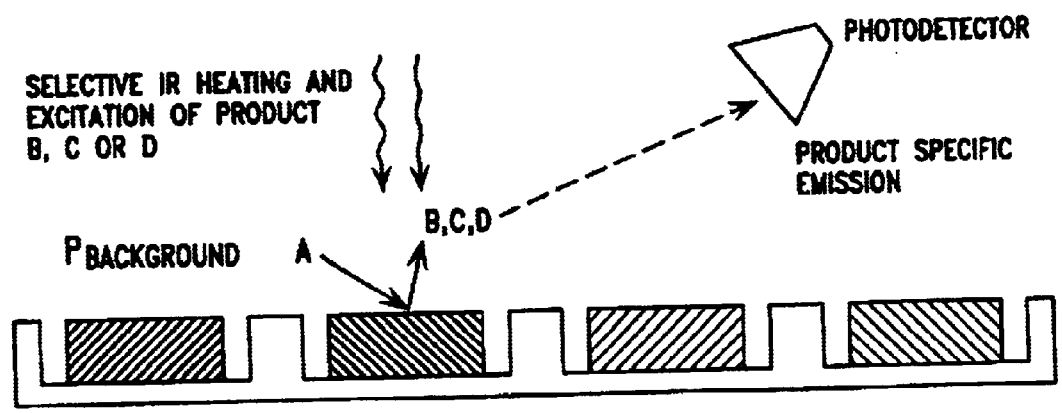
FIGS. 20 and 21 illustrates systems employing ultraviolet and visible emission-excitation spectroscopy.

2. Gas Phase Characterization by Optical Spectroscopy:

(i) Ultraviolet and Visible Emission-Excitation Spectroscopy:

For library characterization, traditional ultraviolet and visible emission-excitation spectroscopy has been implemented in a scanning configuration by 1) scanning a laser excitation source (uv-vis), member-by-member, over the catalytic surface and subsequently monitoring the emission with an energy specific, single photon detector as illustrated in FIG. 20. In this embodiment, individual library elements are heated with a focussed infrared source or the entire library may be heated uniformly. Products produced must contain a desired product with a distinct excitation-emission signature with high efficiency. The excitation source tuned to the desired product is focussed directly on or above the element (or on a cooled condensation membrane positioned directly above the element) and the emission monitored in an energy selective emission photodetector.

Figure 21:
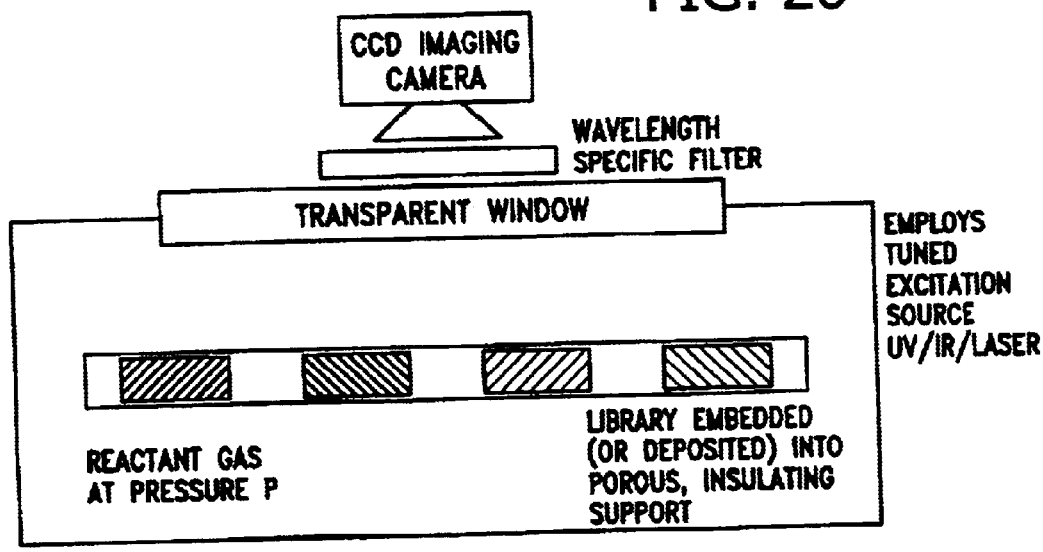

A second embodiment, illustrated in FIG. 21, is a parallel extension of the above method which operates by simultaneous excitation of the entire heated library area with the single product excitation wavelength, while emission imaging with a position sensitive detector, such as a CCD through a bandpass filter specific for the desired product emission as illustrated in FIG. 21.

(ii) Scanning Multi-Wave Mixing Fluorescence Imaging:

The spectroscopic techniques of degenerate four-wave mixing (DFWM) and laser-induced fluorescence (LIF) have been applied to the detection of minor species for combustion diagnostics at high sensitivities (Mann, B. A., et al., "Detection and imaging of nitrogen dioxide with the degenerate four-wave-mixing and laser-induced-fluorescence techniques," *Applied Optics*, 20 Jan. 1996, 35(3):475–81.). Degenerate four-wave mixing is a nonlinear optical technique that depends on the interaction of three photons to produce the fourth photon, i.e., the signal. It requires only one wavelength and, thus, it is relatively simple to set up. The signal is a coherent and directional beam (unlike fluorescence which is emitted in all directions) and is therefore easy to detect at high sensitivity (approximately 10,000 molecules under favorable conditions). The technique has a spatial resolution determined, in part, by the localization of the lasers (in practice approximately 10 microns). The selectivity of this technique relies on the absorption properties of the species being detected and can be thought of as being analogous to absorption spectroscopy, except that it is more sensitive, more selective and has a higher spatial resolution.

For library scanning, the optical detection system has a configuration similar to the Supersonic Molecular Beam Sampling System, described above, in-so-far-as the library format, heating and motion may be used for faster screening. The optical detection uses a dual wavelength laser detection system whereby one laser is used for excitation and another for absorption spectroscopy. The sensitivity of these methodologies are approximately $10^{-18}$ molar (one atmosphere of an ideal gas gives rise $2.7 \times 10^{19}$ molecules per cm$^3$).

3. Gas Phase Characterization by Gas Chromatography:

(i) Gas Chromatography:

Gas chromatography is another general purpose means of characterizing gas phase products. The method for simple samples is well known to those familiar with the art. High-throughput measurement of libraries can be used for the rapid screening of catalysts. In one application, multi-port injection valve can sample a sequence of catalyst sites rapidly. A multi-column system can be used if higher throughput is required. Mass spectrometry and chromatography are generally used as complementary techniques and like the scanning mass spectrometer (above), a scanning chromatograph configuration whereby the library is scanned under the GC intake may be used for HTS.

C. Characterization of Condensed Phase Products

In addition to the gas phase analysis methods described above for the volatile (or vaporizable) product components of condensed phase products, methods have been developed for characterizing the condensed phase products themselves on the library surface. Such products which might be encountered, for example, in the gas phase polymerization of ethylene to condensed phase polyethylene or hydrolysis of liquid dimethyldichlorosilane to elastomeric polydimethylsiloxane. These methods of high throughput screening are sensitive to the optical and mechanical properties of the substrates. The optical methods described provide a means of parallel screening for both specificity and activity using infrared absorption and emission as well as the optical polarization and scattering of the condensed phase products. Screening for mechanical properties cannot be used for the detection of specific products, however, for reactions (such as polymerization) where the rate of change of bulk properties reflect the rate of catalysis (degree of polymerization), measurements of bulk properties provide a means of rapid screening for desirable reaction kinetics.

1. Condensed Phase Product Characterization by Optical Methods:

(i) Infrared Absorption:

Specific molecular vibrations can be evaluated by infrared absorption and the method applied to single samples well known. For example, because C=C stretch modes have specific absorptions at 1650 and 2200 $cm^{-1}$, monitoring the relative change in absorption at those frequencies over a library, will provide a measure of the relative changes in the number of C=C bonds in the system and, therefore, reflect, for example, the polymerization of ethylene (see, FIG. 22).

Figure 22:
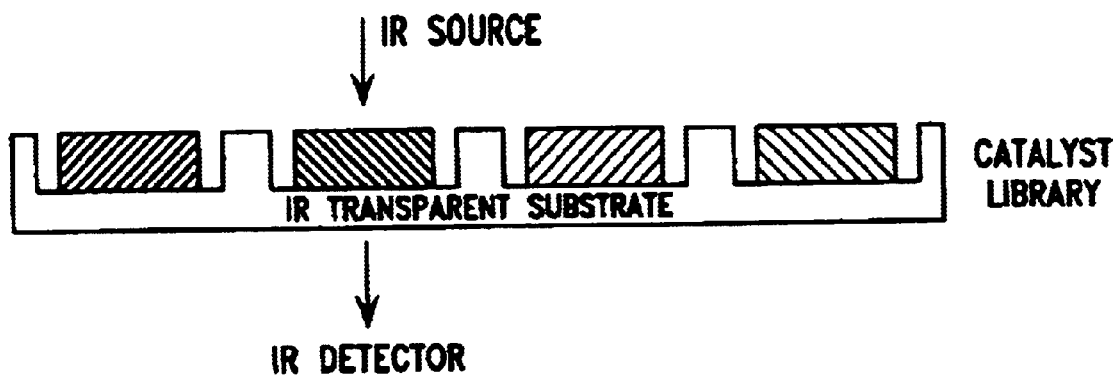
FIG. 22 illustrates a system employing infrared absorption.

In a typical embodiment, an infrared source monochromated to the desired wavelength using selective filtering is passed through the library and the intensity of the transmitted beam is measured as a function of time during the progression of the reaction. The source can be directed through individual library elements one-by-one in serial fashion as depicted in FIG. 22, or a large area source beam can be passed through the entire library and a position sensitive IR detector, such as HgCdTe or InSb, can be used to monitor an infrared transmission image as a function of time giving a parallel measurement. Reflectance mode measurements may also similarly be performed.

Figure 26:
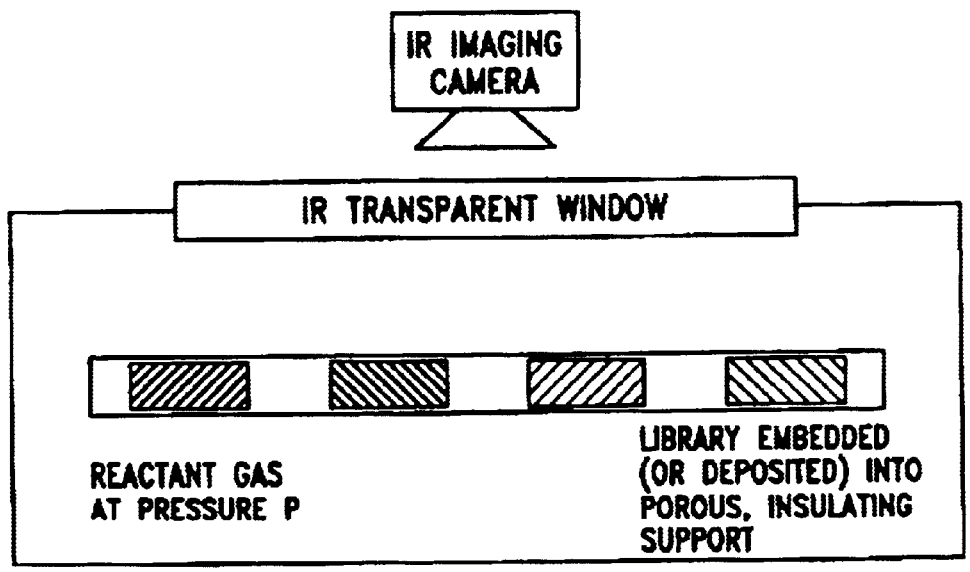
FIG. 26 illustrates a system using a PZT pads which are attached to or deposited directly under the individual library elements.

Using a large area infrared source achieved either with a beam expander (IR laser) or a bandpass filtered lamp source the entire library may be illuminated simultaneously and using a focal plane array or similar array detector the IR reflectance or transmissions monitored in parallel fashion. Furthermore, as described below in more detail (part C) for gas phase catalysis, the heat of reaction as measured by temperature changes can be used as a screening method of catalytic rate. Though insensitive to specific products, when activity is of interest, this method gives a parallel high throughput screen. Condensed phase products will be in thermal contact with the catalyst and infrared emission imaging of the library elements as depicted in FIG. 26 provides a unique means of screening large libraries in parallel.

For rapid throughput screening, the relative differences in temperature change between library elements is satisfactory, and only those elements with relatively large temperature changes need to be more carefully examined with high activity catalysts are the target. If large differences in emissivity are observed for individual library elements, then the imaging can be done of the uniform substrate in thermal contact with the catalyst and support.

Figure 23:
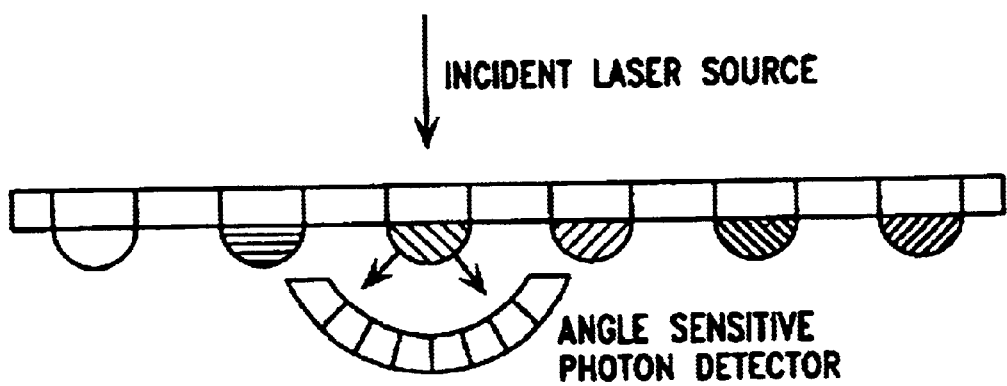
FIG. 23 illustrates a system employing an infrared imaging camera to measure infrared emissions.

(ii) Photon Scattering Analysis:

Light scattering from condensed phase polymers and suspensions is a well established method of materials analysis. A unique implementation of photon scattering has been created whereby relative and time varying differences in the molecular weight distribution and average molecular weight of a library of catalysts for liquid products and reactants are monitored by changes in the relative intensity of scattered light measured as a function of angle relative to the incident beam (see, FIG. 23). A photodiode array positioned around a library element is used to collect the scattered light intensity as a function of angle relative to the incident laser. The library is scanned relative to the laser-detector subassembly for the purpose of mapping the property as a function of position on the library. Several sweeps of the library can be used to characterize the temporal changes in the scattered light distribution to follow, for example, rate of polymerization.

Although precise quantitative determination of the Rayleigh ratio and average molecular weight requires careful design of the scattering cell geometry (usually cylindrical), for relative measurements, more convenient practical configurations can be used. Similarly, precise work using only small angle scattering allows simplification of the scattering-function and use of the straight-forward Debye equation to determine accurately average molecular weights, however, since for library screening relative changes are desired to choose compounds for more precise secondary characterization larger angle scattering may be used.

(iii) Polarized Light Imaging:

The formation of optically active crystalline domains in solids can give rise to optical rotation and/or preferential transmission of polarized light. Using the schematic diagram of the IR system described above and illustrated in FIG. 17, except replacing the IR source and detector with a polarized light source and a polarized light detector, or by transilluminating an entire library with polarized light and then imaging the transmitted light onto a CCD through a polarizer, characterization of the relative changes in orientational order can be monitored in real time to observe the rate of polymerization in many important polymer systems.

2. Condensed Phase Product Characterization by Mechanical is Properties (i) Ultrasonic Monitoring:

Catalysis of reactions producing liquid or solid products are monitored and characterized by changes in mechanical properties of the products measured by ultrasonic probing. The velocity of acoustic waves is equal to the square root of the ratio of a material's bulk modulus to its density. Although both density and modulus may change during the formation of products, monitoring the ratio in every element of a combinatorial library allows the direct comparison of relative rates of reaction and gives information regarding the molecular weight distribution. Measurement of the surface acoustic wave velocity is also possible by acoustic monitoring (Rayleigh Waves). The Rayleigh wave velocity gives a measure of the Poisson ratio of the material which together with the bulk modulus completely determines the mechanical properties of a solid material. Therefore, acoustic characterization not only measures changes in properties relevant for polymerization and other catalytic processes, it also measures the important mechanical properties of the resulting material and is a well known method of characterizing materials.

Figure 24:
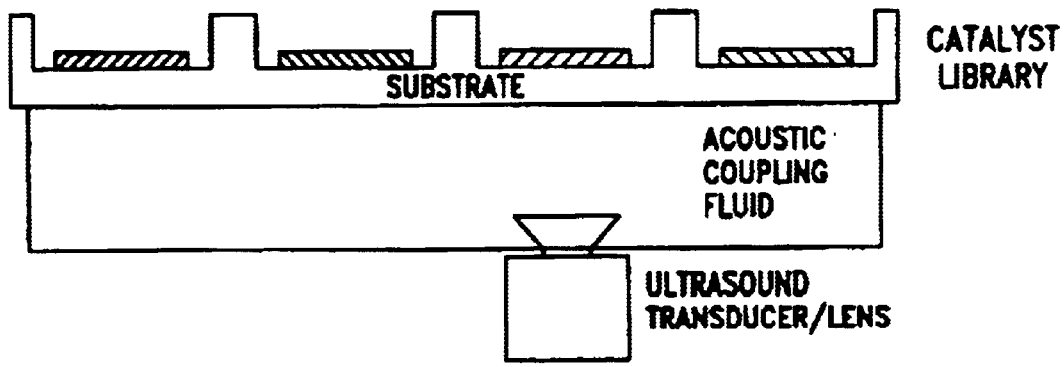
FIG. 24 illustrates a system for detecting photon scattering.

Two different embodiments of acoustic monitoring to combinatorial library characterization are provided. The first embodiment, illustrated in FIG. 24, uses an ultrasonic imaging transducer-lens system coupled through a coupling medium (e.g., water, mercury, etc.) to the base of a combinatorial library containing catalyst. There can be an array of many transducer-lens systems or a single transducer-lens that is scanned across the base of the library.

Figure 25:
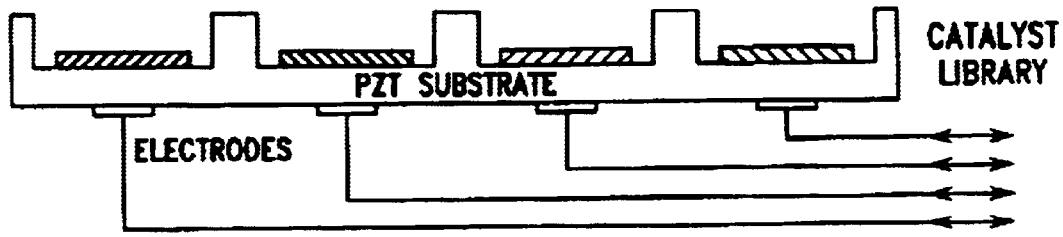
FIG. 25 illustrates a system for ultrasonic monitoring.

The second embodiment consists of a piezoelectric transducer (PZT) array (either separate or incorporated into the library substrate), with each element of the PZT array directly adjacent to a library element. The PZT element serves as both the transmitter of acoustic energy and the receiver. Monitoring of the acoustic velocities requires only multiplexing the array for serial readout. Two, slightly different, integrated designs would have the substrate itself be a PZT material with electrodes attached directly under each library element, or with the PZT pads attached or deposited directly under the individual library elements. The latter implementation is illustrated in FIG. 25.

D. Measurement of Physical Properties of the Catalyst Library

1. Characterization by Heat of Reaction:

(i) Two-dimensional Infrared Imaging for Parallel Monitoring of Catalyst Library Heat of Reaction:

An alternative method presented for monitoring the rate of reaction of all the elements in the library simultaneously relies on the heat of reaction to alter the temperature of the solid catalyst and surrounding support and to monitor the temperature with a two-dimensional infrared imaging camera. In the condensed phase detection system described above, the products, catalyst and support will all change temperature; however, in the gas phase, the temperature variation is limited to the catalyst and support. The individual library element's temperature (and its difference relative to the surrounding elements), will reflect the activity of the specific library site and the heat of reaction. The catalyst support should have a minimal thermal mass and it is assumed each library element contains nearly identical catalyst surface area. One configuration of this method is depicted in FIG. 26.

The measurement begins, in one example, with the sample chamber, library and structure equilibrated uniformly at the temperature of the activity measurement. An inert gas may fill the chamber at the experimental pressure initially or it may be evacuated or it may be in another initial state. At t=0, the desired reactant gas is leaked into the chamber and the substrate temperature is measured continuously at intervals. The rise (or fall) in temperature of the thermal mass supporting the catalyst will be a direct measure of the exothermic (endothermic) catalytic activity of the site.

The sensitivity of most commercial infrared detection arrays (e.g., HgCdTe or InSb) is better than +/−0.05° C. over the range of −50 to +800° C. and the spatial resolution is determined by the optics to be better than 1 mm. As an estimate of the temperature change expected, if there is a microjoule deposited in a 1 mm×1 mm×0.0001 mm region of material, a temperature change of approximately 0.5 K is expected. The reaction of ethylene and hydrogen to ethane produces 120 KJ/mole and, therefore, 1 microjoule requires only the reaction of $5 \times 10^{12}$ molecules. Many times that number will react in a second on a 1 mm×1 mm×0.0001 mm porous support for most important industrial catalysts or on a non-porous 1 mm×1 mm×0.000001 mm film. In a less preferred embodiment, individual elements can be monitored in series using non-position sensitive temperature detection technology or single element scanned detectors.

The present invention is directed to the synthesis of supported and unsupported ligand molecules and their subsequent conversion to organometallic and catalyst compounds. In the examples which follow, the synthesis of two representative calsses of ligands, diimines and pyridylimines, using the methods of the invention are detailed. Representative examples using both solution- and solid-phase methodologies are provided. The use of these two broad ligand classes to further describe the invention is intended to be exemplary and is not intended to define or limit the scope of the invention or of the ligands, organometallic compounds or catalysts which can be assembled using the methods of the instant invention.

IV. EXAMPLES

The following examples illustrate a variety of embodiments of the present invention. Example 1 illustrates the solution-phase synthesis of bis-imine ligands. Example 2 illustrates the concept of solid phase combinatorial synthesis of diimine ligands. Example 3 illustrates the application of the methods of the present invention to the solid phase synthesis of diimine ligands, wherein the diimine is synthesized on the support. Example 4 illustrates the utility of the catalysts of the present invention in polymerizing olefins. Both the supported and unsupported catalysts of the invention were assayed for their ability to polymerize ethylene to poly(ethylene). The polymerization of higher olefins such as hexene was also examined. Example 5 details the preparation of a pyridyl imine ligand and its nickel complex. The catalyst was used to polymerize both hexene and ethylene. Example 6 illustrates reaction schemes which can be used to prepare a variety of [2,0], [2,1], and [2,2] ligand libraries. Such [2,0], [2,1], and [2,2] ligand libraries can be prepared using solution or solid phase methodologies from a salen-based scaffold.

Example 1

Example 1 details the solution-phase synthesis of bis-imine ligand components of a combinatorial library of ligands. General strategies were developed for aryl bis-imines with both electron-donating and electron-withdrawing groups on the aryl moiety.

1 1.1 Synthesis of [(2,4,6-Me$_3$Ph)DABMe$_2$]NiBr$_2$ Through Solution-Phase Methodology a. Synthesis of Resin-Bound Lewis-Acid Catalyst P—CH$_2$—O—TiCl$_3$ To 10 g hydroxymethylpolystyrene (1.12 mmol OH/g resin) swollen in 100 mL of anhy. CH$_2$Cl$_2$ was added 4.24 g (2.24 mmol) TiCl$_4$, and this suspension was heated to reflux under N$_2$ with gentle stirring for 1 h. The resin was filtered under N$_2$, washed with 5×50 mL anhy. CH$_2$Cl$_2$ and then dried under high vacuum for 24 h. Chloride analysis (9.98%) provided a loading of 0.94 mmol TiCl$_3$/g resin.

b. Synthesis of Aniline Scavenging Reagent PS—SO$_2$Cl

To 10 g of PS—SO$_2$—OH (Amberlyst 15, washed with MeOH and dried in vacuo; ca. 5 mmol OH/g resin) in 50 mL of anhy. CH$_2$CL$_2$ was added 3 g (25 mmol) of SOCL$_2$. This mixture was heated at reflux under N$_2$ for 18 h. The resin was filtered under N$_2$, washed with 5×50 mL of anhy. CH$_2$Cl$_2$, then dried under high vacuum for 24 h. Chloride analysis (16.05%) provided a loading of 4.53 mmol SO$_2$Cl/g resin.

c. Ligand Synthesis

To a suspension of 250 mg (0.24 mmol) of PS—CH$_2$—OTiCl$_3$ and 93 mg (0.25 mmol) PS—CH$_2$-piperidine in 5 mL of anhy. CH$_2$Cl$_2$ was added 676 mg (0.5 mmol) of 2,4,6-trimethylaniline followed by 8.6 mg (0.1 mmol) 2,3-butanedione. This mixture was shaken at RT for 24 h. then filtered and washed with 2×1 mL anhy. CH$_2$Cl$_2$. GC analysis showed 2,4,6-trimethylaniline and the product (2,4,6-Me$_3$Ph)DABMe$_2$ in an approximately 3:1 ratio.

d. Excess Aniline Scavenging

To the 3:1 mixture of 2,4,6-trimethylaniline and (2,4,6-Me$_3$Ph)DABMe$_2$ was added 111 mg of PS—SO$_2$Cl and 185 mg of PS—CH$_2$-piperidine and this mixture shaken at RT for 12 h. The resin was filtered and washed with 2×0.5 mL CH$_2$Cl$_2$. The filtrate was evaporated to provide 285 mg (89%) of (2,4,6-Me$_3$Ph)DABMe$_2$ as yellow crystals.

e. Synthesis of [(2,4,6-Me$_3$Ph)DABMe$_2$]NiBr$_2$ Complex

A suspension of 285 mg (0.89 mmol) of (2,4,6-Me$_3$Ph)DABMe$_2$ and 274 mg (0.89 mmol) (DME)NiBr$_2$ in 5 mL CH$_2$Cl$_2$ was shaken in a sonication bath at RT for 24 h. The resultant solid was collected by filtration and washed with 3×1 mL CH$_2$Cl$_2$ to provide 456 mg (95%) [(2,4,6-Me$_3$Ph)DABMe$_2$]NiBr$_2$ as a red powder.

1.2 Preparation of (2,4,6-Me)$_2$DAB(Me)EtPh Nickel (II) Dibromide

Scheme 4

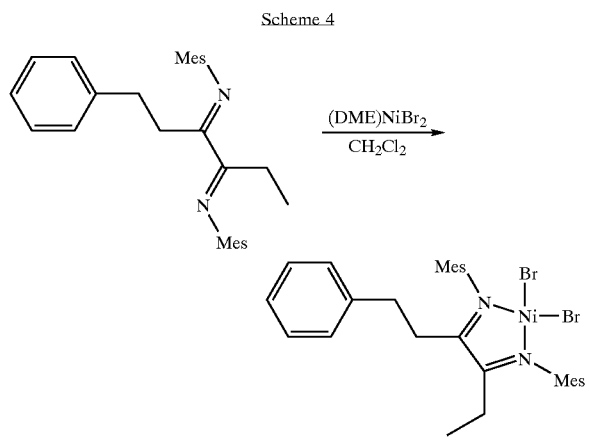

(2,4,6-Me)$_2$DAB(Me)EtPh (0.50 g, 1.17 mmol) and (DME)NiBr$_2$ (0.36 g, 1.17 mmol) were dissolved in 8 ml dry CH$_2$Cl$_2$ under nitrogen and stirred at room temperature for 8 hr. The resulting reddish-brown solution was concentrated and the remaining residue was recrystallized from CH$_2$Cl$_2$/hexane to afford 0.40 g of (2,4,6-Me)$_2$DAB(Me)EtPh nickel (II) dibromide as reddish-brown crystals in 53% yield. Anal. Cald for C$_{30}$H$_{36}$N$_2$NiBr$_2$: C 55.88; H 5.62; N 4.34. Found: C 55.08; H 5.55; N 4.21.

1.3 Solution-Phase Synthesis (Spectroscopic Model Compounds)

Compounds with all of the structural features of the immobilized compounds are prepared in tandem with the immobilized compounds. The model compounds allowed the proper spectroscopic parameters to be determined for the immobilized analogues. Additionally, these compounds have a catalytic activity which is similar to that exhibited by the analogous immobilized metal-ligand compounds.

1.3(a) Alkylation of (2,4,6-Me)$_2$DAB(Me)Et with Benzyl Bromide

Scheme 5

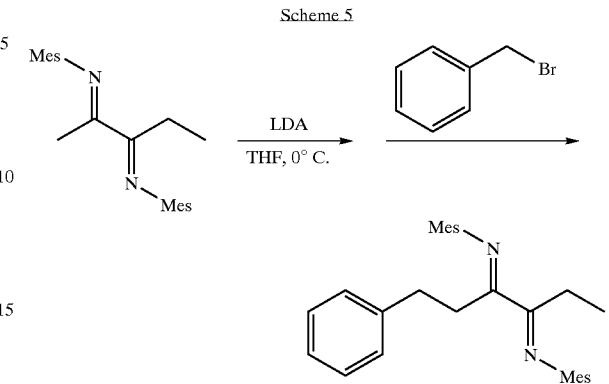

To a cooled solution (0° C.) of (2,4,6-Me)$_2$DAB(Me)Et (2.00 g, 5.99 mmol) in 15 ml dry THF under nitrogen was added LDA (4.40 ml, 6.59 mmol, 1.5 M in THF). After stirring at 0° C. for 2 hr, benzyl bromide (0.86 ml, 7.19 mmol) was added and the resulting solution was stirred 3 hr at 0° C. and 10 hr at room temperature. The reaction mixture was concentrated on a rotovap and the remaining oily residue was taken up in 50 ml Et$_2$O and washed with H$_2$O (2×50 ml). The Et$_2$O layer was dried over MgSO$_4$, filtered and concentrated. The crude material was passed through a plug of silica gel with CH$_2$Cl$_2$ and concentrated once more to afford 2.54 g of the desired product in 95% yield as a yellow oil. $^1$H NMR 300 MHz, (CDCl$_3$) δ 7.23–7.28 (m, 3H), 7.19 (d, 2H, J=6.9 Hz), 6.98 (s, 2H), 6.94 (s, 2H), 2.87 (br s, 4H), 2.64 (q, 2H, J=7.6 Hz), 2.37 (s, 3H), 2.35 (s, 3H), 2.14 (s, 6H), 2.06 (s, 6H), 1.12 (t, 3H, J=7.6 Hz); $^{13}$C NMR 75 MHz, (CDCl$_3$) δ 171.97, 169.97, 145.85, 145.56, 141.15, 132.28, 132.20, 128.66, 128.28, 128.15, 125.97, 124.37, 32.76, 31.28, 22.24, 20.67, 18.22, 18.06, 11.24; IR (C═N) @ 1635 cm$^{-1}$.

1.3(b) Hydrolysis of Benzyl (2,4,6-Me)$_2$DAB(Me)Et (Methyl)

Scheme 6

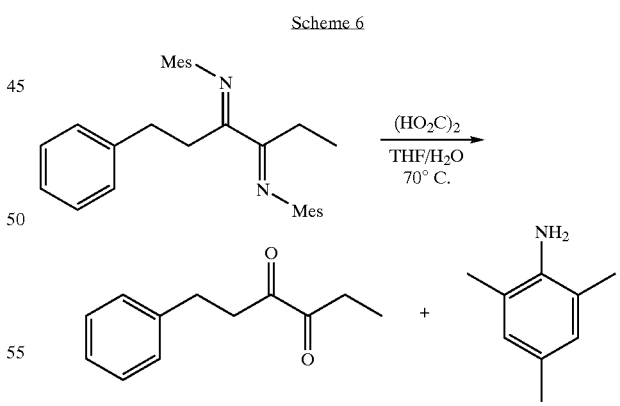

A stirring solution of benzyl (2,4,6-Me)$_2$DAB(Me)Et (0.20 g, 0.47 mmol) and oxalic acid (0.20 g, 2.35 mmol) in 10 ml THF/H$_2$O (5:1 v/v) was heated to 70° C. for 8 hr. After cooling to room temperature and diluting with 30 ml Et$_2$O, the organic layer was washed with H$_2$O (2×10 ml), dried over MgSO$_4$, filtered and concentrated. GC/MS analysis revealed 1-phenyl-3,4-hexanedione and 2,4,6-trimethylaniline as the only detectable species in the crude reaction mixture. Pure 1-phenyl-3,4-hexanedione (89 mg)

was obtained by passing the crude mixture through a plug of silica gel in >95% yield as a colorless oil. $^1$H NMR 300 MHz, (CDCl$_3$) δ 7.20–7.31 (m, 5H), 3.14 (t, 2H, J=7.6 Hz), 3.01 (t, 2H, J=7.4 Hz), 2.75 (q, 2H, J=6.7 Hz), 1.07 (t, 3H, J=6.6 Hz); $^{13}$C NMR 75 MHz, (CDCl$_3$) δ 199.44, 198.25, 140.19, 128.20, 128.06, 125.94, 37.34, 29.10, 28.67, 6.53; IR (C=O) @ 1712 cm$^{-1}$.

1.3(c) Alkylation of (2,4,6-Me)$_2$DAB(Me)Et with 1-(Bromoethyl)-2-Methoxyethane

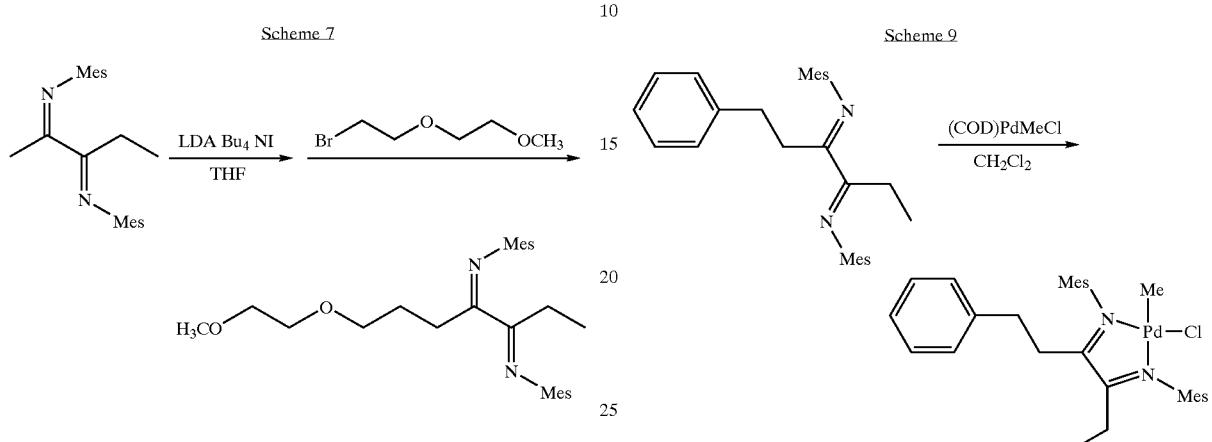

To a cooled solution (0° C.) of (2,4,6-Me)$_2$DAB(Me)Et (0.50 g, 1.48 mmol) in 15 ml dry THF under nitrogen was added LDA (1.09 ml, 1.65 mmol, 1.5 M in THF). After stirring at 0° C. for 4 hr, 1-(bromoethyl-2-methoxyethane (0.24 ml g, 0.1.79 mmol) was added with Bu$_4$NI (0.27 g, 0.75 mmol) and the reaction mixture was warmed to 50° C. and stirred for 10 hr. After cooling to room temperature, the reaction mixture was diluted with 30 ml Et$_2$O and washed with H$_2$O (3×15 ml), dried over MgSO$_4$, filtered and concentrated on a rotovap. The crude product was chromatographed with 20% Et$_2$O/hexane (R$_f$=0.45) to afford 0.93 g of the desired product as a yellow oil in 45% yield. $^1$H NMR 300 MHz, (CDCl$_3$) δ 6.81 (s, 2H), 3.33 (s, 4H), 3.25–3.32 (m, 2H), 3.23 (s, 3H), 2.41–2.47 (m, 4H), 2.20 (s, 6H), 1.94 (s, 12H), 1.54–1.69 (m, 2H), 0.94 (t, 3H, J=7.5 Hz). $^{13}$C NMR 75 MHz (CDCl$_3$) δ 171.97, 170.35, 145.65, 145.52, 132.15, 128.56, 128.53, 124.36, 71.72, 70.95, 69.48, 58.89, 27.33, 25.51, 22.19, 20.61, 18.06, 11.11.

1.3(d) Preparation of (2.4.6-Me)$_2$DAB(1-Methoxyethoxyethyl)Et Nickel (II) Dibromide Scheme 8

(2,4,6-Me)$_2$DAB(1-methoxyethylpropyloxy) ethane (0.29 g, 0.67 mmol) and (DME) NiBr$_2$ (0.21 g, 0.67 mmol) were taken up in 6 ml dry CH$_2$Cl$_2$ under nitrogen and stirred at room temperature for 24 hours. The reaction mixture was filtered through celite and concentrated to afford crude (2,4,6-Me)$_2$DAB(1-methoxyethoxypropyl)ethyl nickel (II) dibromide which was purified through recrystallization from CH$_2$Cl$_2$/hexane to afford 0.35 g of pure product as a reddish-brown solid in 80% yield. Anal. Cald for C$_{28}$H$_{40}$N$_2$O$_2$NiBr$_2$: C 51.33; H 6.15; N 4.27. Found: C 52.01; H6.26; N 3.91.

1.3(e) Preparation of (2,4,6-Me)$_2$DAB(Me)EtPh Palladium (II) (Me)Cl

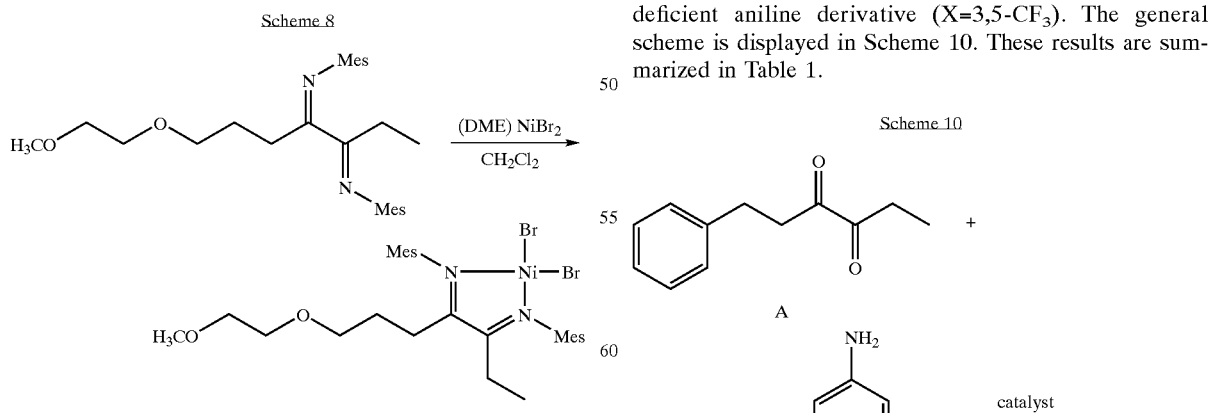

(2,4,6-Me)$_2$DAB(Me)EtPh (0.23 g, 0.65 mmol) and (COD)PdMeCl (0.17 g, 0.65 mmol) were dissolved in 8 ml dry CH$_2$Cl$_2$ under nitrogen and stirred at room temperature for 8 hr. The resulting orange-red solution was concentrated and the remaining residue was recrystallized from CH$_2$Cl$_2$/hexane to afford 0.30 g of (2,4,6-Me)$_2$DAB(Me)EtPh palladium (II) (Me)Cl as a orange solid in 80% yield. Anal. Cald for C$_{31}$H$_{39}$N$_2$PdCl: C 64.02; H 6.76; N 4.81. Found: C 63.47; H 6.70; N 4.62.

1.4 Solution-Phase Combinatorial Synthesis

Catalytic bis-imine formation generally works well for aniline derivatives containing electron donating groups (X=EDG). However, anilines containing electron withdrawing groups (X=EWG) are much less nucleophilic and bis-imine formation is not observed under standard conditions (Entry 1, Table 1). Therefore, conditions were sought to initiate bis-imine formation with a representative electron deficient aniline derivative (X=3,5-CF$_3$). The general scheme is displayed in Scheme 10. These results are summarized in Table 1.

-continued

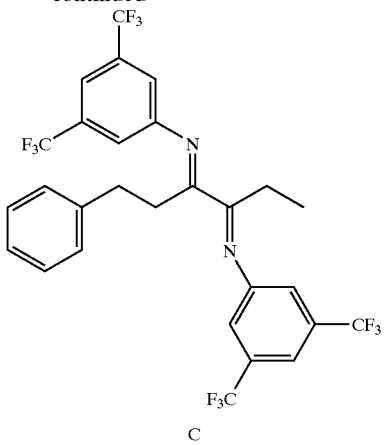

C

TABLE 1

| Entry | A Equiv. | B Equiv. | Catalyst (Equiv.) | Conditions | C Yield (GC/MS) |
|---|---|---|---|---|---|
| 1 | 1 | 20 | HCO$_2$H (10) | CH$_2$Cl$_2$/MeOH RT, 12 hr. | 0% |
| 2 | 1 | 20 | H$_2$SO$_4$ (10) | CH$_2$Cl$_2$/MeOH RT, 12 hr. | 20% |
| 3 | 1 | 20 | (CO$_2$H)$_2$ (10) | CH$_2$Cl$_2$/MeOH RT, 12 hr. | 65% |
| 4 | 1 | 10 | (CO$_2$H)$_2$ (10) | (CH$_8$O)CH 70° C., 12 hr. | 0% |
| 5 | 1 | 20 | (CO$_2$H)$_2$ (10) | Si(OEt)$_4$ RT, 12 hr. | 60% |
| 6 | 1 | 13 | TiCl$_4$ (2) | CH$_2$Cl$_2$ RT, 12 hr. | 80% |
| 7 | 1 | 15 | TiCl$_4$ (5) | CH$_2$Cl$_2$ RT, 12 hr. | 95% |

Example 2

Example 2 illustrates the concept of solid phase combinatorial synthesis of diimine ligands. Through the approach outlined below, alkylation of a diimine ligand with 1% cross-linked (bromomethyl)polystyrene is carried out. The supported diimine is hydrolyzed to give the corresponding resin bound diketone which serves as starting material for synthesizing a broad range of chemically diverse bis-imine ligands. The analogous solution-phase reactions are performed in parallel and are fully characterized spectroscopically and serve to provide spectroscopic handles ($^1$H and $^{13}$C NMR, FTIR, Raman IR) to help facilitate the characterization of the desired resin bound compounds.

2.1 Solid Phase Combinatorial Strategy

This approach involves the parallel synthesis of organometallic libraries immobilized on a polymer support. Advantages to this approach include exposing a large excess of the reagents to immobilized substrates and effectively driving reactions to completion. Excess reagents and/or side products are then removed from the desired immobilized substrate by filtration followed by extensive washings.

2.2 Preparation of (Bromomethyl)Polystyrene

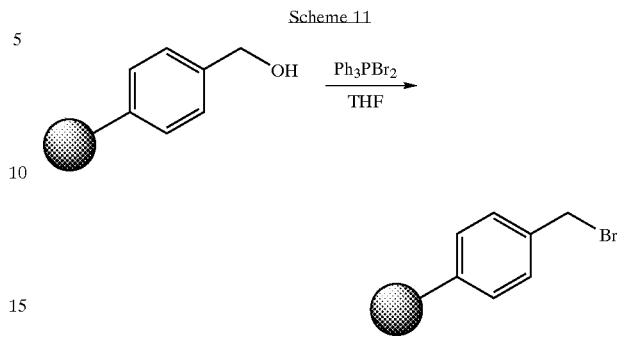

Scheme 11

(Hydroxymethyl)polystyrene (2.50 g, 2.84 mmol, 0.80 mmol/g) and triphenylphosphinedibromide (2.40 g, 5.68 mmol) were combined under nitrogen and 20 ml of dry THF was added. After stirring at room temperature for 24 hr, the resin was filtered and washed extensively with THF (3×20 ml), DMF (3×20 ml), CH$_2$Cl$_2$ (3×20 ml), and dried under high vacuum to afford 2.75 g of (bromomethyl)polystyrene as a beige resin. A loading capacity of 0.58 mmol/g was calculated based on bromide analysis (4.65% Br).

2.3 Alkylation of (2,4,6-Me)$_2$DAB(Me)Et with (Bromomethyl)Polystyrene

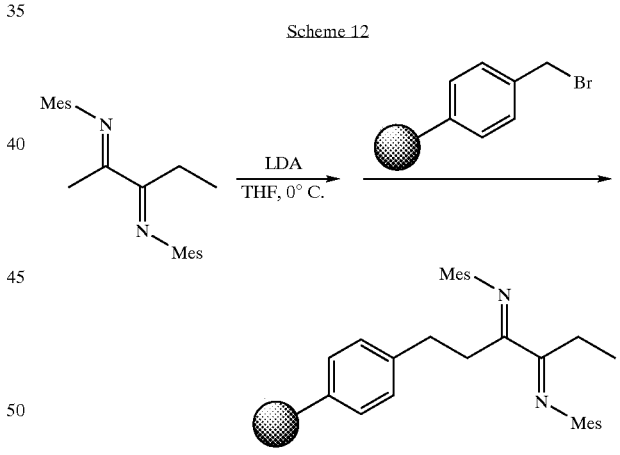

Scheme 12

To a cooled solution (0° C.) of (2,4,6-Me)$_2$DAB(Me)Et (0.50 g, 1.49 mmol) in 15 ml dry THF under nitrogen was added LDA (1.09 ml, 1.49 mmol, 1.5 M in THF). After stirring at 0° C. for 2 hr, (bromomethyl)polystyrene (1.06 g, 0.75 mmol) was added and the resulting suspension was stirred for 3 hr at 0° C. and 10 hr at room temperature. The resin was filtered, washed with THF (2×10 ml), H$_2$O (2×20 ml), CH$_2$Cl$_2$ (2×20 ml), and dried under high vacuum to afford 0.60 g of the desired bright yellow resin. The loading capacity of this resin was calculated to be 0.38 mmol/g based on nitrogen analysis (1.07% N). A strong absorbance at 1635 cm$^{-1}$ (C=N) is observed by single bead FTIR.

2.4 Hydrolysis of (2,4,6-Me)$_2$DAB(Me)Et (Methyl) Polystyrene

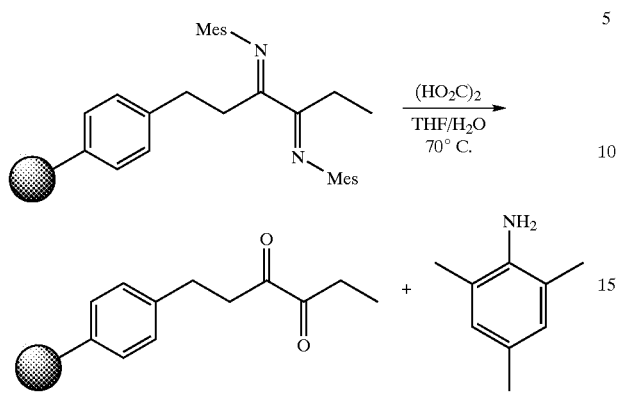

Scheme 13

A stirring suspension of (2,4,6-Me)$_2$DAB(Me)Et (methyl) polystyrene (1.0 g, 0.38 mmol) and oxalic acid (340 mg, 3.80 mmol) in 17 ml THF/H$_2$O (5:1 v/v) was heated to 70° C. for 12 hr. After cooling to room temperature and diluting with 30 ml Et$_2$O, the resin was filtered and the filtrate was washed with H$_2$O (2×10 ml), dried over MgSO$_4$, filtered and concentrated to give 24 mg of 2,4,6-trimethylaniline in 98% yield with was >99% pure by GC/MS analysis and $^1$H NMR. The beads were dried under high vacuum to give 850 mg of (2,3-butanedionemethyl)polystyrene. A strong absorbance at 1712 cm$^{-1}$ (C=O) is observed by single bead FTIR.

2.5 Alkylation of (2,4,6-Me)$_2$DAB(Me)Et with (Bromo) PEG Polystyrene

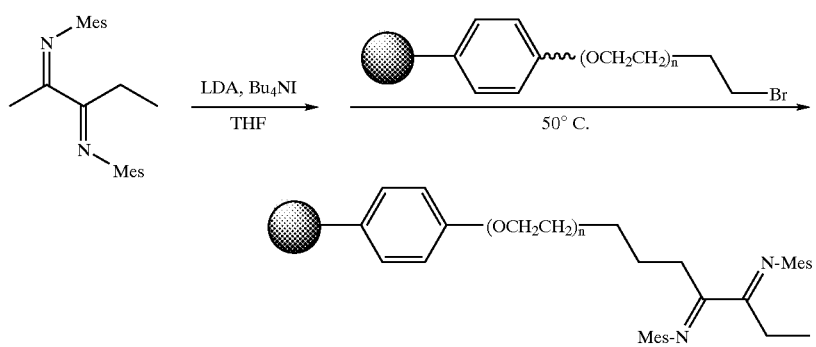

Scheme 14

To a cooled solution (0° C.) of (2,4,6-Me)$_2$DAB(Me)Et (0.70 g, 2.09 mmol) in 15 ml dry THF under nitrogen was added LDA (1.63 ml, 2.44 mmol, 1.5 M in THF). After stirring at 0° C. for 4 hr, (bromo) PEG polystyrene (2.33 g, 0.70 mmol, 0.30 mmol/g) and Bu$_4$NI (0.77 g, 2.09 mmol) were added and the reaction mixture was warmed to 50° C. and stirred an additional 8 hr after which the resin was filtered and washed extensively with THF (3×20 ml), H$_2$O (3×20 ml), and MeOH (3×20 ml). After drying under high vacuum, 2.37 g of (2,4,6-Me)$_2$DAB(Me)Et (bromo)PEG polystyrene was obtained as a yellow resin. A loading capacity of 0.25 mmol/g was calculated based on nitrogen analysis (0.71% N). Magic angle spin (MAS) $^1$H NMR 400 MHz, (CDCl$_3$) δ 6.87 (br s, 2H), 3.51 (br s, 2H), 2.76 (br s, 2H), 2.51 (d, 2H, J=7.6 Hz), 2.28 (s, 6H), 2.01 (s, 12 H), 1.74 (br s, 2 H). 1.03 (t, 3H, J=6.8 Hz).

2.6 Hydrolysis of (2,4,6-Me)$_2$DAB(Me)Et PEG Polystyrene

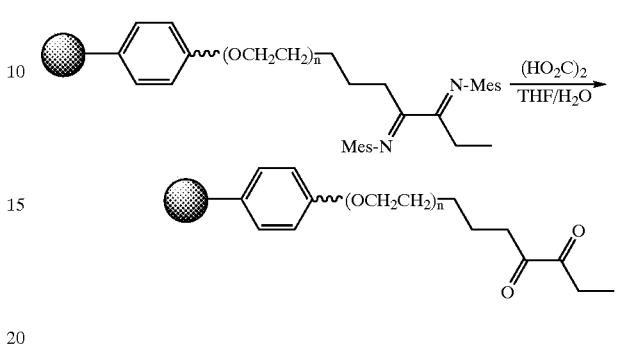

Scheme 15

(2,4,6-Me)$_2$DAB(Me)Et PEG polystyrene (0.50 g, 0.12 mmol, 0.25 mmol/g) and oxalic acid (0.10 g, 1.12 mmol) was taken up in 20 ml THF/H$_2$O (5:1 v/v) and heated to 70° C. with gentle stirring for 8 hr. After cooling to room temperature and diluting with 25 ml Et$_2$O, the resin was filtered and the filtrate was washed with H$_2$O (2×10 ml), dried over MGSO$_4$, filtered and concentrated to give 16 mg of 2,4,6-trimethylaniline in quantitative yield which was >99% pure by GC/MS analysis and $^1$H NMR. The beads were dried under high vacuum to afford 450 mg of beige 2,3-butanedinone PEG resin. Magic angle spin (MAS) $^1$H NMR 400 MHz, (CDCl$_3$) δ 2.80 (m, 2H), 1.90 (m, 2H), 1.08 (t, 3H, J=6.8 Hz).

2.7 Preparation of (2,4,6-Me)$_2$DAB(Me)Et Nickel (II) Dibromide PEG Polystyrene Scheme 16

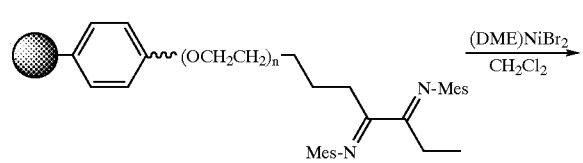

-continued

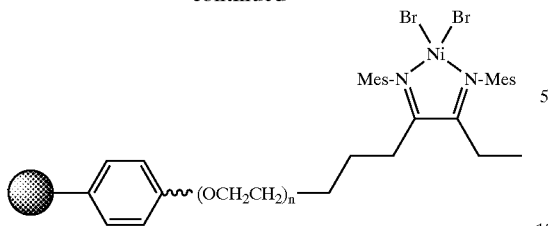

(2,4,6-Me)$_2$DAB(Me)Et PEG polystyrene (0.40 g, 0.10 mmol, 0.25 mmol/g) and (DME)NiBr$_2$ (0.15 g, 0.50 mmol) were taken up in 10 ml dry CH$_2$Cl$_2$ under nitrogen and stirred at room temperature for 12 hr. The resin was then washed extensively with CH$_2$Cl$_2$ and anhydrous acetone to give 0.42 g of (2,4,6-Me)$_2$DAB(Me)Et nickel (II) dibromide PEG polystyrene as a dark reddish-brown resin. The loading capacity of this resin was calculated to be 0.54 mmol/g based on nickel analysis (3.40% Ni) and 0.57 mmol/g based on bromine analysis (8.67% Br), indicating that some residual nickel (II) dibromide was coordinated to the PEG polystyrene backbone.

2.8 Preparation of (2,4,6-Me)$_2$DAB(Me)Et Palladium (II) (Me)Cl PEG Polystyrene Scheme 17

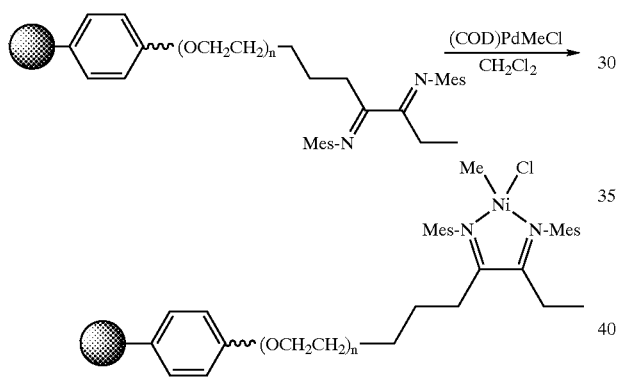

(2,4,6-Me)$_2$DAB(Me)Et PEG polystyrene (0.50 g, 0.12 mmol, 0.25 mmol/g) and (COD)PdMeCl (0.16 g, 0.63 mmol) were taken up in 7 ml dry CH$_2$Cl$_2$ under nitrogen and stirred at room temperature for 12 hr. The resin was then washed extensively with CH$_2$Cl$_2$ to give 0.51 g of (2,4,6-Me)$_2$DAB(Me)Et Pd (II) (Me)Cl PEG polystyrene as a reddish-orange resin. Magic angle spin (MAS) $^1$H NMR 400 MHz, (CDCl$_3$) δ 6.97 (br s, 2H), 6.92 (br s, 2H), 2.75 (br s, 2H), 2.45 (br s, 2H)), 2.32 (s, 3H), 2.30 (s, 3H), 2.24 (s, 6H), 2.21 (br s, 6H), 1.62 (br s, 2H), 1.03 (br s, 3H), 0.36 (s, 3H).

2.9 Preparation of (2,4,6-Me)$_2$DAB(Me)Et Palladium (II) (ME)Cl Polystyrene

Scheme 18

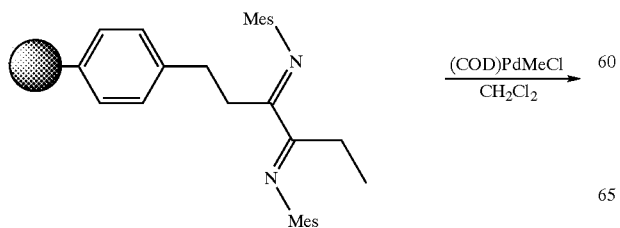

-continued

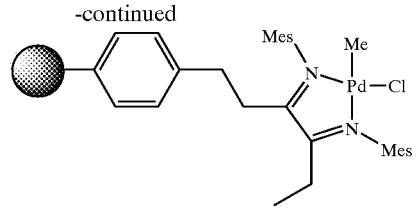

(2,4,6-Me)$_2$DAB(Me)Et polystyrene (0.30 g, 0.11 mmol, 0.38 mmol/g) and (COD) PdMeCl (0.15 g, 0.57 mmol) were combined under nitrogen and taken up in 8 ml dry CH$_2$Cl$_2$. After stirring for 10 hr, the resin was washed extensively with CH$_2$Cl$_2$ and dried under high vacuum to afford 0.32 g of (2,4,6-Me)2DAB(Me)Et palladium (II) (ME)Cl polystyrene as a reddish-orange resin. The loading capacity of this resin was calculated to be 0.32 mmol/g based on palladium analysis (4.15% Pd) and 0.39 mmol/g based on chlorine analysis (3.39% Cl).

Example 2 demonstrates the synthesis of representative diimine ligands utilizing the solid phase combinatorial methods of the present invention. The diimines of Example 2 were synthesized off of the support and subsequently attached to the support prior to undergoing additional modification. Following hydrolysis of the support-attached diimines, a diketone was produced which was utilized for preparation of additional diimine ligands.

Example 3

Example 3 illustrates the application of the methods of the present invention to the solid phase synthesis of diimine ligands, wherein the diimine is synthesized on the support.

3.1 Solid-Phase Bis-imine Formation

Scheme 19

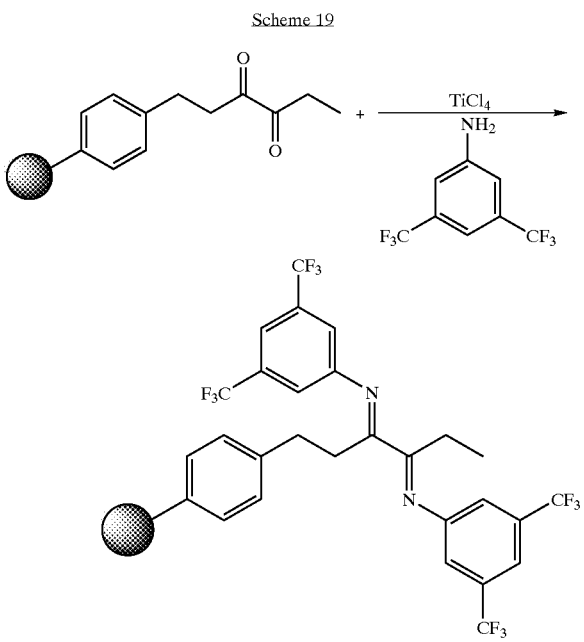

To a suspension of 2,3 butanedione (methyl)polystyrene (0.10 g, 0.08 mmol) in 5 ml of dry CH$_2$Cl$_2$ was added 3,5-bis(trifluoromethyl)aniline (0.25 ml, 1.60 mmol) and TiCl$_4$ (0.80 ml, 0.80 mmol, 1.0 M in CH$_2$Cl$_2$). The mixture was stirred at room temperature for 24 hr upon which the resin was filtered and washed extensively with CH$_2$Cl$_2$ (3×10 ml), MeOH (3×10 ml), H$_2$O (3×10 ml), and dried under high vacuum to give 0.11 g of the desired resin. The loading capacity of this resin was calculated to be 0.15 mmol/g based on nitrogen analysis (0.43% N).

Example 3 demonstrated that diimines can be formed directly on a resin which has been functionalized with a diketone.

Example 4

Example 4 illustrates the utility of the catalysts of the present invention in polymerizing olefins. Both the supported and unsupported catalysts of the invention were assayed for their ability to polymerize ethylene to poly (ethylene). The polymerization of higher olefins such as hexene was also examined.

4.1 Polymerization of Ethylene

Scheme 20

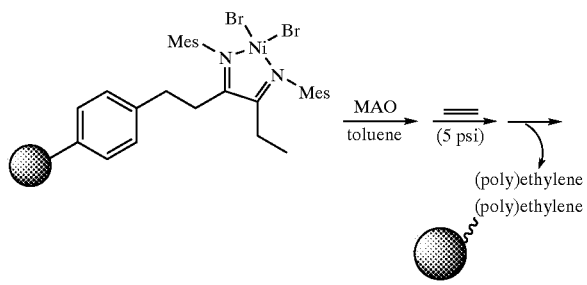

The above resin-bound nickel(II) dibromide complex (0.16 g, 0.03 mmol) was suspended in 10 ml dry toluene upon which MAO was added (2.00 ml, 300.0 mmol, 10% wt in toluene). The resin immediately turned dark blue. After stirring for 1 hr, ethylene gas was bubbled through the suspension for 1 min and then the reaction vessel was sealed to a pressure of 5 psi. An internal thermocouple measured a 29° C. exotherm over a 20 min period. After stirring for an additional 1.5 hr, the temperature slowly dropped back to room temperature and the viscous solution was filtered and the beads were washed with toluene (3×10 ml). The filtrate was concentrated and then quenched with MeOH upon which white rubber-like (poly)ethylene formed immediately. This material was filtered and dried to give 1.60 g of (poly)ethylene. The beads were dried under high vacuum and afforded 1.60 g of material corresponding to a 10-fold mass increase of the polystyrene beads.

An identical procedure was performed with the exception that the MAO activated catalyst was washed with toluene (3×10 ml). After the excess MAO was filtered off, the resin-bound catalyst was taken up in 10 ml toluene prior to the introduction of ethylene. An identical outcome was obtained to that described earlier. When this washed resin was taken up in 10 ml dry hexane instead of toluene, less (poly)ethylene was obtained on the bead as well in the filtrate, both weighing 0.26 g.

The above example demonstrated that the supported catalysts of the present invention can catalyze the polymerization of olefins.

4.2 Ethylene polymerization with [2-Ph)PMI(2,6-(Pr)$_2$Ph)] NiBr$_2$/MAO

To a suspension of 6 mg (0.01 mmol) of [2-Ph)PMI(2,6-(Pr)$_2$Ph)]NiBr$_2$ in 5 mL of anhydrous, degassed toluene was added 3.3 mL (5 mmol) of 10% MAO in toluene and the resultant green solution was stirred at RT for 1 h. This solution was then flushed with ethylene and stirred under 10 psi of ethylene for 2 h. To the reaction mixture was added 4 M HCl (50 mL) and Et$_2$O (100 mL), the layers were separated, and the organic layer was dried over MgSO$_4$. Removal of the volatiles by rotary evaporation provided 1.3 g of polymeric material.

4.3 Polymerization of Ethylene with (2,4,6-Me)$_2$DAB(1-Methoxyethoxypropyl)Et Nickel (II) Dibromide Scheme 21

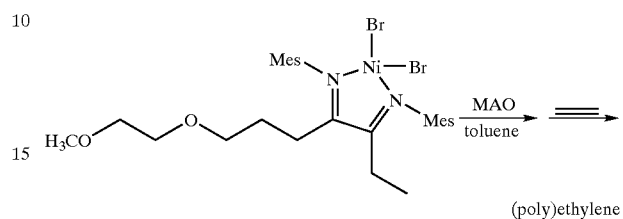

(2,4,6-Me)$_2$DAB(1-methoxyethoxypropyl)ethyl nickel (II) dibromide (0.02 g, 0.03 mmol) was suspended in 15 ml dry toluene upon which MAO was added (2.00 ml, 300.0 mmol, 10% wt in toluene). The solution turned dark blue over a 1 hour period. After stirring for 1 hr, ethylene gas was bubbled through the suspension for 1 min and then the reaction vessel was sealed to a pressure of 5 psi. An internal thermocouple measured a 23° C. exotherm over a 45 min period. After stirring for an additional 1.5 hr, the temperature slowly dropped back to room temperature and the solution was quenched with MeOH followed by 5 N HCl. The precipitated polyethylene was collected by filtration and afforded 1.38 g of polyethylene after drying under high vacuum.

4.4 Polymerization of Ethylene with (2,4,6-Me)$_2$DAB(Me) EtPh Nickel (II) Dibromide Scheme 22

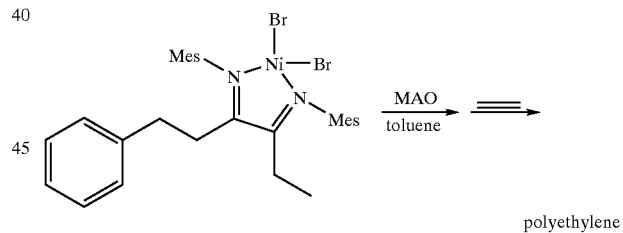

(2,4,6-Me)$_2$DAB(Me)EtPh nickel (II) dibromide (0.02 g, 0.03 mmol) was suspended in 15 ml dry toluene upon which MAO was added (2.00 ml, 9.33 mmol, 10% wt in toluene). The solution turned dark blue over a 1 hour period. After stirring for 1 hr, ethylene gas was bubbled through the suspension for 1 min and then the reaction vessel was sealed to a pressure of 5 psi. An internal thermocouple measured a 19° C. exotherm over a 45 min period. After stirring for an additional 1.5 hr, the temperature slowly dropped back to room temperature and the solution was quenched with MeOH followed by 5 N HCl. The precipitated polyethylene was collected by filtration and afforded 2.10 g of polyethylene after drying under high vacuum.

The above examples demonstrated the utility of the supported and unsupported catalysts of the present invention in olefin polymerization reactions.

4.5 Polymerization of Ethylene with (2,4,6-Me)₂DAB(Me)Et Nickel (II) Dibromide PEG Polystyrene

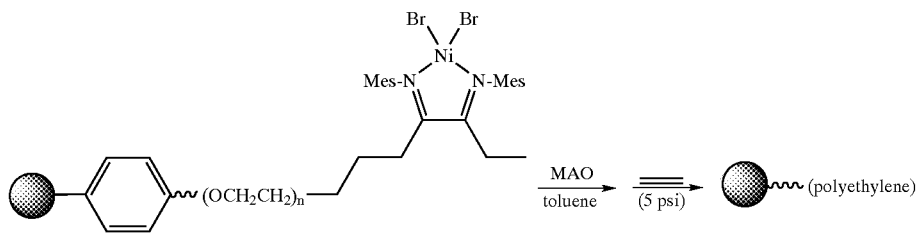

Scheme 23

The above resin-bound nickel(II) dibromide resin. (0.20 g, 0.02 mmol, 0.10 mmol/g) was suspended in 20 ml dry toluene upon which MAO was added (2.00 ml, 300.0 mmol, 10% wt in toluene). The resin immediately turned dark blue. After stirring for 1 hr, ethylene gas was bubbled through the suspension for 1 min and then the reaction vessel was sealed to a pressure of 5 psi. An internal thermocouple measured a 3° C. exotherm over a 45 min period. After stirring for an additional 1.5 hr, the temperature slowly dropped back to room temperature and the solution was filtered and the beads were washed with toluene (3×10 ml). The beads were dried under high vacuum and afforded 0.67 g of material corresponding to a 3-fold mass increase of the polystyrene beads. The filtrate afforded no polyethylene.

4.6 Polymerization of Ethylene with (2,4,6-Me)₂DAB(Me)Et Palladium (II) (Me)Cl PEG Polystyrene

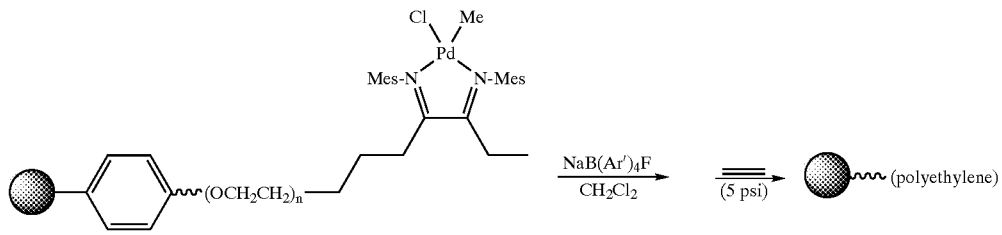

Scheme 24

The above resin-bound palladium (II) (Me)Cl resin (0.20 g, 0.02 mmol, 0.10 mmol/g) was suspended in 20 ml dry CH₂Cl₂ upon which NaB(Ar')₄F was added (18 mg, 0.02 mmol). The resin turned brownish-red over a 1 hr period upon which ethylene gas was bubbled through the suspension for 1 min. The reaction vessel was sealed to a pressure of 5 psi. No exotherm was observed throughout the course of the reaction. After stirring for an additional 1.5 hr, the solution was filtered and the beads were washed with toluene (3×10 ml). The beads were dried under high vacuum and afforded 0.25 g of material corresponding to a 20% mass increase of the polystyrene beads. The filtrate afforded no polyethylene.

4.7 Polymerization of Ethylene with (2,4,6-Me)2DAB(Me)Et Palladium (II) (Me)Cl Polystyrene

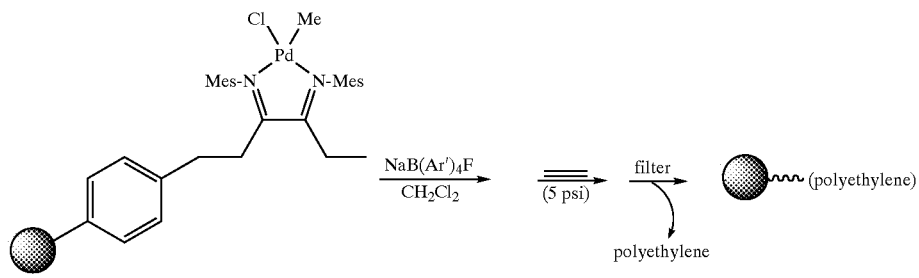

Scheme 25

The above resin-bound palladium (II) (Me)Cl resin (0.10 g, 0.03 mmol, 0.32 mmol/g) was suspended in 25 ml dry CH₂Cl₂ upon which NaB(Ar')₄F was added (30 mg, 0.03 mmol). The resin turned brownish-red over a 1 hr period-upon which ethylene gas was bubbled through the suspension for 1 min. The reaction vessel was sealed to a pressure of 5 psi. A 23° C. was observed throughout the course of the reaction. After stirring for an additional 1.5 hr, the solution was filtered and the beads were washed with toluene (3×10 ml). The beads were dried under high vacuum and afforded 0.25 g of material corresponding to a 100% mass increase of the polystyrene beads. Workup of the filtrate afforded 2.28 g of polyethylene as a colorless gum. Gel permeation chromatography (toluene, 23° C., polystyrene reference): $M_n$=18,518; $M_w$=31,811; $M_w/M_n$=1.72.

4.8 Polymerization of Ethylene with $(2,4,6-Me)_2DAB(Me)$ Et Palladium (II) (Me)Cl (2,4,6-Me)$_2$DAB(Me)Et Palladium (II) (Me)Cl (0.02 g, 0.03 mmol) was dissolved in 25 ml dry $CH_2Cl_2$ upon which $NaB(Ar')_4F$ was added (30 mg, 0.03 mmol). The solution turned brownish-red over a 1 hr period upon which ethylene gas was bubbled through the suspension for 1 min. The reaction vessel was sealed to a pressure of 5 psi. A 28° C. exotherm was observed throughout the course of the reaction. After stirring for an additional 2.5 hr, the solution was filtered through celite. Workup of the filtrate afforded 3.50 g of polyethylene as a colorless gum. Gel permeation chromatography (toluene, 23° C., polystyrene reference): $M_n$=21,016; $M_w$=31,471; $M_w/M_n$=1.50.

4.9 Hexene polymerization with [2-Ph)PMI(2,6-(Pr)$_2$Ph)] $NiBr_2$/MAO

To a suspension of 6 mg (0.01 mmol) of [2-Ph)PMI(2,6-(Pr)$_2$Ph)]NiBr$_2$ in 1 mL of anhydrous, degassed toluene was added 3.3 mL (5 mmol) of 10% MAO in toluene and the resultant green solution was stirred at RT for 1 h. To this solution was then added 8.4 g (100 mmol) of hexene and the solution was stirred under $N_2$ for 24 h. To the reaction mixture was added 4 M HCl (50 mL) and $Et_2O$ (100 mL), the layers were separated, and the organic layer was dried over $MgSO_4$. Removal of the volatiles by rotary evaporation provided 3.9 g (46%) of polymeric material.

Example 5

Example 5 details the preparation of a pyridyl imine ligand and its nickel complex. The catalyst was used to polymerize both hexene and ethylene. The synthetic route to the pyridyl imine nickel complex is displayed in Scheme 27.

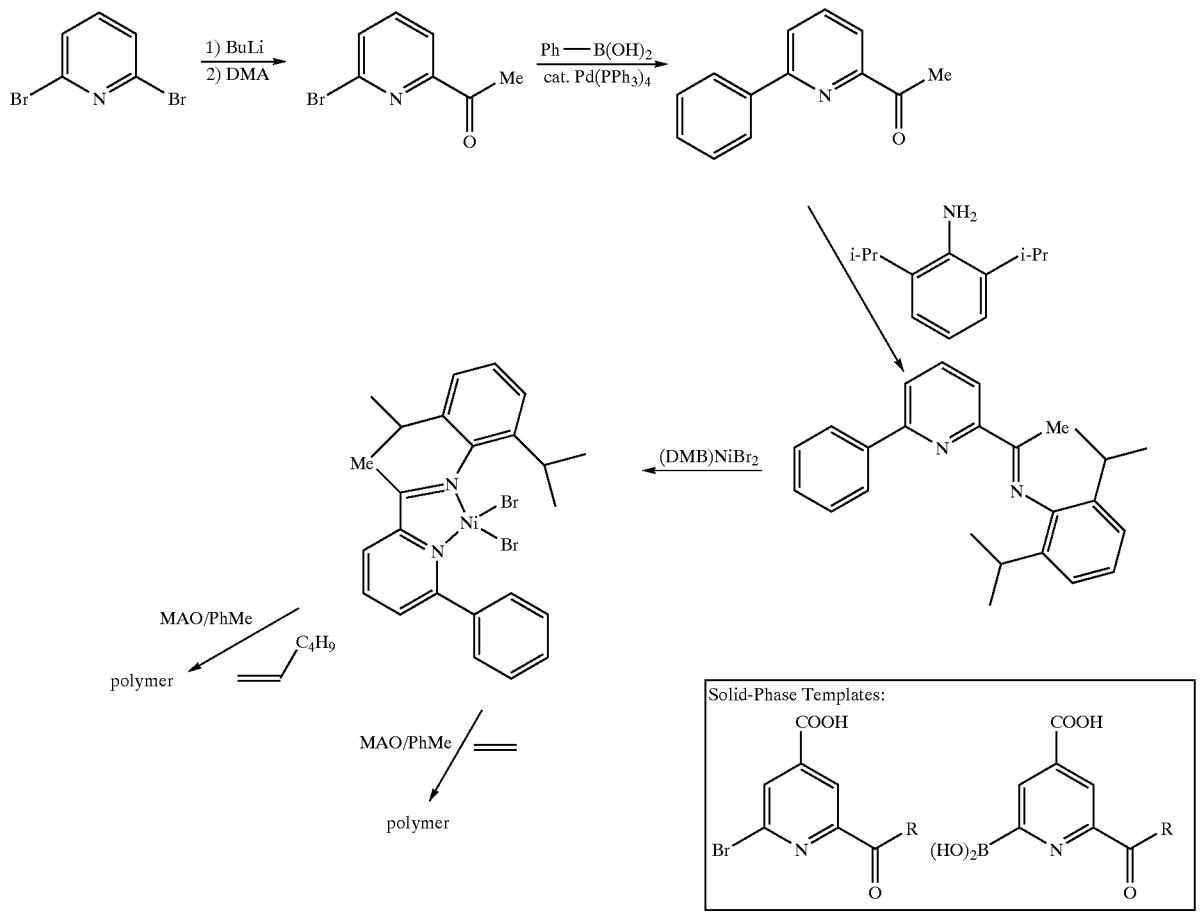

5.1 Preparation of 2-acetyl-6-bromopyridine

To a solution of 3.00 g (12.7 mmol) of 2,6-dibromopyridine in 20 mL anhydrous. $Et_2O$ at −78° C. was added dropwise over 30 min. 8.0 mL (12.8 mmol) of 1.6 M n-BuLi in cyclohexane. After stirring for 3 h at −78° C., 8.2 mL (88 mmol) of N,N-dimethylacetamide was added dropwise and the solution was stirred at −78° C. for 1 h. On warming to RT, $Et_2O$ (100 mL) and saturated aqueous $NH_4Cl$ (50 mL) were added and the layers were separated. The organic layer was dried over $Na_2SO_4$ and the volatiles were removed by rotary evaporation. The resulting yellow solid was recrystallized from hexanes to provide 1.8 g (71%) of 2-acetyl-6-bromopyridine as colorless crystals. $^1$H NMR ($CDCl_3$): σ2.81 (s, 3H); 7.67–7.77 (m, 2 H); 8.22 (dd, J=6.8, 1.6 Hz, 1 H). Mass Spec.: m/e 200.

5.2 Preparation of 2-acetyl-6-phenylpyridine

To a Schlenk tube charged with a solution of 200 mg (1.0 mmol) of 2-acetyl-6-bromopyridine and 23 mg (0.02 mmol) of $(Ph_3P)_4Pd$ in 10 mL of degassed toluene was added a solution of 150 mg (1.2 mmol) phenylboronic acid and 270 mg (2.5 mmol) $Na_2CO_3$ in 8 mL of degassed 4:1 $H_2O$/MeOH. The biphasic mixture was heated to 80° C. with rapid stirring for 1 h. On cooling to RT, $Et_2O$ (50 mL) was added and the layers were separated. The organic layer was dried over $Na_2SO_4$ and the volatiles were removed by rotary evaporation. The resulting oil was chromatographed on silica with 10–50% $CH_2Cl_2$/hexanes eluent to provide 176 mg (89%) of 2-acetyl-6-phenylpyridine as a white powder. $^1$H NMR ($CDCl_3$); δ 2.84 (s, 3H); 7.43–7.62 (m, 3 H); 7.91–8.08 (m, 3 H); 8.18 (d, J=6.6 Hz, 2H). Mass Spec.: m/e 197.

5.3 Preparation of 2-acetyl-6-phenylpyridine 2,6-di(Isopropyl)phenyl imine [(2-Ph)PMI(2,6-$(Pr)_2$Ph)]

A solution of 197 mg (mmol) of 2-acetyl-6-phenylpyridine and 266 mg (1.5 mmol) of 2,6-diisopropylaniline in 5 mL anhydrous MeOH and 0.1 mL of 0.1 M $H_2SO_4$ in MeOH was heated to 50° C. for 12 h. The volatiles were removed by rotary evaporation and the crude material chromatographed on silica with 5% EtOAc/hexanes eluent to provide 287 mg (80%) of (2-Ph)PMI(2,6-$(Pr)_2$Ph) as a yellow solid. $^1$H NMR ($CDCl_3$): δ 1.17 (ddd, J=4.6, 1.7, 0.7 Hz, 12H); 2.23 (d, J=2.5 Hz, 3 H); 2.73 (dq, J=6.8, 2.5 Hz); 7.10–7.25 (m, 3 H); 7.60–7.75 (m, 2 H); 7.90–8.06 (m, 2 H); 8.33–8.40 (m, 1 H). Mass Spec.: m/e 356.

5.4 Preparation of [(2-Ph)PMI(2,6-$(Pr)_2$Ph)]$NiBr_2$

A suspension of 71 mg (0.2 mmol) (2-Ph)PMI(2,6-$(Pr)_2$Ph) and 62 mg (0.2 mmol) of (dimethoxyethane)nickel(II) bromide in anhydrous $CH_2Cl_2$ was stirred at RT under $N_2$ for 48 h. The volatiles were removed by rotary evaporation and the solid was washed several times with hexanes to provide 101 mg (88%) of 1 [(2-Ph)PMI(2,6-$(Pr)_2$Ph)]$NiBr_2$ as an orange powder.

The above example demonstrated that pyridyl imines can be prepared by the methods of the present invention and that these imines are of use in polymerizing olefins. Solid phase analogues of the above catalysts are prepared using the starting materials shown in Scheme 13 (inset), above.

Example 6

This example illustrates reaction schemes which can be used to prepare a variety of [2,0], [2,1], and [2,2] ligand libraries. Such [2,0], [2,1], and [2,2] ligand libraries can be prepared using solution or solid phase methodologies from a salen-based scaffold using the synthetic method outlined in Scheme 14, wherein $R^1$ and $R^2$ are defined as in the section above describing diimine libraries.

Scheme 28

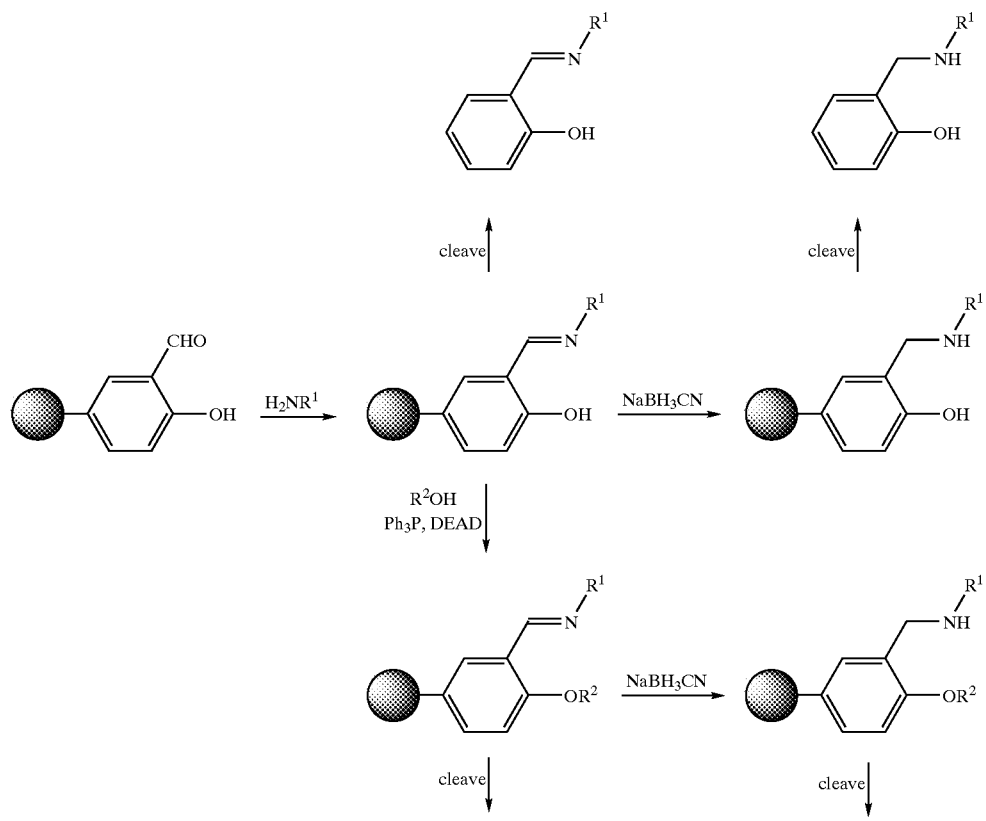

-continued

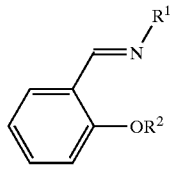

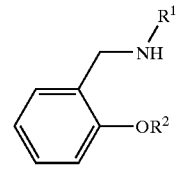

Scheme 28 describes chemistry relevant to both solution and solid phase methodologies. When this chemistry is performed via solid phase chemistries the scaffold is bound to a solid particle represented by the ball in the above figure.

The [2,0] ligand libraries can be converted into organometallic libraries using the displacement or oxidative addition methods described above for the diimine systems. The [2,1] ligand libraries can be converted into organometallic libraries using oxidative addition or metathesis reactions. Oxidative addition of the heteroatom—proton bound to a low valent metal precursor to form a hydride or hydrocarbyl ligand-metal complex is an effective method of creating reactive organometallic libraries. Metathesis reactions are also useful for producing organometallic libraries from [2,1] ligand libraries. The Bronsted acidic libraries described in the above figure can be used directly in metathesis reactions by contacting said libraries with metal reagents (including main group alkyls such as trimethylaluminum) containing leaving group ligands capable of abstracting the acidic proton on the [2,1] ligand. Alternatively, the [2,1] ligand libraries can be deprotonated to form metal salt libraries, which can be further reacted with metal complexes to undergo a metathesis reaction. Other metathesis reactions, such as those resulting in the loss of tin or silyl byproduct can also be envisioned.

Diamide based organometallic libraries can be prepared from diamino ligand libraries using oxidative addition or metathesis reactions similar to those described above. The diamino ligand libraries can be prepared using the synthetic procedure described in FIGS. 2B, 7, and 11.

Tetradentate [4,0] ligand libraries can be constructed by combining two [2,0] ligand fragments as illustrated in Scheme 15. One example of such a combination, is illustrated in the figure below. [4,0] ligand-metal libraries can be prepared by contacting the [4,0] ligand with a suitable transition metal precursor in a manner similar to that described for the preparation of [2,0] bis-imine-metal libraries.

Scheme 29

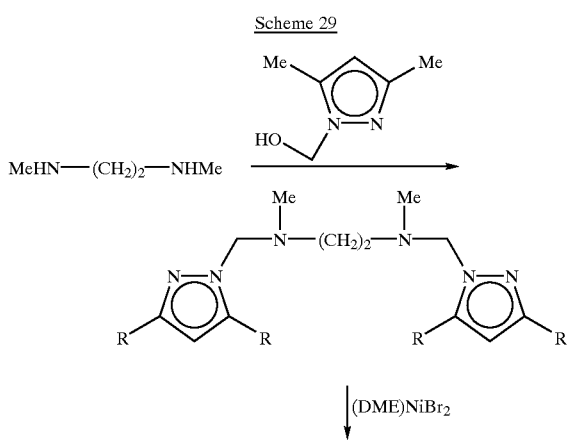

-continued

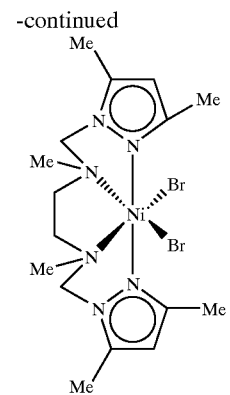

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method of making an array of metal-ligand compounds, said method comprising:
   (a) providing at least a first metal-binding ligand and a second metal-binding ligand to first and second regions of a substrate, wherein (i) said first and second metal-binding ligands are different from each other, (ii) said first and second metal-binding ligands are (2,2) or (2,1) ligands, and (iii) said first and second metal-binding ligands are asymmetric; and
   (b) delivering a first metal ion to said first region and a second metal ion to said second region, thereby forming a first metal-ligand compound and a second metal-ligand compound, wherein said first metal ion and said second metal ion are the same or different from each other.

2. The method as recited in claim 1, wherein said first and second metal-ligand compounds are organometallic compounds.

3. The method as recited in claim 1, wherein said first and second metal-ligand compounds are homogeneous catalysts.

4. The method as recited in claims 3 wherein said homogeneous catalysts are polymerization catalysts.

5. The method as recited in claim 1, wherein said first and second metal-ligand compounds are heterogeneous catalysts.

6. The method as recited in claim 1 wherein said first and second metal-ligand compounds are metallocene compounds.

7. The method as recited in claim 1 wherein said first and second metal-ligand compounds are activator-free catalysts.

8. The method as recited in claim 7 wherein said activator-free catalysts are homogeneous catalysts.

9. The method as recited in claim 7 wherein said activator-free catalysts are heterogeneous catalysts.

10. The method as recited in claim 1 wherein said first and second metal-binding ligands are ancillary ligands.

11. The method as recited in claim 1 wherein said first and second metal ions are each transition metal ions.

12. The method as recited in claim 1 wherein said first and second metal ions are independently selected from the group consisting of Pd, Ni, Pt, Ir, Rh, Cr, Mo, W and Co.

13. The method as recited in claim 1 wherein said first and second metal-binding ligands are unsupported.

14. The method as recited in claim 1 wherein said substrate has a configuration selected from the group consisting of: (i) a porous or non-porous substrate, wherein a sample chamber is filled with reactant gas at pressure P and each of said metal-ligand compounds is selectively activated; and (ii) a porous substrate, wherein reactant gas at pressure P is driven through each of said metal-ligand compounds and the substrate into a region of lower pressure, and wherein each of said metal-ligand compounds is supported and selectively activated.

15. The method as recited in claim 1 wherein each of said metal-ligand compounds is synthesized in an area of less than 25 cm$^2$.

16. The method as recited in claim 1 wherein each of said metal-ligand compounds is synthesized in an area of less than 10 cm$^2$.

17. The method as recited in claim 1 wherein each of said metal-ligand compounds is synthesized in an area of less than 1 cm$^2$.

18. The method as recited in claim 1 wherein each of said metal-ligand compounds is synthesized in an area of less than 1 mm$^2$.

19. The method as recited in claim 1 wherein each of said metal-ligand compounds is synthesized in an area of less than 10,000 $\mu$m$^2$.

20. The method as recited in claim 1 wherein each of said metal-ligand compounds is synthesized in an area of less than 1,000 $\mu$m$^2$.

21. The method as recited in claim 1 wherein each of said metal-ligand compounds is synthesized in an area of less than 100 $\mu$m$^2$.

22. The method as recited in claim 1 wherein each of said metal-ligand compounds is synthesized in an area of less than 1 $\mu$m$^2$.

23. The method as recited in claim 1 wherein at least 10 different metal-ligand compounds are synthesized on said substrate.

24. The method as recited in claim 1 wherein at least 20 different metal-ligand compounds are synthesized on said substrate.

25. The method as recited in claim 1 wherein at least 50 different metal-ligand compounds are synthesized on said substrate.

26. The method as recited in claim 1 wherein at least 100 different metal-ligand compounds are synthesized on said substrate.

27. The method as recited in claim 1 wherein at least 200 different metal-ligand compounds are synthesized on said substrate.

28. The method as recited in claim 1 wherein at least 10 different metal-ligand compounds are prepared in individual wells of said substrate.

29. The method as recited in claim 1 wherein at least 20 different metal-ligand compounds are prepared in individual wells of said substrate.

30. The method as recited in claim 1 wherein at least 50 different metal-ligand compounds are prepared in individual wells of said substrate.

31. The method as recited in claim 1 wherein at least 100 different metal-ligand compounds are prepared in individual wells of said substrate.

32. The method as recited in claim 1 wherein each of said metal-binding ligands is contacted with a main group metal alkyl complex such that said first and second metal-ligand compounds are each in the mono- or di-protic form.

33. The method as recited in claim 32 wherein said main group metal alkyl complex is a trialkylaluminum complex.

34. A method as recited in claim 32 wherein said metal-ligand compounds are useful for an organic transformation reaction requiring Lewis acidic sites.

35. A method as recited in claim 34 wherein said organic transformation reaction is selected from the group consisting of stereo-selective coupling reactions, olefin oligomerization reactions and olefin polymerization reactions.

36. The method as recited in claim 32 wherein said metal-ligand compounds are further modified by reaction with an ion-exchange activator to produce an array of ligand-stabilized cationic aluminum reagents.

37. The method as recited in claim 36 wherein said ion-exchange activator is [PhNMe$_2$H][B(C$_6$F$_5$)$_4$].

38. The method as recited in claim 36 wherein said ligand-stabilized cationic aluminum reagents can be used as catalysts for a reaction selected from the group consisting of organic coupling reactions, olefin oligomerization reactions and olefin polymerization reactions.

39. The method of claim 1, wherein said ligands are provided by dispensing the ligands into said regions.

40. The method of claim 1, wherein said ligands are provided by synthesis of said ligands in said regions.

41. The method of claim 40, wherein said ligands are provided by synthesis of said ligands on a synthesis support in said regions.

* * * * *